(12) United States Patent
Tan et al.

(10) Patent No.: US 11,186,865 B2
(45) Date of Patent: Nov. 30, 2021

(54) SINGLE CELL RNA AND MUTATIONAL ANALYSIS PCR (SCRM-PCR): A METHOD FOR SIMULTANEOUS ANALYSIS OF DNA AND RNA AT THE SINGLE-CELL LEVEL

(71) Applicant: AGENCY FOR SCIENCE, TECHNOLOGY AND RESEARCH, Singapore (SG)

(72) Inventors: Min-Han Tan, Singapore (SG); Igor Cima, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 401 days.

(21) Appl. No.: 15/541,295

(22) PCT Filed: Jan. 21, 2016

(86) PCT No.: PCT/SG2016/050026
§ 371 (c)(1),
(2) Date: Jun. 30, 2017

(87) PCT Pub. No.: WO2016/118085
PCT Pub. Date: Jul. 28, 2016

(65) Prior Publication Data
US 2019/0119721 A1    Apr. 25, 2019

(30) Foreign Application Priority Data
Jan. 21, 2015  (SG) ............................ 10201500472R

(51) Int. Cl.
| C12Q 1/68 | (2018.01) |
| C12Q 1/686 | (2018.01) |
| C12Q 1/6806 | (2018.01) |
| C12Q 1/6876 | (2018.01) |

(52) U.S. Cl.
CPC ........... *C12Q 1/686* (2013.01); *C12Q 1/6806* (2013.01); *C12Q 1/6876* (2013.01); *C12Q 2537/143* (2013.01); *C12Q 2539/103* (2013.01); *C12Q 2539/105* (2013.01); *C12Q 2549/119* (2013.01)

(58) Field of Classification Search
CPC .................................................... C12Q 1/686
See application file for complete search history.

(56) References Cited

U.S. PATENT DOCUMENTS

| 8,889,361 | B2 | 11/2014 | Wen-Tien |
| 2003/0082616 | A1 | 5/2003 | Tomita |
| 2009/0191535 | A1 | 7/2009 | Connelly et al. |
| 2013/0122539 | A1 | 5/2013 | Li et al. |
| 2014/0315295 | A1 | 10/2014 | Makarova et al. |
| 2014/0322743 | A1 | 10/2014 | Tang et al. |

FOREIGN PATENT DOCUMENTS

| CN | 102304581 B | 10/2013 | |
| CN | 104141013 A | 11/2014 | |
| FR | 2926091 A1 | 7/2009 | |
| WO | WO 94/08032 A1 | 4/1994 | |
| WO | WO 1994/08032 A1 | 4/1994 | |
| WO | 20030082616 A1 | 5/2003 | |
| WO | WO-2014028378 A2 * | 2/2014 | ............ B01F 3/0807 |

OTHER PUBLICATIONS

Hurteau GJ, Spivack SD. mRNA-specific reverse transcription—polymerase chain reaction from human tissue extracts. Anal Biochem. Aug. 15, 2002; 307(2):304-15. (Year: 2002).*
Joo CH, Lee H, Kim E, Lee B, Cho YK, Kim YK. Differential amplifying RT-PCR: a novel RT-PCR method to differentiate mRNA from its DNA lacking intron. J VirolMethods. Feb. 2002; 100(1-2)71-81. (Year: 2002).*
Moe Myint, N.N., 2017. Assessing Circulating Cell-free Tumour DNA as a Potential Biomarker for Early Detection and Chemoprevention of Colorectal Cancer (Doctoral dissertation, University of Leicester). (Year: 2017).*
Weerakoon, K.G. and McManus, D.P., 2016. Cell-free DNA as a diagnostic tool for human parasitic infections. Trends in parasitology, 32(5), pp. 378-391. (Year: 2016).*
Hsiao, J.R., Jin, Y.T. and Tsai, S.T., 2002. Detection of cell free Epstein-Barr virus DNA in sera from patients with nasopharyngeal carcinoma. Cancer, 94(3), pp. 723-729. (Year: 2002).*
PCT International Preliminary Report on Patentability for PCT Application No. PCT/SG2016/05026, 6 pgs. (dated Jul. 25, 2017).
Zanetta et al., "Expression of von Willebrand factor, an endothelial cell marker, is up-regulated by angiogenesis factors: A potential method for objective assessment of tumor angiogenesis", International Journal of Cancer, vol. 85, No. 2, Jan. 15, 2000, pp. 281-288.
Ye et al., "Primer-BLAST: A tool to design target-specific primers for polymerase chain reaction", BMC Bioinformatics, vol. 13, No. 134, 2012, 11 pages.
Yasmin-Karim, Sayeda, "Influence of Selectin Mediated Rolling/Adhesion Dynamics in Prostate Cancer Metastasis: a Micro-Channel Model", Department of Chemical Engineering, University of Rochester, 2014, 182 pages.
Wu et al., "BioGPS: an extensible and customizable portal for querying and organizing gene annotation resources", Genome Biology, vol. 10, No. 11, 2009, 8 pages.

(Continued)

Primary Examiner — Teresa E Strzelecka
Assistant Examiner — Olayinka A Oyeyemi

(57) ABSTRACT

A method of simultaneously analyzing RNA and DNA in a sample, the method comprising the step (a) contacting the sample with a reverse primer from a first primer pair directed to a target RNA region to effect reverse transcription of RNA into cDNA with a reverse transcriptase; (b) subsequently contacting the sample with (i) a forward primer from the first primer pair directed to a second cDNA region, (ii) a forward and a reverse primers from a second primer pair targeted to a DNA region, and (ii) a DNA polymerase to simultaneously amplify the target cDNA and target DNA region; and (c) analyzing the amplified target cDNA region and/or amplified target DNA region. Also encompassed are uses of the method to analyze gene expression and mutations, kits comprising primers, enzymes, buffers.

14 Claims, 22 Drawing Sheets

Specification includes a Sequence Listing.

(56) References Cited

OTHER PUBLICATIONS

Wild et al., "Quantitative Assessment of Angiogenesis and Tumor Vessel Architecture by Computer-Assisted Digital Image Analysis: Effects of VEGF-Toxin Conjugate on Tumor Microvessel Density", Microvascuiar Research, vol. 59, 2000, pp. 368-376,.
Vona et al., "Isolation by size of epithelial tumor cells : a new method for the immunomorphological and molecular characterization of circulatingtumor cells", American Journal of Pathology, vol. 156, No. 1, Jan. 2000, pp. 57-63.
Vona et al., "Impact of Cytomorphological Detection of Circulating Tumor Cells in Patients With Liver Cancer", Hepatology, vol. 39, No. 3, 2004, pp. 792-797.
Trapnell et al., "Transcript assembly and quantification by RNA-Seq reveals unannotated transcripts and isoform switching during cell differentiation", Nature Biotechnology, vol. 28, No. 5, May 2010, pp. 511-515.
Trapnell et al., "TopHat: discovering splice junctions with RNA-Seq", Bioinformatics, vol. 25, No. 9, 2009, pp. 1105-1111.
Supplementary Partial European Search Report and Written Opinion received for EP Patent Application No. 16740483.9, dated Jun. 25, 2018, 17 pages.
Supplementary European Search Report and Written Opinion received for EP Patent Application No. 16740483.9, dated Sep. 3, 2018, 20 pages.
Stott et al., "Isolation of circulating tumor cells using a microvortex-generating herringbone-chip", PNAS, vol. 107, No. 43, Oct. 26, 2010, pp. 18392-18397.
Song et al., "Circulating Cancer Cells: Pre- and Post-Chemotherapy Observations", Cancer, vol. 28, No. 3, Sep. 1971, pp. 553-561.
Seal S. H., "A Sieve for the Isolation of Cancer Cells and Other Large Cells From the Blood", Cancer, vol. 17, No. 5, pp. 637-642.
Schug et al., "Promoter features related to tissue specificity as measured by Shannon entropy", Genome Biology, vol. 6, No. 4, 2005, 24 pages.
Schneider et al., "NIH Image to ImageJ: 25 years of Image Analysis", Nat Methods., vol. 9, No. 7, Jul. 2012, pp. 671-675.
Sanchez-Freire et al., "Microfluidic single cell real-time PCR for comparative analysis of gene expression patterns", Nat Protoc., vol. 7, No. 5, 20 pages.
Salsbury A. J., "The significance of the circulating cancer cell", Cancer Treatment Reviews, vol. 2, 1975, pp. 55-72.
Rosenthal, Robert, "Meta-Analytic Procedures for Social Science Research", Sage Publications, Beverly Hills, 1984, pp. 18-20.
Robin et al., "pROC: an open-source package for R and S+ to analyze and compare ROC curves", BMC Bioinformatics, vol. 12, No. 77, 2011, 8 pages.
Rice et al., "Comparing Effect Sizes in Follow-Up Studies: ROC Area, Cohen's d, and r", Law and Human Behavior, vol. 29, No. 5, Oct. 2005, pp. 616-620.
Peixoto et al., "Quantification of Multiple Gene Expression in Individual Cells", Genome Research, vol. 14, 2004, pp. 1938-1947.
Paterlini-Brechot et al., "Circulating tumor cells (CTC) detection: Clinical impact and future directions", Cancer Letters, vol. 253, 2007, pp. 180-204.
Office Action received for Japanese Patent Application No. 2017-538319, dated Nov. 26, 2018, 14 pages (7 pages of English Translation and 7 pages of Office Action).
Office Action received for European Patent Application No. 16740482. 1, dated May 2, 2019, 6 pages.
Office Action received for Chinese Patent Application No. 201680014812.9, dated May 5, 2019, 12 pages (7 pages of English Translation and 5 pages of Office Action).
Office Action received for Chinese Patent Application No. 201680014812.9, dated Aug. 15, 2018, 8 pages (5 pages of English Translation and 3 pages of Office Action).
Ni et al., "Reproducible copy number variation patterns among single circulating tumor cells of lung cancer patients", PNAS, vol. 110, No. 52, Dec. 24, 2013, p. 21083-21088.
Mura et al., "Identification and angiogenic role of the novel tumor endothelial marker CLEC14A", Oncogene, vol. 31, 2011, pp. 1-13.
Mu et al., "Circulating Breast Tumor Cells Exhibit Dynamic Changes in Epithelial and Mesenchymal Composition", Science, vol. 339, Feb. 1, 2013, pp. 580-584.
Mesri et al., "Identification and Characterization of Angiogenesis Targets through Proteomic Profiling of Endothelial Cells in Human Cancer Tissues", PLOS ONE, vol. 8, No. 11, Nov. 2013, p. e78885 (12 pages).
Marrinucci et al., "Fluid Biopsy in Patients with Metastatic Prostate, Pancreatic and Breast Cancers", Phys Biol., vol. 9, No. 1, Feb. 2012, 19 pages.
Magbanua et al., "A Novel Strategy for Detection and Enumeration of Circulating Rare Cell Populations in Metastatic Cancer Patients Using Automated Microfluidic Filtration and Multiplex Immunoassay", PLOS ONE, vol. 10, No. 10, Oct. 23, 2015, p. e0141166 (18 pages).
Mabbott et al., "An expression atlas of human primary cells: inference of gene function from coexpression networks", BMC Genomics, vol. 14, No. 632, 2013, 13 pages.
Lim et al., "Microsieve lab-chip device for rapid enumeration and fluorescence in situ hybridization of circulating tumor cells", Lab Chip, vol. 12, 2012, pp. 4388-4396.
Krebs et al., "Analysis of Circulating Tumor Cells in Patients with Non-small Cell Lung Cancer Using Epithelial Marker-Dependent and -Independent Approaches", Journal of Thoracic Oncology, vol. 7, No. 2, Feb. 2012, pp. 306-315.
Kling Jim, "Beyond counting tumor cells", Nature Biotechnology, vol. 30, No. 7, Jul. 2012, pp. 578-580.
Khoja et al., "A pilot study to explore circulating tumour cells in pancreatic cancer as a novel biomarker", British Journal of Cancer, vol. 106, 2012, pp. 508-516.
Kalka et al., "Transplantation of ex vivo expanded endothelial progenitor cells for therapeutic neovascularization", PNAS, vol. 97, No. 7, Mar. 28, 2000, pp. 3422-3427.
International Search Report and Written Opinion received for PCT Patent Application No. PCT/SG2016/050027, dated Mar. 21, 2016, 16 pages.
International Preliminary Report on Patentability received for PCT Patent Application No. PCT/SG201 6/050027, dated Aug. 3, 2017, 10 pages.
Hou et al., "Clinical Significance and Molecular Characteristics of Circulating Tumor Cells and Circulating Tumor Microemboli in Patients With Small-Cell Lung Cancer", Journal of Clinical Oncology, vol. 30, 2012, 9 pages.
Hou et al., "Circulating Tumor Cells, Enumeration and Beyond", Cancers, vol. 2, 2010, pp. 1326-1250.
Hou et al., "Circulating Tumor Cells as a Window on Metastasis Biology in Lung Cancer", The American Journal of Pathology, vol. 178, No. 3, Mar. 2011, pp. 989-996.
Hothorn et al. "Implementing a Class of Permutation Tests: The coin Package", Journal of Statistical Software, vol. 28, No. 8, 2008, 23 pages.
Hofman et al., "Preoperative Circulating Tumor Cell Detection Using the Isolation by Size of Epithelial Tumor Cell Method for Patients with Lung Cancer is a New Prognostic Biomarker", Clinical Cancer Research, vol. 17, No. 4, Feb. 15, 2011, pp. 827-835.
Hofman et al., "Cytopathologic Detection of Circulating Tumor Cells Using the Isolation by Size of Epithelial Tumor Cell Method: Promisesand Pitfalls", Am. J. Ciin. Pathol., vol. 135, 2011, pp. 146-156.
Herbert et al., "A novel method of differential gene expression analysis using multiple cDNA libraries applied to the identification of tumour endothelial genes", BMC Genomics, vol. 9, No. 153, 2008, 21 pages.
Hallani et al., "Tumor and Endothelial Cell Hybrids Participate in Glioblastoma Vasculature", Biomed Research International, vol. 2014, Article ID 827327, 2014, 9 pages.
Gupta et al., "Mediators of vascular remodelling co-opted for sequential steps in lung metastasis", Nature, vol. 446, Apr. 12, 2007, pp. 765-770.
IP Office of Singapore; Notification of Transmittal of The International Search Report and The Written Opinion of the International

(56) References Cited

OTHER PUBLICATIONS

Searching Authority, or The Declaration for counterpart International Application No. PCT/SG2016/050026 containing International Search Report and Written Opinion, 12 pgs. (dated Mar. 21, 2016).
Ginzinger, O.G., Gene quantification using real-time quantitative PCR: An emerging technology hits the mainstream. Exp Hematol, Jun. 5, 2002, vol. 30, No. 6, pp. 503-512.
Haff, LA, Improved quantitative PCR using nested primers. *PCR Methods Appl*, Jun. 1, 1994, vol. 3, No. 6, pp. 332-337.
Imboden, P. et al., Simultaneous detection of DNA and RNA by differential polymerase chain reaction (DIFF-PCR). *PCR Methods Appl*, Aug. 1, 1993, vol. 3, No. 1, pp. 23-27.
Sakaizawa, K. et al,. Mutation analysis of BRAF and KIT in circulating melanoma cells at the single cell level. Br J Cancer, Jan. 26, 2012, vol. 106, No. 5, pp. 939-946.
Griffiths et al., "Carcinoma of the Colon and Rectum: Circulating Malignant Cells and Five-Year Survival", Cancer, vol. 31, No. 1, Jan. 1973, pp. 226-236.
Goon et al., "Circulating Endothelial Cells, Endothelial Progenitor Cells, and Endothelial Microparticles in Cancer", Neoplasia, vol. 8, No. 2, Feb. 2006 pp. 79-88.
Glaves et al., "Haematogenous dissemination of cells from human renal adenocarcinomas", Br. J. Cancer, vol. 57, 1988, pp. 32-35.
Finkel et al., "Malignant cells in a peripheral blood smear: report of a case", The New England Journal of Medicine, vol. 262, No. 4, pp. 187-188.
Engell H. C., "Cancer Cells in the Blood—A Five to Nine Year Follow up Study", Annals of Surgery, vol. 149, No. 4, Apr. 1959, pp. 457-461.
El-Heliebi et al., "Are morphological criteria sufficient for the identification of circulating tumor cells in renal cancer?", Journal of Translational Medicine, vol. 11, 2013, 17 pages.
Ejeckam et al., "Carcinocythemia due to metastatic oat-cell carcinoma of the lung", CMA, vol. 120, 1979, pp. 336-338.
Dudley, Andrew C., "Tumor endothelial Cells", Cold Spring Harb Perspect Med, Mar. 2012, vol. 2, No. 3, pp. 1-18.
Dome et al., "Circulating endothelial cells, bone marrow-derived endothelial progenitor cells and proangiogenic hematopoietic cells in cancer: From biology to therapy", Critical Reviews in Oncology/Hematology, vol. 69, No. 2, Feb. 2009, pp. 108-124.
Desitter et al., "A New Device for Rapid Isolation by Size and Characterization of Rare Circulating Tumor Cells", Anticancer Research, vol. 31, 2011, pp. 427-441.
Damani et al., "Characterization of Circulating Endothelial Cells in Acute Myocardial Infarction", Science Translational Medicine, vol. 4, No. 126, Mar. 21, 2012, 20 pages.
Croix et al., "Genes Expressed in Human Tumor Endothelium", Science, vol. 289, Aug. 18, 2000, pp. 1197-1202.
Coumans et al., "Filter Characteristics Influencing Circulating Tumor Cell Enrichment from Whole Blood", Plos One, vol. 8, No. 4, Apr. 2013, 12 pages.
Colombo et al., "Comparison of Fibronectin and Collagen in Supporting the Isolation and Expansion of Endothelial Progenitor Cells from Human Adult Peripheral Blood", Plos One, vol. 8, No. 6, Jun. 2013, 9 pages.
Cole et al., "Dissemination of Cancer with Special Emphasis on Vascular Spread and Implantation", Annals of Surgery, vol. 161, No. 5, May 1965, pp. 753-768.
Cohen, Jacob, "Statistical Power Analysis for the Behavioral Sciences", Second Edition, Department of Psychology, 1988, 57 pages.
Cima et al., "Tumor-Derived Circulating Endothelial Cell Clusters in Colorectal Cancer", Science Translational Medicine, vol. 8, No. 345, Jun. 29, 2016, p. 345ra89 (13 pages).
Cima et al., "Label-free isolation of circulating tumor cells in microfluidic devices: Current research and perspectives", Biomicrofluidics, vol. 7, 2013, pp. 11810-11816.
Cho et al., "Characterization of circulating tumor ceil aggregates identified in patients with epithelial tumors", Phys. Biol., vol. 9, 2012, 6 pages.

Champely, Stephane, "Basic functions for power analysis", The pwr Package, Version 1.0, 2006, 14 pages.
Bunn et al., "An introduction to dpIR", Processed with dpIR 1.6.9 in R version 3.5.0, 2018, 16 pages.
Borgia et al., "A Proteomic Approach for the Identification of Vascular Markers of Liver Metastasis", Cancer Res., vol. 70, No. 1, Jan. 1, 2010, pp. 309-319.
Blann et al., "Circulating Endothelial Cells Biomarker of Vascular Disease", Thromb Haemost, Jan. 7, 2005, vol. 93, No. 2, pp. 228-235.
Bethel et al., "Fluid phase biopsy for detection and characterization of circulating endothelial cells in myocardial infarction", Physical Biology, vol. 11, No. 1, 2014, 19 pages.
Bertolini et al., "The multifaceted circulating endothelial cell in cancer: towards marker and target identification", Nature Reviews Cancer, vol. 6, No. 11, Nov. 2006, pp. 835-845.
Beijnum et al., "Isolation of endothelial cells from fresh tissues", Nature Protocols, vol. 3, No. 5, 2008, pp. 1-7.
Bebenek et al., "The Fidelity of Retroviral Reverse Transcriptases", Laboratory of Molecular Genetics, National Institute of Environmental Health Sciences, 1993, pp. 85-102.
Allard et al., "Tumor Cells Circulate in the Peripheral Blood of All Major Carcinomas but not in Healthy Subjects or Patients With Nonmalignant Diseases", Clinical Cancer Research, vol. 10, Oct. 15, 2004, pp. 6897-6904.
Alessandri et al. "Phenotypic and functional characteristics of tumour-derived microvascular endothelial cells", Clinical & Experimental Metastasis, vol. 17, No. 8, Oct. 1999, pp. 655-662.
Adams et al., "Highly Efficient Circulating Tumor Cell Isolation from Whole Blood and Label-Free Enumeration Using Polymer-Based Microfluidics with an Integrated Conductivity Sensor", J. Am. Chem. Soc., vol. 130, No. 27, Jul. 9, 2008, pp. 8633-8641.
Aceto et al., "Circulating Tumor Cell Clusters Are Oligoclonal Precursors of Breast Cancer Metastasis", Cell., vol. 158, Aug. 28, 2014, pp. 1110-1122.
Aboulafia, David M., "Carcinocythemia—A Terminal Manifestation of Metastatic Breast Cancer", The Western Journal of Medicine, vol. 157, No. 6, Dec. 1992, pp. 672-674.
Extended European Search Report for counterpart EP patent application No. 16740482.1, dated May 22, 2018, 12 pgs.
Chul Hyun Joo, et al., "Differential amplifying RT-PCR: a novel RT-PCT method to differentiate mRNA from its DNA lacking intron," Journal of Virological Methods, vol. 100, No. 1-2, pp. 71-81 (2002).
Raymond J. Lenoff, et al., "Multiplexed molecular assay for rapid exclusion of foot-and-mouth disease," Journal of Virological Methods, vol. 153, No. 1, pp. 61-69 (2008).
Bernard Mercier, et al., "Simultaneous screening for HBV DNA and HCV RNA genomes in blood donations using a novel TagMan PCR assay," Journal of Virological Methods, vol. 77, No. 1, pp. 1-9 (1999).
P.N. Nelson, et al., "A polymerase chain reaction to detect a spliced late transcript of human cytomegalovirus in the blood of bone marrow transplant recipients," Journal of Virological Methods, vol. 56, No. 2, pp. 139-148 (1996).
Siddharth S. Dey, et al., "Integrated genome and transcriptome sequencing of the same cell," Nature Biotechnology, vol. 33, No. 3, pp. 285-289 (Jan. 19, 2015).
Peter Van Loo, et al., "Single cell analysis of cancer genomes," Current Opinion in Genetics & Development, vol. 24, pp. 82-91 (Feb. 24, 2014).
B. Molnar, Circulating Tumor Cell Clusters in the Peripheral Blood of Colorectal Cancer Patients; Clinical Cancer Research; vol. 7, 4080-4085, Dec. 2001.
R. A. Sellwood, Circulating Cancer Cells; Brit. med. J., 1964, 1, 1683-1686.
The R Manuals—Core Team. R (2005) R Foundation for Statistical Computing, Vienna, Austria; <https://cran.r-project.org/manuals.html>.
The Intention to Grant for European Application No. 16740482.1 dated Sep. 30, 2020, 25 pages.
The Third Office Action of European Patent Application No. 16740482.1, dated Nov. 15, 2019, 5 pages.

(56) References Cited

OTHER PUBLICATIONS

Siddharth et al., "Integrated genome and transcriptome sequencing from the same cell," Nat. Biotechnol., Jan. 19, 2015, pp. 285-289, vol. 33, No. 3. 16 pages.
Van Loo et al., "Single Cell Analysis of Cancer Genomes," Current Opinion in Genetics & Development, Feb. 24, 2014, pp. 82-91, vol. 24, 10 pages.
"TRI REAGENT®—RNA/ DNA/ Protein Isolation Reagent", Molecular Research Center, Mar. 2017.
"Gentra® Puregene® Handbook: QIAGEN Sample and Assay Technologies", Gentra Systems, Dec. 2014.
Akagi, K.; et al.; "Estimation of Angiogenesis with Anti-CD105 Immunostaining in the Process of Colorectal Cancer Development". Surgery 131, S 109-S 113 (2002). 5 pp.
Armstrong, A. J et al. "Circulating tumor Cells from Patients with Advanced Prostate and Breast Cancer Display Both Epithelial and Mesenchymal Markers". Mol. Cancer Res. 9, 997-1007 (2011). 12 pp.
Carmeliet, P.; et al.; "Angiogenesis in Cancer and Other Diseases". Nature 407, 249-257 (2000). 9 pp.
Carr, A. J.; et al.; "The Expression of Retinal Cell Markers in Human Retinal Pigment Epithelial Cells and Their Augmentation by the Synthetic Retinoid Fenretinide"; Molecular Vision 2011; 17: 1701-1715. 15 pp.
Chang, S. S.; et al.; "Prostate-Specific Membrane Antigen is Produced in Tumor-Associated Neovasculature". Clin. Cancer Res. 5, 2674-2681 (1999). 9 pp.
Denmeade, S. R. et al. "Engineering a Prostate-Specific Membrane Antigen-Activated Tumor Endothelial Cell Prodrug for Cancer Therapy". Sci. Transl. Med. 4, 140ra86 (2012). 22 pp.
Hesse, M.; et al.; "Genes for Intermediate Filament Proteins and the Draft Sequence of the Human Genome: Novel Keratin Genes and a Surprisingly High Number of Peseudogenes Related to Keratin Genes 8 and 18"; Journal of Cell Science 113; 2001, 7 pp.
Hill, A. B.; "The Environment and Disease: Association or Causation?"; Proc. R. Soc. Med. 58, 295-300 (1965). 6 pp.
Ludatscher, R. M.; Luse, S. A. & Suntzeff, V. An electron microscopic study of pulmonary tumor emboli from transplantable Manis hepatoma 5123. Cancer Res. 27, 1939-1952. 15 pp.
Mahdi, F.; "Expression and Colocalization of Cytokeratin 1 and Urokinase Plasminogen Activator Receptor on Endothelial Cells". Blood 97, 2342-2350 (2001). 9 pp.
Miettinen, M.; et al.; "Distribution of Keratins in Normal Endothelial Cells and a Spectrum of Vascular Tumors: Implications in Tumor Diagnosis". Hum. Pathol. 31, 1062-1067 (2000). 6 pp.
Nolan, D. J.; et al.; Molecular Signatures of Tissue-Specific Microvascular Endothelial Cell Heterogeneity in Organ Maintenance and Regeneration. Dev. Cell 26, 204-219 (2013). 16 pp.
Rhim, A. D. et al. "EMT and Dissemination Precede Pancreatic Tumor Formation". Cell 148, 349-361 (2012). 20 pp.
Seaman, S.; et al.; "Genes that Distinguish Physiological and Pathological Angiogenesis". Cancer Cell 11, 539-554 (2007). 25 pp.
Silver, D. A.; "Prostate-Specific Membrane Antigen Expression in Normal and Malignant Human Tissues". Clin. Cancer Res. 3, 81-85 (1997). 6 pp.
Sugino, T.; et al.; "Morphological Evidence for an Invasion-Independent Metastasis Pathway Exists in Multiple Human Cancers". BMC Med. 2, 9 (2004). 8 pp.
Treff, N. R.; et al.; "Single-Cell Whole-Genome Amplification Technique Impacts the Accuracy of SNP Microanay-Based Genotyping and Copy Number Analyses". Mol. Hum. Reproduction. 17, 335-343 (2011). 9 pp.
Yu, M.; et al.; "Circulating Breast Tumor Cells Exhibit Dynamic Changes in Epithelial and Mesenchymal Composition". Science 339, 580-584 (2013). 10 pp.
The Chinese Office Action for Application No. 201680005645.1 dated May 29, 2020, 10 pages.
The European Office Action for Application No. 16740482.1 dated Jun. 19, 2020, 5 pages.
The Second Office Action for Chinese Patent Application No. 201680005645.1, dated Jan. 26, 2021, 15 pages.
International Preliminary Report on Patentability dated Jul. 25, 2017 for Counterpart International Patent Application No. PCT/SG2016/050026, filed Jan. 21, 2016, 6 pages.
The Decision to Grant a European Patent Pursuant to Article 97(1) EPC for European Patent Application No. 16740482.1 dated Feb. 4, 2021, 2 pages.

* cited by examiner

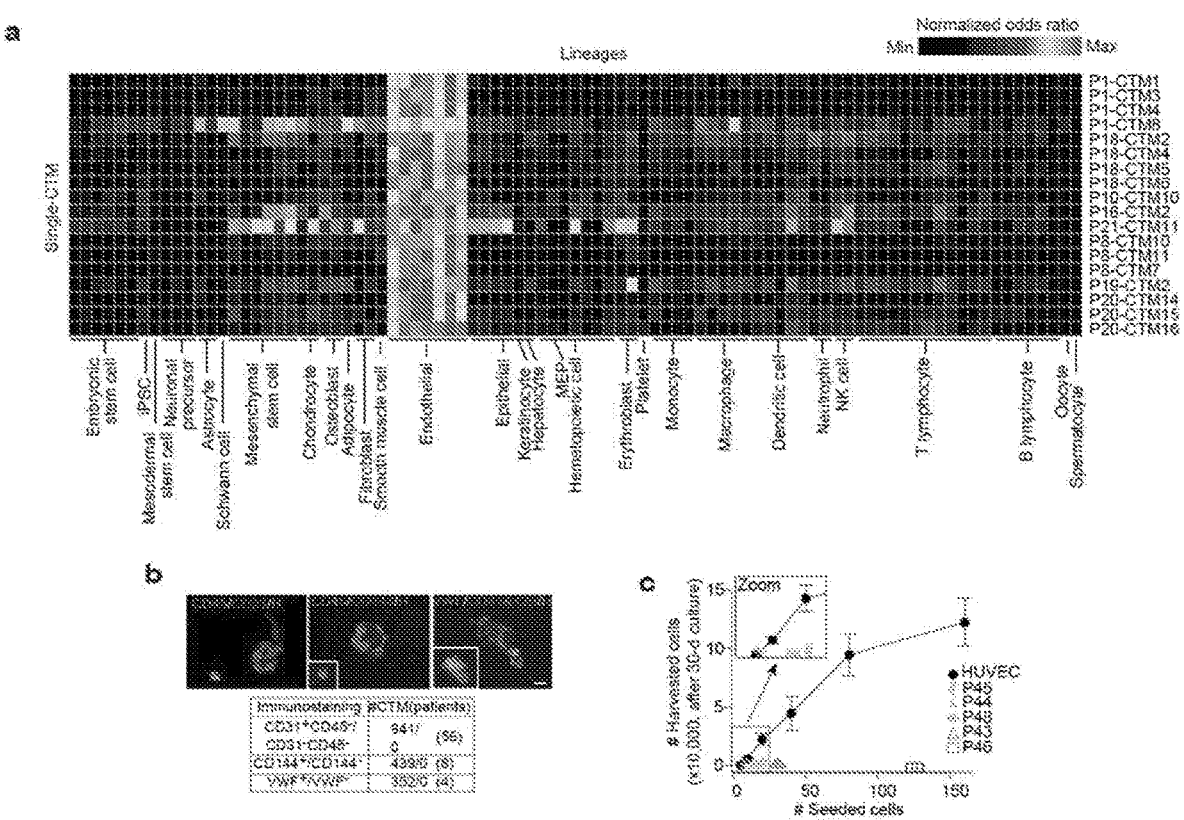
Figure 7a-c (continued)

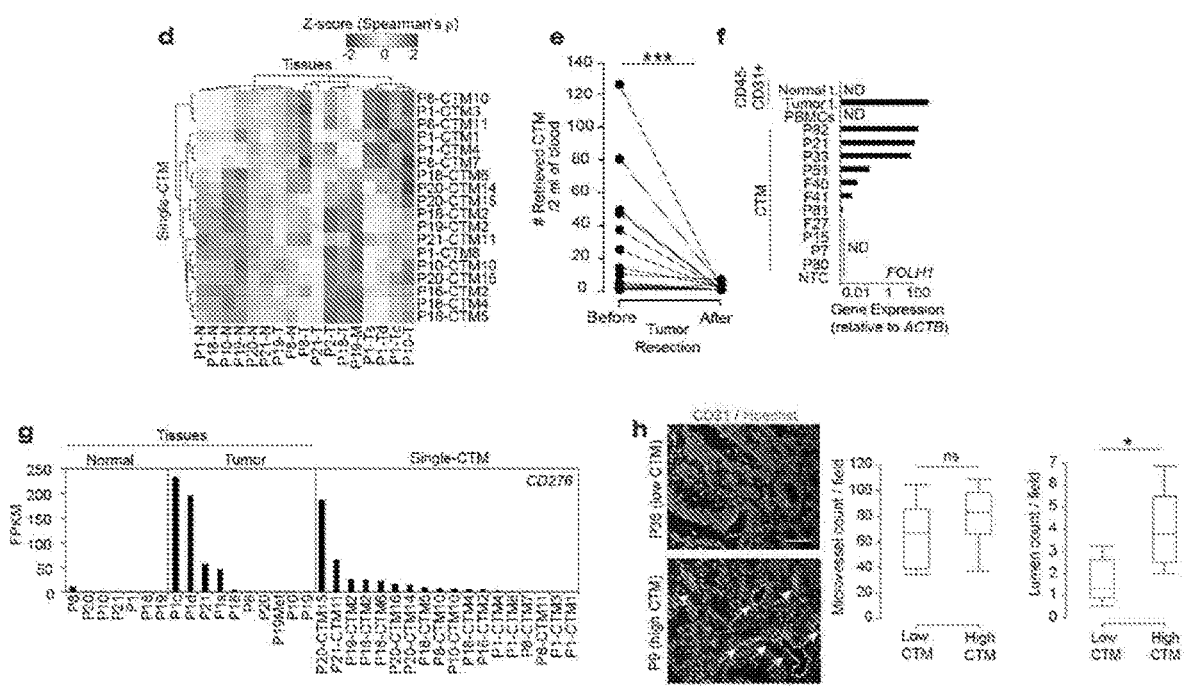
Figure7d-h

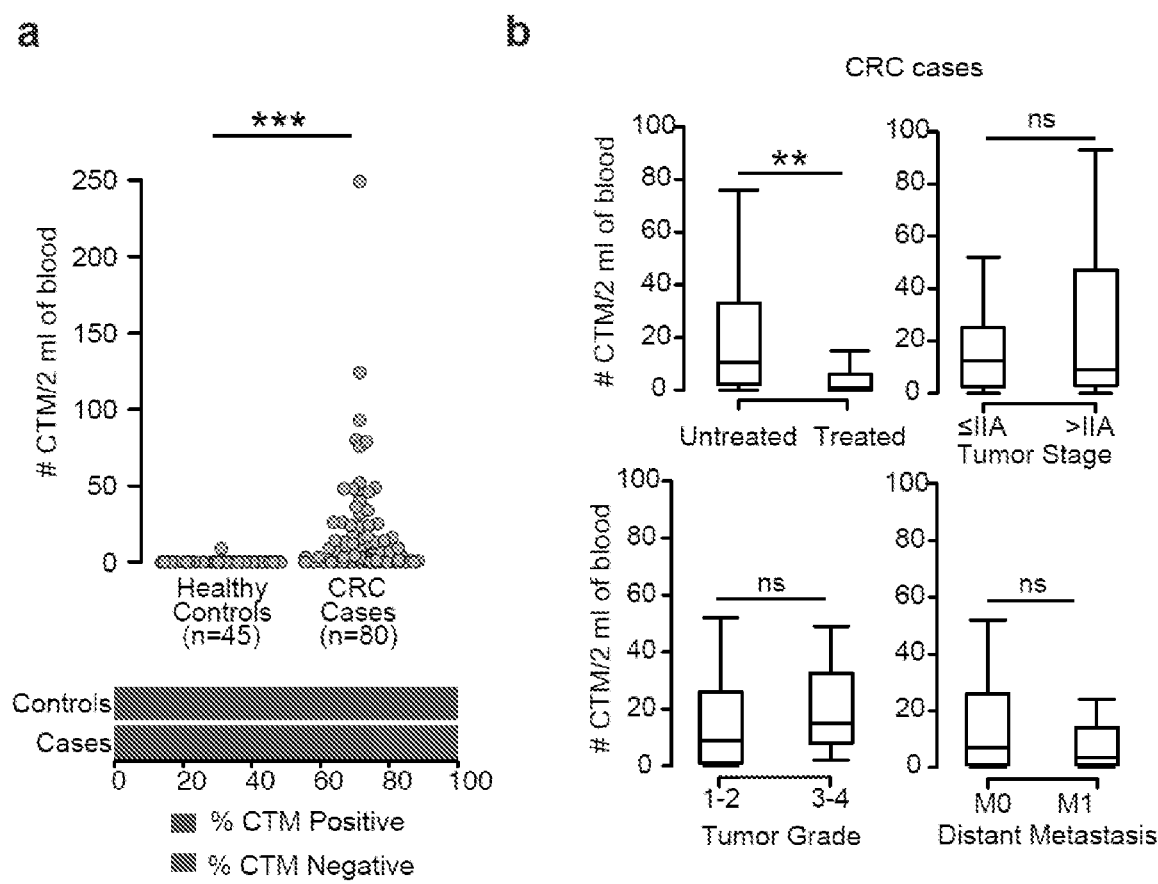
Figure 8a-b (continued)

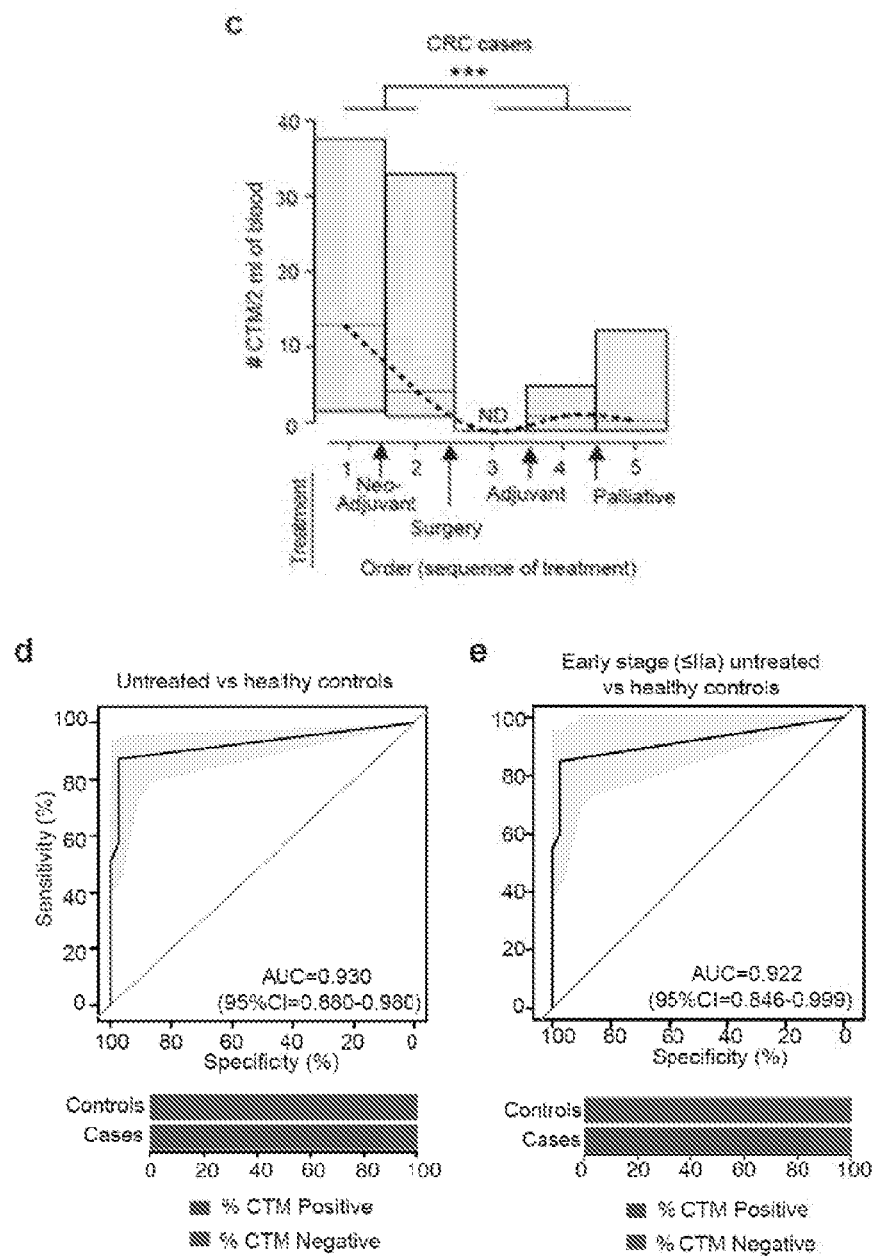
Figure 8c-e a
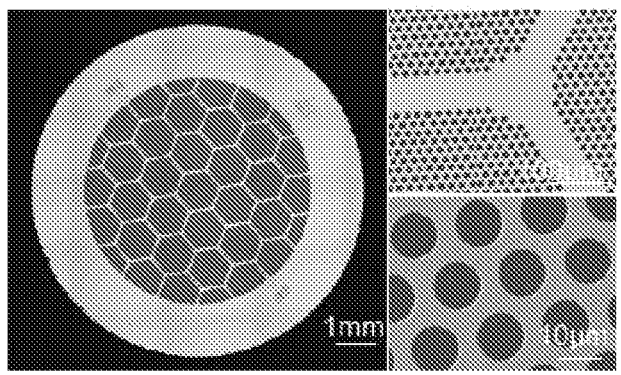
b
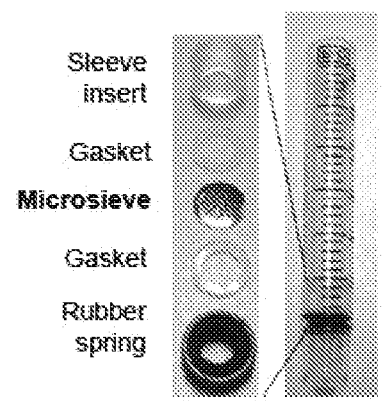
c
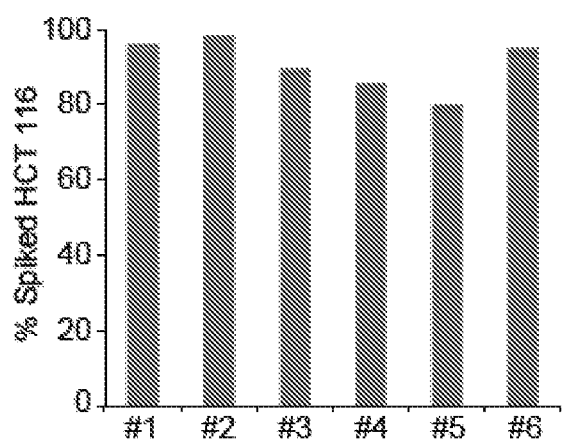
Figure 9a-c (continued)

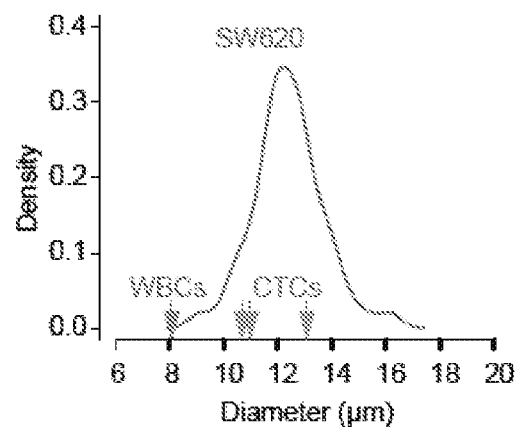
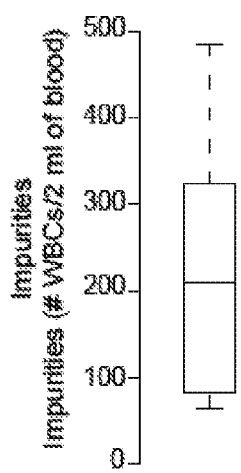
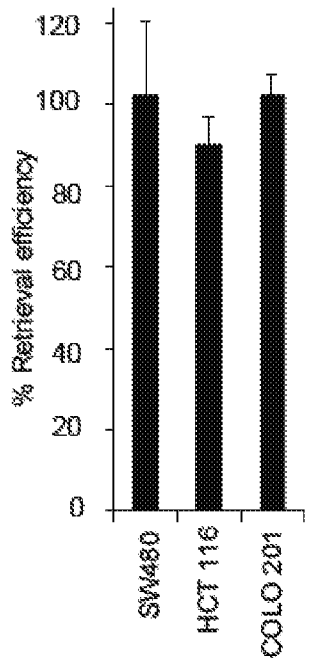
Figure 9d-f

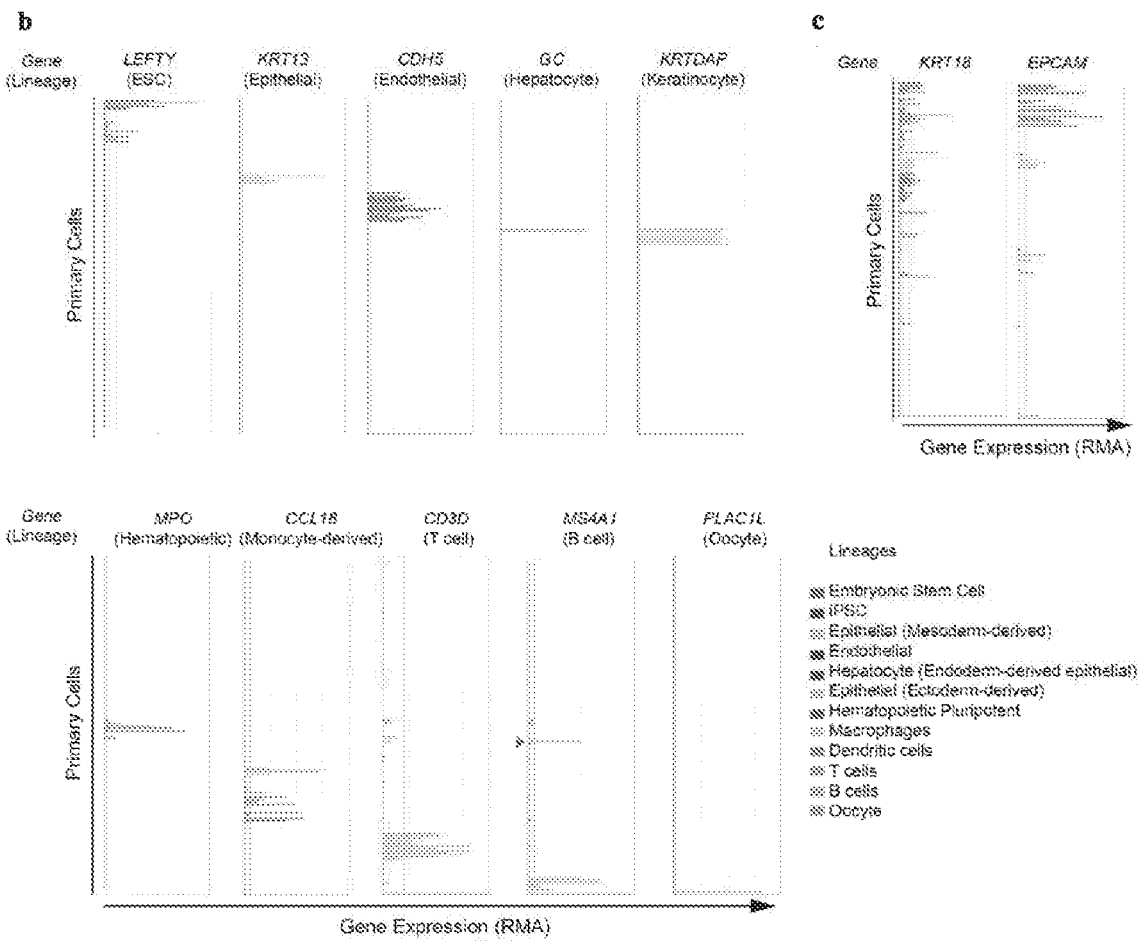
Figure 14b-c

SEQUENCE LISTING

<160> NUMBER OF SEQ ID NOS: 138

<210> SEQ ID NO 1
<211> LENGTH: 24
<212> TYPE: DNA
<213> ORGANISM: Artificial Sequence
<220> FEATURE:
<223> OTHER INFORMATION: CEACAM5 Forward primer

<400> SEQUENCE: 1
cccaagccct ccatctccag caac        24

<210> SEQ ID NO 2
<211> LENGTH: 23
<212> TYPE: DNA
<213> ORGANISM: Artificial Sequence
<220> FEATURE:
<223> OTHER INFORMATION: CEACAM5 Reverse primer

<400> SEQUENCE: 2
gcatccgggc catagaggac att        23

<210> SEQ ID NO 3
<211> LENGTH: 22
<212> TYPE: DNA
<213> ORGANISM: Artificial Sequence
<220> FEATURE:
<223> OTHER INFORMATION: CDX2 Forward primer

<400> SEQUENCE: 3

```
tgggctgctg caaacgctca ac                                            22

<210> SEQ ID NO 4
<211> LENGTH: 25
<212> TYPE: DNA
<213> ORGANISM: Artificial Sequence
<220> FEATURE:
<223> OTHER INFORMATION: CDX2 Reverse primer

<400> SEQUENCE: 4
tttcgtcctg gttttcactt ggctg                                         25

<210> SEQ ID NO 5
<211> LENGTH: 20
<212> TYPE: DNA
<213> ORGANISM: Artificial Sequence
<220> FEATURE:
<223> OTHER INFORMATION: KRT20 Forward primer

<400> SEQUENCE: 5
aaaatggcca tgcagaacct                                               20

<210> SEQ ID NO 6
<211> LENGTH: 20
<212> TYPE: DNA
<213> ORGANISM: Artificial Sequence
<220> FEATURE:
<223> OTHER INFORMATION: KRT20 Reverse primer

<400> SEQUENCE: 6
gaagtcctca gcagccagtt                                               20

<210> SEQ ID NO 7
<211> LENGTH: 16
<212> TYPE: DNA
<213> ORGANISM: Artificial Sequence
<220> FEATURE:
<223> OTHER INFORMATION: FN1 Forward primer

<400> SEQUENCE: 7
ccacgggagc ctcgaa                                                   16

<210> SEQ ID NO 8
<211> LENGTH: 20
<212> TYPE: DNA
<213> ORGANISM: Artificial Sequence
<220> FEATURE:
<223> OTHER INFORMATION: FN1 Reverse primer

<400> SEQUENCE: 8
taaaacctcg gcttcctcca                                               20

<210> SEQ ID NO 9
<211> LENGTH: 20
<212> TYPE: DNA
<213> ORGANISM: Artificial Sequence
<220> FEATURE:
<223> OTHER INFORMATION: CDH2 Forward primer

<400> SEQUENCE: 9
ggatgaagat ggcatggtgt                                               20

<210> SEQ ID NO 10
<211> LENGTH: 20
<212> TYPE: DNA
<213> ORGANISM: Artificial Sequence
```

```
<220> FEATURE:
<223> OTHER INFORMATION: CDH2 Reverse primer

<400> SEQUENCE: 10
cccagtctct cttctgcctt                                              20

<210> SEQ ID NO 11
<211> LENGTH: 17
<212> TYPE: DNA
<213> ORGANISM: Artificial Sequence
<220> FEATURE:
<223> OTHER INFORMATION: SERPINE1 Forward primer

<400> SEQUENCE: 11
gccaagagcg ctgtcaa                                                 17

<210> SEQ ID NO 12
<211> LENGTH: 19
<212> TYPE: DNA
<213> ORGANISM: Artificial Sequence
<220> FEATURE:
<223> OTHER INFORMATION: SERPINE1 Reverse primer

<400> SEQUENCE: 12
cagcagaccc ttcaccaaa                                               19

<210> SEQ ID NO 13
<211> LENGTH: 25
<212> TYPE: DNA
<213> ORGANISM: Artificial Sequence
<220> FEATURE:
<223> OTHER INFORMATION: TWIST1 Forward primer

<400> SEQUENCE: 13
acctagatgt cattgtttcc agaga                                        25

<210> SEQ ID NO 14
<211> LENGTH: 20
<212> TYPE: DNA
<213> ORGANISM: Artificial Sequence
<220> FEATURE:
<223> OTHER INFORMATION: TWIST1 Reverse primer

<400> SEQUENCE: 14
gcagaggtgt gaggatggtg                                              20

<210> SEQ ID NO 15
<211> LENGTH: 20
<212> TYPE: DNA
<213> ORGANISM: Artificial Sequence
<220> FEATURE:
<223> OTHER INFORMATION: SNAI1 Forward primer

<400> SEQUENCE: 15
gaccccaatc ggaagcctaa                                              20

<210> SEQ ID NO 16
<211> LENGTH: 17
<212> TYPE: DNA
<213> ORGANISM: Artificial Sequence
<220> FEATURE:
<223> OTHER INFORMATION: SNAI1 Reverse Primer

<400> SEQUENCE: 16
gcggtggggt tgaggat                                                 17
```

```
<210> SEQ ID NO 17
<211> LENGTH: 20
<212> TYPE: DNA
<213> ORGANISM: Artificial Sequence
<220> FEATURE:
<223> OTHER INFORMATION: VIM Forward primer

<400> SEQUENCE: 17
gatgtttcca agcctgacct                                                   20

<210> SEQ ID NO 18
<211> LENGTH: 19
<212> TYPE: DNA
<213> ORGANISM: Artificial Sequence
<220> FEATURE:
<223> OTHER INFORMATION: VIM Reverse primer

<400> SEQUENCE: 18
cagtggactc ctgctttgc                                                    19

<210> SEQ ID NO 19
<211> LENGTH: 21
<212> TYPE: DNA
<213> ORGANISM: Artificial Sequence
<220> FEATURE:
<223> OTHER INFORMATION: SNAI2 Forward primer

<400> SEQUENCE: 19
agcgaactgg acacacatac a                                                 21

<210> SEQ ID NO 20
<211> LENGTH: 20
<212> TYPE: DNA
<213> ORGANISM: Artificial Sequence
<220> FEATURE:
<223> OTHER INFORMATION: SNAI2 Reverse primer

<400> SEQUENCE: 20
aggaggtgtc agatggagga                                                   20

<210> SEQ ID NO 21
<211> LENGTH: 19
<212> TYPE: DNA
<213> ORGANISM: Artificial Sequence
<220> FEATURE:
<223> OTHER INFORMATION: FOXC2 Forward primer

<400> SEQUENCE: 21
cgcctaagga cctggtgaa                                                    19

<210> SEQ ID NO 22
<211> LENGTH: 20
<212> TYPE: DNA
<213> ORGANISM: Artificial Sequence
<220> FEATURE:
<223> OTHER INFORMATION: FOXC2 Reverse primer

<400> SEQUENCE: 22
gaagcggtcc atgatgaact                                                   20

<210> SEQ ID NO 23
<211> LENGTH: 20
<212> TYPE: DNA
<213> ORGANISM: Artificial Sequence
<220> FEATURE:
<223> OTHER INFORMATION: FOXC1 Forward primer
```

```
<400> SEQUENCE: 23
cacaccctca aagccgaact                                               20

<210> SEQ ID NO 24
<211> LENGTH: 20
<212> TYPE: DNA
<213> ORGANISM: Artificial Sequence
<220> FEATURE:
<223> OTHER INFORMATION: FOXC1 Reverse primer

<400> SEQUENCE: 24
aaagtggagg tggctctgaa                                               20

<210> SEQ ID NO 25
<211> LENGTH: 17
<212> TYPE: DNA
<213> ORGANISM: Artificial Sequence
<220> FEATURE:
<223> OTHER INFORMATION: CDH1 Forward primer

<400> SEQUENCE: 25
gagagaggcc gcgtcct                                                  17

<210> SEQ ID NO 26
<211> LENGTH: 22
<212> TYPE: DNA
<213> ORGANISM: Artificial Sequence
<220> FEATURE:
<223> OTHER INFORMATION: CDH1 Reverse primer

<400> SEQUENCE: 26 ggcctttga ctgtaatcac ac                                             22

<210> SEQ ID NO 27
<211> LENGTH: 20
<212> TYPE: DNA
<213> ORGANISM: Artificial Sequence
<220> FEATURE:
<223> OTHER INFORMATION: KRT18(1) Forward primer

<400> SEQUENCE: 27
tgctcaccac acagtctgat                                               20

<210> SEQ ID NO 28
<211> LENGTH: 20
<212> TYPE: DNA
<213> ORGANISM: Artificial Sequence
<220> FEATURE:
<223> OTHER INFORMATION: KRT18(1) Reverse primer

<400> SEQUENCE: 28
cactttgcca tccactagcc                                               20

<210> SEQ ID NO 29
<211> LENGTH: 20
<212> TYPE: DNA
<213> ORGANISM: Artificial Sequence
<220> FEATURE:
<223> OTHER INFORMATION: KRT8(2) Forward primer

<400> SEQUENCE: 29
aaggatgcca acgccaagtt                                               20

<210> SEQ ID NO 30
```

```
<211> LENGTH: 20
<212> TYPE: DNA
<213> ORGANISM: Artificial Sequence
<220> FEATURE:
<223> OTHER INFORMATION: KRT8(2) Reverse primer

<400> SEQUENCE: 30
ccgctggtgg tcttcgtatg                                                  20

<210> SEQ ID NO 31
<211> LENGTH: 20
<212> TYPE: DNA
<213> ORGANISM: Artificial Sequence
<220> FEATURE:
<223> OTHER INFORMATION: KRT19 Forward primer

<400> SEQUENCE: 31
cagccactac tacacgacca                                                  20

<210> SEQ ID NO 32
<211> LENGTH: 18
<212> TYPE: DNA
<213> ORGANISM: Artificial Sequence
<220> FEATURE:
<223> OTHER INFORMATION: KRT19 Reverse primer

<400> SEQUENCE: 32
cgttgatgtc ggcctcca                                                    18

<210> SEQ ID NO 33
<211> LENGTH: 17
<212> TYPE: DNA
<213> ORGANISM: Artificial Sequence
<220> FEATURE:
<223> OTHER INFORMATION: EPCAM Forward primer

<400> SEQUENCE: 33
gcaggtcctc gcgttcg                                                     17

<210> SEQ ID NO 34
<211> LENGTH: 22
<212> TYPE: DNA
<213> ORGANISM: Artificial Sequence
<220> FEATURE:
<223> OTHER INFORMATION: EPCAM Reverse primer

<400> SEQUENCE: 34
tctcccaagt tttgagccat tc                                               22

<210> SEQ ID NO 35
<211> LENGTH: 20
<212> TYPE: DNA
<213> ORGANISM: Artificial Sequence
<220> FEATURE:
<223> OTHER INFORMATION: TP53 exon 5(3) Forward

<400> SEQUENCE: 35
tgttcacttg tgccctgact                                                  20

<210> SEQ ID NO 36
<211> LENGTH: 20
<212> TYPE: DNA
<213> ORGANISM: Artificial Sequence
<220> FEATURE:
<223> OTHER INFORMATION: TP53 exon 5(3) Reverse primer

<400> SEQUENCE: 36
```
cagccctgtc gtctctccag                                                20

<210> SEQ ID NO 37
<211> LENGTH: 19
<212> TYPE: DNA
<213> ORGANISM: Artificial Sequence
<220> FEATURE:
<223> OTHER INFORMATION: TP53 exon 6(4) Forward primer

<400> SEQUENCE: 37
tggttgccca gggtcccca                                                 19

<210> SEQ ID NO 38
<211> LENGTH: 20
<212> TYPE: DNA
<213> ORGANISM: Artificial Sequence
<220> FEATURE:
<223> OTHER INFORMATION: TP53 exon 6(4) Reverse primer

<400> SEQUENCE: 38
tggagggcca ctgacaacca                                                20

<210> SEQ ID NO 39
<211> LENGTH: 20
<212> TYPE: DNA
<213> ORGANISM: Artificial Sequence
<220> FEATURE:
<223> OTHER INFORMATION: TP53 exon 7(5) Forward primer

<400> SEQUENCE: 39
cttgccacag gtctccccaa                                                20

<210> SEQ ID NO 40
<211> LENGTH: 20
<212> TYPE: DNA
<213> ORGANISM: Artificial Sequence
<220> FEATURE:
<223> OTHER INFORMATION: TP53 exon 7(5) Reverse primer

<400> SEQUENCE: 40
aggggtcaga ggcaagcaga                                                20

<210> SEQ ID NO 41
<211> LENGTH: 20
<212> TYPE: DNA
<213> ORGANISM: Artificial Sequence
<220> FEATURE:
<223> OTHER INFORMATION: TP53 exon 8(6) Forward primer

<400> SEQUENCE: 41
ttccttactg cctcttgctt                                                20

<210> SEQ ID NO 42
<211> LENGTH: 20
<212> TYPE: DNA
<213> ORGANISM: Artificial Sequence
<220> FEATURE:
<223> OTHER INFORMATION: TP53 exon 8(6) Reverse primer

<400> SEQUENCE: 42
aggcataact gcacccttgg                                                20

<210> SEQ ID NO 43
<211> LENGTH: 21
<212> TYPE: DNA

```
<213> ORGANISM: Artificial Sequence
<220> FEATURE:
<223> OTHER INFORMATION: BRAF exon 15(7) Forward primer

<400> SEQUENCE: 43
cataatgctt gctctgatag g                                    21

<210> SEQ ID NO 44
<211> LENGTH: 22
<212> TYPE: DNA
<213> ORGANISM: Artificial Sequence
<220> FEATURE:
<223> OTHER INFORMATION: BRAF exon 15(7) Reverse primer

<400> SEQUENCE: 44
ggccaaaaat ttaatcagtg ga                                   22

<210> SEQ ID NO 45
<211> LENGTH: 25
<212> TYPE: DNA
<213> ORGANISM: Artificial Sequence
<220> FEATURE:
<223> OTHER INFORMATION: KRAS exon 2(8) Forward primer

<400> SEQUENCE: 45
ttataaggcc tgctgaaaat gactg                                25

<210> SEQ ID NO 46
<211> LENGTH: 25
<212> TYPE: DNA
<213> ORGANISM: Artificial Sequence
<220> FEATURE:
<223> OTHER INFORMATION: KRAS exon 2(8) Reverse primer

<400> SEQUENCE: 46
tcatgaaaat ggtcagagaa acctt                                25

<210> SEQ ID NO 47
<211> LENGTH: 19
<212> TYPE: DNA
<213> ORGANISM: Artificial Sequence
<220> FEATURE:
<223> OTHER INFORMATION: EGFR Forward primer

<400> SEQUENCE: 47
gtcgggctct ggaggaaaa                                       19

<210> SEQ ID NO 48
<211> LENGTH: 22
<212> TYPE: DNA
<213> ORGANISM: Artificial Sequence
<220> FEATURE:
<223> OTHER INFORMATION: EGFR Reverse primer

<400> SEQUENCE: 48
ctctggaggc tgagaaaatg at                                   22

<210> SEQ ID NO 49
<211> LENGTH: 24
<212> TYPE: DNA
<213> ORGANISM: Artificial Sequence
<220> FEATURE:
<223> OTHER INFORMATION: PTPRC Forward primer

<400> SEQUENCE: 49
gacatcatca cctagcagtt catg                                 24
```

<210> SEQ ID NO 50
<211> LENGTH: 19
<212> TYPE: DNA
<213> ORGANISM: Artificial Sequence
<220> FEATURE:
<223> OTHER INFORMATION: PTPRC Reverse primer

<400> SEQUENCE: 50
cagtggggga aggtgttgg                                              19

<210> SEQ ID NO 51
<211> LENGTH: 19
<212> TYPE: DNA
<213> ORGANISM: Artificial Sequence
<220> FEATURE:
<223> OTHER INFORMATION: VWF Forward primer

<400> SEQUENCE: 51
acacaggggg accaaagag                                              19

<210> SEQ ID NO 52
<211> LENGTH: 19
<212> TYPE: DNA
<213> ORGANISM: Artificial Sequence
<220> FEATURE:
<223> OTHER INFORMATION: VWF Reverse primer

<400> SEQUENCE: 52
gagatgcccg ttcacacca                                              19

<210> SEQ ID NO 53
<211> LENGTH: 19
<212> TYPE: DNA
<213> ORGANISM: Artificial Sequence
<220> FEATURE:
<223> OTHER INFORMATION: PECAM1 Forward primer

<400> SEQUENCE: 53
tctcaacggt gacttgtgg                                              19

<210> SEQ ID NO 54
<211> LENGTH: 21
<212> TYPE: DNA
<213> ORGANISM: Artificial Sequence
<220> FEATURE:
<223> OTHER INFORMATION: PECAM1 Reverse primer

<400> SEQUENCE: 54
gttcttccca ttttgcaccg t                                           21

<210> SEQ ID NO 55
<211> LENGTH: 20
<212> TYPE: DNA
<213> ORGANISM: Artificial Sequence
<220> FEATURE:
<223> OTHER INFORMATION: COL1A1 Forward primer

<400> SEQUENCE: 55
tgttcagctt tgtggacctc                                             20

<210> SEQ ID NO 56
<211> LENGTH: 19
<212> TYPE: DNA
<213> ORGANISM: Artificial Sequence
<220> FEATURE:

<223> OTHER INFORMATION: COL1A1 Reverse primer

<400> SEQUENCE: 56
ggtttccaca cgtctcggt         19

<210> SEQ ID NO 57
<211> LENGTH: 21
<212> TYPE: DNA
<213> ORGANISM: Artificial Sequence
<220> FEATURE:
<223> OTHER INFORMATION: CD68 Forward primer

<400> SEQUENCE: 57
cattctttca ccagctgtcc a         21

<210> SEQ ID NO 58
<211> LENGTH: 15
<212> TYPE: DNA
<213> ORGANISM: Artificial Sequence
<220> FEATURE:
<223> OTHER INFORMATION: CD68 Reverse primer

<400> SEQUENCE: 58
gcaccagggc gagga         15

<210> SEQ ID NO 59
<211> LENGTH: 18
<212> TYPE: DNA
<213> ORGANISM: Artificial Sequence
<220> FEATURE:
<223> OTHER INFORMATION: MCAM Forward primer

<400> SEQUENCE: 59
ctcggtccca ggagtacc         18

<210> SEQ ID NO 60
<211> LENGTH: 21
<212> TYPE: DNA
<213> ORGANISM: Artificial Sequence
<220> FEATURE:
<223> OTHER INFORMATION: MCAM Reverse primer

<400> SEQUENCE: 60
tgtacaaacc actcgactcc a         21

<210> SEQ ID NO 61
<211> LENGTH: 20
<212> TYPE: DNA
<213> ORGANISM: Artificial Sequence
<220> FEATURE:
<223> OTHER INFORMATION: FCGR3A Forward primer

<400> SEQUENCE: 61
cccttgccag acttcagact         20

<210> SEQ ID NO 62
<211> LENGTH: 20
<212> TYPE: DNA
<213> ORGANISM: Artificial Sequence
<220> FEATURE:
<223> OTHER INFORMATION: FCGR3A Reverse primer

<400> SEQUENCE: 62
gggagatctt cagtccgcat         20

```
<210> SEQ ID NO 63
<211> LENGTH: 21
<212> TYPE: DNA
<213> ORGANISM: Artificial Sequence
<220> FEATURE:
<223> OTHER INFORMATION: GYPA Forward primer

<400> SEQUENCE: 63
ctagcaggct aaggtcagac a                                              21

<210> SEQ ID NO 64
<211> LENGTH: 20
<212> TYPE: DNA
<213> ORGANISM: Artificial Sequence
<220> FEATURE:
<223> OTHER INFORMATION: GYPA Reverse primer

<400> SEQUENCE: 64
gtgtcccgtt tgtgcgtatc                                                20

<210> SEQ ID NO 65
<211> LENGTH: 19
<212> TYPE: DNA
<213> ORGANISM: Artificial Sequence
<220> FEATURE:
<223> OTHER INFORMATION: ITGA2B Forward primer

<400> SEQUENCE: 65
cttctatgca ggccccaat                                                 19

<210> SEQ ID NO 66
<211> LENGTH: 22
<212> TYPE: DNA
<213> ORGANISM: Artificial Sequence
<220> FEATURE:
<223> OTHER INFORMATION: ITGA2B Reverse primer

<400> SEQUENCE: 66
agcctacatt tcgggtctca tc                                             22

<210> SEQ ID NO 67
<211> LENGTH: 21
<212> TYPE: DNA
<213> ORGANISM: Artificial Sequence
<220> FEATURE:
<223> OTHER INFORMATION: DCSTAMP Forward primer

<400> SEQUENCE: 67
ctcccgctga ataaggagga a                                              21

<210> SEQ ID NO 68
<211> LENGTH: 25
<212> TYPE: DNA
<213> ORGANISM: Artificial Sequence
<220> FEATURE:
<223> OTHER INFORMATION: DCSTAMP Reverse primer

<400> SEQUENCE: 68
tcttgagttc cttgtttctc tccgt                                          25

<210> SEQ ID NO 69
<211> LENGTH: 25
<212> TYPE: DNA
<213> ORGANISM: Artificial Sequence
<220> FEATURE:
<223> OTHER INFORMATION: CD34 Forward primer
```

<400> SEQUENCE: 69
ccttctgggt tcatgagtct tgaca    25

<210> SEQ ID NO 70
<211> LENGTH: 25
<212> TYPE: DNA
<213> ORGANISM: Artificial Sequence
<220> FEATURE:
<223> OTHER INFORMATION: CD34 Reverse primer

<400> SEQUENCE: 70
tgtcgtttct gtgatgtttg ttgtg    25

<210> SEQ ID NO 71
<211> LENGTH: 20
<212> TYPE: DNA
<213> ORGANISM: Artificial Sequence
<220> FEATURE:
<223> OTHER INFORMATION: ACTB Forward primer

<400> SEQUENCE: 71
ctggcaccac accttctaca    20

<210> SEQ ID NO 72
<211> LENGTH: 20
<212> TYPE: DNA
<213> ORGANISM: Artificial Sequence
<220> FEATURE:
<223> OTHER INFORMATION: ACTB Reverse primer

<400> SEQUENCE: 72
tagcacagcc tggatagcaa    20

<210> SEQ ID NO 73
<211> LENGTH: 23
<212> TYPE: DNA
<213> ORGANISM: Artificial Sequence
<220> FEATURE:
<223> OTHER INFORMATION: FOLH1 Forward primer

<400> SEQUENCE: 73
cggatattgt accacctttc agt    23

<210> SEQ ID NO 74
<211> LENGTH: 20
<212> TYPE: DNA
<213> ORGANISM: Artificial Sequence
<220> FEATURE:
<223> OTHER INFORMATION: FOLH1 Reverse primer

<400> SEQUENCE: 74
agcagggtcg gagtagagaa    20

<210> SEQ ID NO 75
<211> LENGTH: 22
<212> TYPE: DNA
<213> ORGANISM: Artificial Sequence
<220> FEATURE:
<223> OTHER INFORMATION: ENG Fowrard primer

<400> SEQUENCE: 75
gtgacggtga aggtggaact ga    22

<210> SEQ ID NO 76
<211> LENGTH: 20

```
<212> TYPE: DNA
<213> ORGANISM: Artificial Sequence
<220> FEATURE:
<223> OTHER INFORMATION: ENG Reverse primer

<400> SEQUENCE: 76
ttgaggtgtg tctgggagct                                                   20

<210> SEQ ID NO 77
<211> LENGTH: 23
<212> TYPE: DNA
<213> ORGANISM: Artificial Sequence
<220> FEATURE:
<223> OTHER INFORMATION: KDR Forward primer

<400> SEQUENCE: 77
gaaatgacac tggagcctac aag                                               23

<210> SEQ ID NO 78
<211> LENGTH: 21
<212> TYPE: DNA
<213> ORGANISM: Artificial Sequence
<220> FEATURE:
<223> OTHER INFORMATION: KDR Reverse primer

<400> SEQUENCE: 78
aatggacccg agacatggaa t                                                 21

<210> SEQ ID NO 79
<211> LENGTH: 22
<212> TYPE: DNA
<213> ORGANISM: Artificial Sequence
<220> FEATURE:
<223> OTHER INFORMATION: CDH5 Forward primer

<400> SEQUENCE: 79
gttcacgcat cggttgttca at                                                22

<210> SEQ ID NO 80
<211> LENGTH: 20
<212> TYPE: DNA
<213> ORGANISM: Artificial Sequence
<220> FEATURE:
<223> OTHER INFORMATION: CDH5 Reverse primer

<400> SEQUENCE: 80
gcctgcttct ctcggtccaa                                                   20

<210> SEQ ID NO 81
<211> LENGTH: 23
<212> TYPE: DNA
<213> ORGANISM: Artificial Sequence
<220> FEATURE:
<223> OTHER INFORMATION: TEK Forward primer

<400> SEQUENCE: 81
cttatttctg tgaagggcga gtt                                               23

<210> SEQ ID NO 82
<211> LENGTH: 22
<212> TYPE: DNA
<213> ORGANISM: Artificial Sequence
<220> FEATURE:
<223> OTHER INFORMATION: TEK Reverse primer

<400> SEQUENCE: 82
```
ctcccttgtc cacagtcata gt                                         22

<210> SEQ ID NO 83
<211> LENGTH: 25
<212> TYPE: DNA
<213> ORGANISM: Artificial Sequence
<220> FEATURE:
<223> OTHER INFORMATION: ANGPT2 Forward primer

<400> SEQUENCE: 83
aacactccct ctcgacaaac aaatt                                      25

<210> SEQ ID NO 84
<211> LENGTH: 24
<212> TYPE: DNA
<213> ORGANISM: Artificial Sequence
<220> FEATURE:
<223> OTHER INFORMATION: ANGPT2 Reverse primer

<400> SEQUENCE: 84
ctgtagttgg atgatgtgct tgtc                                       24

<210> SEQ ID NO 85
<211> LENGTH: 20
<212> TYPE: DNA
<213> ORGANISM: Artificial Sequence
<220> FEATURE:
<223> OTHER INFORMATION: HPRT1 Forward primer

<400> SEQUENCE: 85
tgaccagtca acaggggaca                                            20

<210> SEQ ID NO 86
<211> LENGTH: 21
<212> TYPE: DNA
<213> ORGANISM: Artificial Sequence
<220> FEATURE:
<223> OTHER INFORMATION: HPRT1 Reverse primer

<400> SEQUENCE: 86
ggtccttttc accagcaagc t                                          21

<210> SEQ ID NO 87
<211> LENGTH: 20
<212> TYPE: DNA
<213> ORGANISM: Artificial Sequence
<220> FEATURE:
<223> OTHER INFORMATION: UBC Forward primer

<400> SEQUENCE: 87
tcggccttag aacccagta                                             20

<210> SEQ ID NO 88
<211> LENGTH: 23
<212> TYPE: DNA
<213> ORGANISM: Artificial Sequence
<220> FEATURE:
<223> OTHER INFORMATION: UBC Reverse primer

<400> SEQUENCE: 88
acgaagatct gcattgtcaa gtg                                        23

<210> SEQ ID NO 89
<211> LENGTH: 24
<212> TYPE: DNA
<213> ORGANISM: Artificial Sequence

```
<220> FEATURE:
<223> OTHER INFORMATION: CEACAM5 (Reverse primer on exon junction)
      Forward primer

<400> SEQUENCE: 89
tgtggtgggt aaacaatcag agcc                                          24

<210> SEQ ID NO 90
<211> LENGTH: 20
<212> TYPE: DNA
<213> ORGANISM: Artificial Sequence
<220> FEATURE:
<223> OTHER INFORMATION: CDX2 (Reverse primer on exon junction) Forward
      primer

<400> SEQUENCE: 90
cggcggaacc tgtgcgagtg                                               20

<210> SEQ ID NO 91
<211> LENGTH: 23
<212> TYPE: DNA
<213> ORGANISM: Artificial Sequence
<220> FEATURE:
<223> OTHER INFORMATION: KRT20 (2141 bp intron in DNA sequence) Forward
      Primer

<400> SEQUENCE: 91
gcgactacag tgcatattac aga                                           23

<210> SEQ ID NO 92
<211> LENGTH: 20
<212> TYPE: DNA
<213> ORGANISM: Artificial Sequence
<220> FEATURE:
<223> OTHER INFORMATION: FN1 (830 bp intron in DNA sequence) Forward
      Primer

<400> SEQUENCE: 92
caagcccggt tgttatgaca                                               20

<210> SEQ ID NO 93
<211> LENGTH: 23
<212> TYPE: DNA
<213> ORGANISM: Artificial Sequence
<220> FEATURE:
<223> OTHER INFORMATION: CDH2 (1690 bp intron in DNA sequence) Forward
      Primer

<400> SEQUENCE: 93
aagttcctga tatatgccca aga                                           23

<210> SEQ ID NO 94
<211> LENGTH: 23
<212> TYPE: DNA
<213> ORGANISM: Artificial Sequence
<220> FEATURE:
<223> OTHER INFORMATION: SERPINE1 (1148 bp intron in DNA sequence)
      Forward Primer

<400> SEQUENCE: 94
agaacttcag gatgcagatg tct                                           23

<210> SEQ ID NO 95
<211> LENGTH: 24
<212> TYPE: DNA
<213> ORGANISM: Artificial Sequence
<220> FEATURE:
```

```
<223> OTHER INFORMATION: TWIST1 (Forward primer on exon junction)
      Forward Primer

<400> SEQUENCE: 95
ccagagaagg agaaaatgga cagt                                            24

<210> SEQ ID NO 96
<211> LENGTH: 20
<212> TYPE: DNA
<213> ORGANISM: Artificial Sequence
<220> FEATURE:
<223> OTHER INFORMATION: SNAI1 (682bp intron in DNA sequence) Reverse
      Primer

<400> SEQUENCE: 96
gtagggctgc tggaaggtaa                                                 20

<210> SEQ ID NO 97
<211> LENGTH: 21
<212> TYPE: DNA
<213> ORGANISM: Artificial Sequence
<220> FEATURE:
<223> OTHER INFORMATION: VIM (761 bp intron in DNA sequence) Reverse
      Primer

<400> SEQUENCE: 97
tgtaccattc ttctgcctcc t                                               21

<210> SEQ ID NO 98
<211> LENGTH: 20
<212> TYPE: DNA
<213> ORGANISM: Artificial Sequence
<220> FEATURE:
<223> OTHER INFORMATION: SNAI2 (745 bp intron in DNA sequence) Reverse
      Primer

<400> SEQUENCE: 98
gtggaatgga gcagcggtag                                                 20

<210> SEQ ID NO 99
<211> LENGTH: 19
<212> TYPE: DNA
<213> ORGANISM: Artificial Sequence
<220> FEATURE:
<223> OTHER INFORMATION: FOXC2 (NA (single exon coding gene)) Forward
      Primer

<400> SEQUENCE: 99
gctcatcacc atggccatc                                                  19

<210> SEQ ID NO 100
<211> LENGTH: 22
<212> TYPE: DNA
<213> ORGANISM: Artificial Sequence
<220> FEATURE:
<223> OTHER INFORMATION: FOXC1 (NA (single exon coding gene)) Reverse
      Primer

<400> SEQUENCE: 100
gagggatatt ctgttcgctg gt                                              22

<210> SEQ ID NO 101
<211> LENGTH: 24
<212> TYPE: DNA
<213> ORGANISM: Artificial Sequence
<220> FEATURE:
<223> OTHER INFORMATION: CDH1 (63258bp intron in DNA sequence) Forward
```

```
          Primer

<400> SEQUENCE: 101
ggcagagtga attttgaaga ttgc                                            24

<210> SEQ ID NO 102
<211> LENGTH: 20
<212> TYPE: DNA
<213> ORGANISM: Artificial Sequence
<220> FEATURE:
<223> OTHER INFORMATION: KRT18 (641 bp introns in DNA sequence) Forward
      Primer

<400> SEQUENCE: 102
tggaggaccg ctacgcccta                                                 20

<210> SEQ ID NO 103
<211> LENGTH: 20
<212> TYPE: DNA
<213> ORGANISM: Artificial Sequence
<220> FEATURE:
<223> OTHER INFORMATION: KRT18 (641 bp introns in DNA sequence) Reverse
      Primer

<400> SEQUENCE: 103
ccaaggcatc accaagacta                                                 20

<210> SEQ ID NO 104
<211> LENGTH: 17
<212> TYPE: DNA
<213> ORGANISM: Artificial Sequence
<220> FEATURE:
<223> OTHER INFORMATION: KRT8 (159 bp intron in DNA sequence) Forward
      Primer

<400> SEQUENCE: 104
gctggagggc gaggaga                                                    17

<210> SEQ ID NO 105
<211> LENGTH: 20
<212> TYPE: DNA
<213> ORGANISM: Artificial Sequence
<220> FEATURE:
<223> OTHER INFORMATION: KRT19 (2745 bp intron in DNA sequence) Forward
      Primer

<400> SEQUENCE: 105
tgcgggacaa gattcttggt                                                 20

<210> SEQ ID NO 106
<211> LENGTH: 20
<212> TYPE: DNA
<213> ORGANISM: Artificial Sequence
<220> FEATURE:
<223> OTHER INFORMATION: EPCAM (4118 bp intron in DNA sequence) Forward
      Primer

<400> SEQUENCE: 106
ccgcagctca ggaagaatgt                                                 20

<210> SEQ ID NO 107
<211> LENGTH: 20
<212> TYPE: DNA
<213> ORGANISM: Artificial Sequence
<220> FEATURE:
<223> OTHER INFORMATION: TP53 exon 5 (Primers on intronic sequences)
      Forward Primer
```

<210> SEQ ID NO 108
<211> LENGTH: 20
<212> TYPE: DNA
<213> ORGANISM: Artificial Sequence
<220> FEATURE:
<223> OTHER INFORMATION: TP53 exon 6 (Primers on intronic sequences) Forward Primer

<400> SEQUENCE: 108
gcctctgatt cctcactgat                                          20

<210> SEQ ID NO 109
<211> LENGTH: 20
<212> TYPE: DNA
<213> ORGANISM: Artificial Sequence
<220> FEATURE:
<223> OTHER INFORMATION: TP53 exon 6 (Primers on intronic sequences) Reverse Primer

<400> SEQUENCE: 109
ttaacccctc ctcccagaga                                          20

<210> SEQ ID NO 110
<211> LENGTH: 21
<212> TYPE: DNA
<213> ORGANISM: Artificial Sequence
<220> FEATURE:
<223> OTHER INFORMATION: TP53 exon 7 (Primers on intronic sequences) Forward Primer

<400> SEQUENCE: 110
aaggcgcact ggcctcatct t                                        21

<210> SEQ ID NO 111
<211> LENGTH: 21
<212> TYPE: DNA
<213> ORGANISM: Artificial Sequence
<220> FEATURE:
<223> OTHER INFORMATION: TP53 exon 8 (Primers on intronic sequences) Forward Primer

<400> SEQUENCE: 111
agtggtaatc tactgggacg g                                        21

<210> SEQ ID NO 112
<211> LENGTH: 20
<212> TYPE: DNA
<213> ORGANISM: Artificial Sequence
<220> FEATURE:
<223> OTHER INFORMATION: TP53 exon 8 (Primers on intronic sequences) Reverse Primer

<400> SEQUENCE: 112
acctcgctta gtgctccctg                                          20

<210> SEQ ID NO 113
<211> LENGTH: 20
<212> TYPE: DNA
<213> ORGANISM: Artificial Sequence
<220> FEATURE:
<223> OTHER INFORMATION: BRAF exon 15 (Primers on intronic sequences) Reverse Primer

<400> SEQUENCE: 107
ttcaactctg tctccttcct                                          20

<400> SEQUENCE: 113
tagcctcaat tcttaccatc                                                20

<210> SEQ ID NO 114
<211> LENGTH: 25
<212> TYPE: DNA
<213> ORGANISM: Artificial Sequence
<220> FEATURE:
<223> OTHER INFORMATION: KRAS exon 2 (Primers on intronic sequences)
      Reverse Primer

<400> SEQUENCE: 114
caaagaatgg tcctgcacca gtaat                                          25

<210> SEQ ID NO 115
<211> LENGTH: 22
<212> TYPE: DNA
<213> ORGANISM: Artificial Sequence
<220> FEATURE:
<223> OTHER INFORMATION: EGFR (122920 bp intron in DNA sequence) Forward
      Primer

<400> SEQUENCE: 115
tctggaggaa aagaaagttt gc                                             22

<210> SEQ ID NO 116
<211> LENGTH: 21
<212> TYPE: DNA
<213> ORGANISM: Artificial Sequence
<220> FEATURE:
<223> OTHER INFORMATION: PTPRC (53092 bp intron in DNA sequence) Forward
      Primer

<400> SEQUENCE: 116
caacagtgga gaaaggacgc a                                              21

<210> SEQ ID NO 117
<211> LENGTH: 20
<212> TYPE: DNA
<213> ORGANISM: Artificial Sequence
<220> FEATURE:
<223> OTHER INFORMATION: VWF (Forward primer on exon junction) Forward
      Primer

<400> SEQUENCE: 117
tgcctccaaa gggctgtatc                                                20

<210> SEQ ID NO 118
<211> LENGTH: 21
<212> TYPE: DNA
<213> ORGANISM: Artificial Sequence
<220> FEATURE:
<223> OTHER INFORMATION: PECAM1 (12457 bp intron in DNA sequence) Foward
      Primer

<400> SEQUENCE: 118
cagtcttcac tctcaggatg c                                              21

<210> SEQ ID NO 119
<211> LENGTH: 20
<212> TYPE: DNA
<213> ORGANISM: Artificial Sequence
<220> FEATURE:
<223> OTHER INFORMATION: COL1A1 (1463 bp intron in DNA sequence) Reverse
      Primer

<400> SEQUENCE: 119
gtgggatgtc ttcgtcttgg                                           20

<210> SEQ ID NO 120
<211> LENGTH: 20
<212> TYPE: DNA
<213> ORGANISM: Artificial Sequence
<220> FEATURE:
<223> OTHER INFORMATION: CD68 (311 bp intron in DNA sequence) Forward
      Primer

<400> SEQUENCE: 120
aaagtttctc ctgccccagt                                           20

<210> SEQ ID NO 121
<211> LENGTH: 22
<212> TYPE: DNA
<213> ORGANISM: Artificial Sequence
<220> FEATURE:
<223> OTHER INFORMATION: MCAM (1724 bp intron in DNA sequence) Reverse
      Primer

<400> SEQUENCE: 121
cggccattct tgtaccagat ga                                        22

<210> SEQ ID NO 122
<211> LENGTH: 17
<212> TYPE: DNA
<213> ORGANISM: Artificial Sequence
<220> FEATURE:
<223> OTHER INFORMATION: FCGR3A (Reverse primer on exon junction &
      intron in DNA seq) Reverse Primer

<400> SEQUENCE: 122
tttccccagc ccctcca                                              17

<210> SEQ ID NO 123
<211> LENGTH: 21
<212> TYPE: DNA
<213> ORGANISM: Artificial Sequence
<220> FEATURE:
<223> OTHER INFORMATION: GYPA (20010 bp introns in DNA sequence) Forward
      Primer

<400> SEQUENCE: 123
caggaaccag ctcatgatct c                                         21

<210> SEQ ID NO 124
<211> LENGTH: 16
<212> TYPE: DNA
<213> ORGANISM: Artificial Sequence
<220> FEATURE:
<223> OTHER INFORMATION: ITGA2B (3242 bp intron in DNA sequence) Forward
      Primer

<400> SEQUENCE: 124
ggcggcgtgt tcctgt                                               16

<210> SEQ ID NO 125
<211> LENGTH: 20
<212> TYPE: DNA
<213> ORGANISM: Artificial Sequence
<220> FEATURE:
<223> OTHER INFORMATION: DCSTAMP (Reverse primer on exon junction)
      Forward Primer

<400> SEQUENCE: 125

```
acctggggct gttttcctc                                                  20
```

<210> SEQ ID NO 126
<211> LENGTH: 22
<212> TYPE: DNA
<213> ORGANISM: Artificial Sequence
<220> FEATURE:
<223> OTHER INFORMATION: CD34 (Forward and reverse primers on exon
      junction) Forward Primer

<400> SEQUENCE: 126

```
ctaccccaga gttacctacc ca                                              22
```

<210> SEQ ID NO 127
<211> LENGTH: 20
<212> TYPE: DNA
<213> ORGANISM: Artificial Sequence
<220> FEATURE:
<223> OTHER INFORMATION: FOLH1 (6811 bp intron in DNA sequence) Forward
      Primer

<400> SEQUENCE: 127

```
ccagagggcg atctagtgta                                                 20
```

<210> SEQ ID NO 128
<211> LENGTH: 24
<212> TYPE: DNA
<213> ORGANISM: Artificial Sequence
<220> FEATURE:
<223> OTHER INFORMATION: ENG (256 bp intron in DNA sequence) Reverse
      Primer

<400> SEQUENCE: 128

```
agtattctcc agtggtccag atct                                            24
```

<210> SEQ ID NO 129
<211> LENGTH: 21
<212> TYPE: DNA
<213> ORGANISM: Artificial Sequence
<220> FEATURE:
<223> OTHER INFORMATION: KDR (3192 bp intron in DNA sequence) Reverse
      Primer

<400> SEQUENCE: 129

```
tgttggtcac taacagaagc a                                               21
```

<210> SEQ ID NO 130
<211> LENGTH: 20
<212> TYPE: DNA
<213> ORGANISM: Artificial Sequence
<220> FEATURE:
<223> OTHER INFORMATION: CDH5 (2143 bp intron in DNA sequence) Forward
      Primer

<400> SEQUENCE: 130

```
cacgcctctg tcatgtacca                                                 20
```

<210> SEQ ID NO 131
<211> LENGTH: 21
<212> TYPE: DNA
<213> ORGANISM: Artificial Sequence
<220> FEATURE:
<223> OTHER INFORMATION: TEK (10352 bp intron in DNA sequence) Reverse
      Primer

<400> SEQUENCE: 131

```
gtagctggta ggaaggaagc t                                               21
```

<210> SEQ ID NO 132
<211> LENGTH: 24
<212> TYPE: DNA
<213> ORGANISM: Artificial Sequence
<220> FEATURE:
<223> OTHER INFORMATION: ANGPT2 (6144 bp intron in DNA sequence) Forward
      Primer

<400> SEQUENCE: 132
ggaccagacc agtgaaataa acaa                                              24

<210> SEQ ID NO 133
<211> LENGTH: 21
<212> TYPE: DNA
<213> ORGANISM: Artificial Sequence
<220> FEATURE:
<223> OTHER INFORMATION: HPRT1 (Reverse primer on exon junction &
      introns in DNA seq) Forward Primer

<400> SEQUENCE: 133
tgacactggc aaaacaatgc a                                                 21

<210> SEQ ID NO 134
<211> LENGTH: 20
<212> TYPE: DNA
<213> ORGANISM: Artificial Sequence
<220> FEATURE:
<223> OTHER INFORMATION: UBC (Reverse primer on exon junction) Forward
      Primer

<400> SEQUENCE: 134
aaagtagtcc cttctcggcg                                                   20

<210> SEQ ID NO 135
<211> LENGTH: 25
<212> TYPE: DNA
<213> ORGANISM: Artificial Sequence
<220> FEATURE:
<223> OTHER INFORMATION: Primers for KRAS exon 2 sequencing - Forward
      primer

<400> SEQUENCE: 135
tttgtattaa aaggtactgg tggag                                             25

<210> SEQ ID NO 136
<211> LENGTH: 25
<212> TYPE: DNA
<213> ORGANISM: Artificial Sequence
<220> FEATURE:
<223> OTHER INFORMATION: Primers for KRAS exon 2 sequencing - Reverse
      primer

<400> SEQUENCE: 136
cctttatctg tatcaaagaa tggtc                                             25

<210> SEQ ID NO 137
<211> LENGTH: 25
<212> TYPE: DNA
<213> ORGANISM: Artificial Sequence
<220> FEATURE:
<223> OTHER INFORMATION: CD45 primer (Forward Primer)

<400> SEQUENCE: 137
aagacaacag tggagaaagg acgca                                             25

```
<210> SEQ ID NO 138
<211> LENGTH: 22
<212> TYPE: DNA
<213> ORGANISM: Artificial Sequence
<220> FEATURE:
<223> OTHER INFORMATION: CD45 primer (Reverse Primer)

<400> SEQUENCE: 138
cagtggggga aggtgttggg ct                                            22
```

SINGLE CELL RNA AND MUTATIONAL ANALYSIS PCR (SCRM-PCR): A METHOD FOR SIMULTANEOUS ANALYSIS OF DNA AND RNA AT THE SINGLE-CELL LEVEL

CROSS-REFERENCE TO RELATED APPLICATIONS

This patent application is a U.S. National Phase application under 35 U.S.C. § 371 of International Application No. PCT/SG2016/050026, filed on Jan. 20, 2016, entitled SINGLE CELL RNA AND MUTATIONAL ANALYSIS PCR (SCRM-PCR): A METHOD FOR SIMULTANEOUS ANALYSIS OF DNA AND RNA AT THE SINGLE-CELL LEVEL, which claims the benefit of priority of Singapore Patent Application No. 10201500472R, filed 21 Jan. 2015, the contents of it being hereby incorporated by reference in its entirety for all purposes.

This patent application incorporates by reference the material (i.e., Sequence Listing) in the ASCII text file named Sequence_Listing.txt, created on Jan. 21, 2016, having a file size of 28.1 kilobytes.

TECHNICAL FIELD

The present invention generally relates to polymerase chain reaction (PCR). In particular, the present invention relates to a method to simultaneously analyse RNA and DNA.

BACKGROUND ART

The polymerase chain reaction (PCR) technology, developed by Kary Mullis in 1983, provides a method to rapidly amplify small amounts of a particular target DNA. The amplified DNA can be used to facilitate analysis for the presence of DNA sequence variation, mutations, restriction enzyme cleavage or ligation of oligonucleotide pairs. The PCR has become a common and often indispensable tool in medical and biological research laboratories in a wide variety of applications.

Some of these applications have increasingly pointed to a need to link specific DNA profiles with its gene expression. For example, it has become increasingly useful to determine a mutation(s) in a cancer cell circulating in the bloodstream and linking this specific DNA profile with its gene expression to determine the type and origin of the cell in order to facilitate diagnosis, prognosis, prevention and treatment of various human cancers. One problem with such analysis of clinical samples or other samples such as forensic samples, is that the samples often contain a low number of cells (such as 1-100 cells), or the target nucleic acids are present in very limited amounts.

In the field of next generation sequencing, such as in RNA sequencing (RNA-seq), data and findings derived from large-scale transcriptomics often need to be verified by targeted assays. However, DNA sequences derived from RNA-seq data are often prone to errors due to lack of proofreading activity in reverse transcriptases. This is particularly problematic where the RNA-seq experiments are performed on a low number of cells.

Accordingly, there is a need to provide a method to simultaneously analyse RNA and DNA from a single cell or limited amounts of nucleic acids that overcomes, or at least ameliorates one or more of the disadvantages described above.

There is a need to provide such a method in a cost-effective way, with minimum procedural steps.

SUMMARY OF INVENTION

In a first aspect, there is provided a method of simultaneously analyzing RNA and DNA in a sample, the method comprising the steps of:
 (a) contacting the sample with a reverse primer from a first primer pair, the reverse primer from the first primer pair being directed to a target RNA region, and a reverse transcriptase to effect reverse transcription of the RNA into cDNA;
 (b) subsequently contacting the sample with:
  (i) a forward primer from the first primer pair, the forward primer from the first primer pair being directed to a target cDNA region,
  (ii) a reverse primer and a forward primer from a second primer pair, the reverse primer and forward primer from the second primer pair being directed to a target DNA region, and
  (iii) a DNA polymerase
   to simultaneously amplify the target cDNA region and the target DNA region; and
 (c) analyzing the amplified target cDNA region and/or the amplified target DNA region.

One embodiment of the method of the first aspect further comprises the step of subjecting the sample from step (b) to a semi-nested PCR using the reverse primer in step (a) or the forward primer in step (b)(i), and a nested primer that binds within the amplified target cDNA region.

In a second aspect, there is provided a method of simultaneously analyzing RNA and DNA in a sample, the method comprising the steps of:
 (a) lysing a cell in the sample;
 (b) contacting the lysed cell sample with a reverse primer from a first primer pair, the reverse primer from the first primer pair being directed to a target RNA region, and a reverse transcriptase to effect reverse transcription of the RNA into cDNA;
 (c) subsequently contacting the lysed cell sample with:
  (i) a forward primer from the first primer pair, the forward primer from the first primer pair being directed to a target cDNA region,
  (ii) a reverse primer and a forward primer from a second primer pair, the reverse primer and forward primer from the second primer pair being directed to a target DNA region, and
  (iii) a DNA polymerase
   to simultaneously amplify the target cDNA region and the target DNA region in a pre-amplification step;
 (d) subjecting the sample from step (c) to a semi-nested PCR using the reverse primer in step (b) or the forward primer in step (c)(i), a nested primer that binds within the pre-amplified target cDNA region, and a DNA polymerase to further amplify the target cDNA region, and/or subjecting the sample from step (c) to a nested PCR using a nested primer pair that binds within the pre-amplified target DNA region and a DNA polymerase to further amplify the target DNA region; and
 (e) analyzing the further amplified target cDNA region and/or the further amplified target DNA region.

In a third aspect, there is provided use of the method according to the first or second aspect for determining the DNA profile and/or the gene expression profile of a single cell or a plurality of cells, or cell-free RNA and/or DNA derived from a single cell or a plurality of cells.

In a fourth aspect, there is provided use of the method according to the first or second aspect for validation of large-scale transcriptomics data sets.

In a fifth aspect, there is provided a kit for performing the method according to the first or second aspect, or for use according to the third or fourth aspect, wherein the kit comprises:

(a) a primer selected from the group consisting of:
   i. the reverse primer of step (a) of the method of the first aspect or step (b) of the method of the second aspect,
   ii. the forward primer of step (b)(i) of the method of the first aspect or step (c)(i) of the method of the second aspect,
   iii. the primer pair of step (h)(ii) of the method of the first aspect or step (c)(ii) of the method of the second aspect, and
   iv. the nested primer and nested primer pair of the method of the first aspect or step (d) of the method of the second aspect;

(b) one or more reagents, selected from the group consisting of:
   i. a reverse transcriptase and one or more suitable reaction buffers for the reverse transcription in step (a) of the method of the first aspect or step (b) of the method of the second aspect,
   ii. a DNA polymerase and one or more suitable reaction buffers for the amplification in step (b) or the semi-nested or nested PCR of the method of the first aspect, or step (c) or (d) of the method of the second aspect, and
   iii. one or more labelled or unlabelled deoxyribonucleotides selected from the group consisting of dATP, dCTP, dGTP, and dTTP or dUTP; and (c) instructions for performing the method according to the first or second aspect, or for use according to the third or fourth aspect.

BRIEF DESCRIPTION OF DRAWINGS

The invention will be better understood with reference to the detailed description when considered in conjunction with the non-limiting examples and the accompanying drawings, in which:

FIG. 7 shows that CTM are tumour-derived mature endothelial cells. (a) shows lineage inference from RNA-Seq data of single-CTM. Normalized odds ratios compare number of genes enriched for each sample (rows) and cell type (columns) over random enrichment. MEP, Megakaryocyte-erythroid progenitor. In (b), immunofluorescence studies confirm the endothelial lineage of CTM. Representative CTM stained for the indicated antibodies with internal controls for each staining. Inset mid panel, a CD45$^+$ WBC. Inset right panel, a CD41/CD42B$^+$ platelet aggregate. The Table indicates quantification of CTM positive or negative for the indicated immunofluorescence. (c) shows the results of the EPC clonogenic assay for CTM (n=5 patients). The scatter plot represents initial (x axis) and final (y axis) number of CTM (grey symbols) or HUVEC cells (black circles). Same grey symbols are technical replicates. HUVEC cells data are represented as mean±s.e.m. of technical replicates. One representative experiment of two is shown. (d) shows the rank correlation of CTM and tissues RNA Seq data by principal component analysis. (e) shows the ladder plot of CD31$^+$CD45$^-$ CTM counts 0-24 h before and 24-72 h after surgery. Lines connect data from the same patient. Two-tailed Wilcoxon signed-rank test, ***P=0.0006, effect size r=0.54. (f) shows FOLH1 expression for the indicated tissues, PBMCs, and CTM for individual patients. Bars represent means. In tissues, error bars are s.e.m. from independent datapoints (n=3 patients). (g) shows CD276 in normal, tumour tissues and in single-CTM from RNA-Seq data. (h) shows the microvessel density count in patients with low (≤10 CTM/2 ml) and high (>10 CTM/2 ml) CTM counts (n=17 patients). Arrows and dashed white lines indicate microvessel lumens in representative images. Two-tailed Wilcoxon-Mann-Whitney U test with Bonferroni correction, *P=0.03, effect size r=0.57, Â (95% CI)=2 (0.5–4.16). ns, not significant.

FIG. 8 shows that CTM are prevalent in CRC patients, mirror therapeutic intervention and indicate the presence of colorectal cancer in early stage treatment-naive patients. (a) is a case-control study of CTM in blood. CTM count for each healthy control (n=45) and CRC case (n=80) are shown. Two-tailed Wilcoxon-Mann-Whitney U test, *P=7.31×10$^{-15}$, effect size r=0.65, Â (95% CI)=4 (3–9). (b) shows association of CTM count with patients and tumour characteristics (n=80 CRC cases). Two-tailed Wilcoxon-Mann-Whitney U test with Bonferroni correction, P=0.0072, effect size r=0.34, Â (95% CI)=−6 (−13−(−1)). (c) shows the trend of CTM count during colorectal cancer sequence of treatment. Blood samples were collected independently at discrete time points: 1) Treatment-naive, 2) Post neoadjuvant therapy, 3) Post surgery, 4) Post adjuvant therapy, 5) Palliative therapy. Light grey boxes indicate the interquartile range (IQR), line across boxes indicates the median, dashed line indicates the interpolation of medians by spline function. Arrows indicate treatment events. n=80 CRC cases, two-tailed Wilcoxon-Mann-Whitney U test, ***P=0.0002, effect size r=0.41, Â (95% CI)=−7 (−15−(−2)). ND, not detected. Post operative samples shown in FIG. 7e are not included. (d) shows the ROC curve for treatment-naïve CRC patients versus healthy controls (n=89). Shaded area (light grey) represents the bootstrapped 95% CI. AUC (95% CI)=0.930 (0.880–0.980), effect size r=0.71. (e) Same as (d), but comparing early-stage CRC cases (≤IIA) with healthy controls (n=61). AUC (95% CI)=0.922 (0.846–0.999), effect size r=0.70. In (a), (d) and (e), 100% stacked bar charts indicate the percentage of positive (dark grey) and negative (light grey) samples for both healthy controls and CRC cases.

FIG. 9 illustrates a silicon microsieve, microfiltration device and its retrieval efficiency and purity. (a) shows a bright field composite image (left panel) and scanning electron micrographs (right panels) of silicon microsieve. (b) shows a microfiltration device with components. (c) shows a silicon microsieves allow efficient retrieval of captured cells. Capture efficiency of HCT 116 cells from the whole blood, indicating % of captured cells that can be retrieved for downstream assays (light grey bars) or cannot be retrieved (dark grey bars). Six independent experiments are shown. (d) shows the size distribution of SW620 (light grey line), (n=50). Median size of WBCs and CTCs isolated from colorectal, prostate and breast cancer patients respectively reported from Coumans, F et al, 2013. (c) shows contaminating nucleated cells in clinical samples using optimized protocol shown in FIGS. 5b and 5c (n=13). (f) shows the retrieval efficiency from additional cell lines using optimized protocol shown in FIGS. 5b and 5c. Bars represent mean±s.e.m.

DESCRIPTION OF EMBODIMENTS

Figure 1:
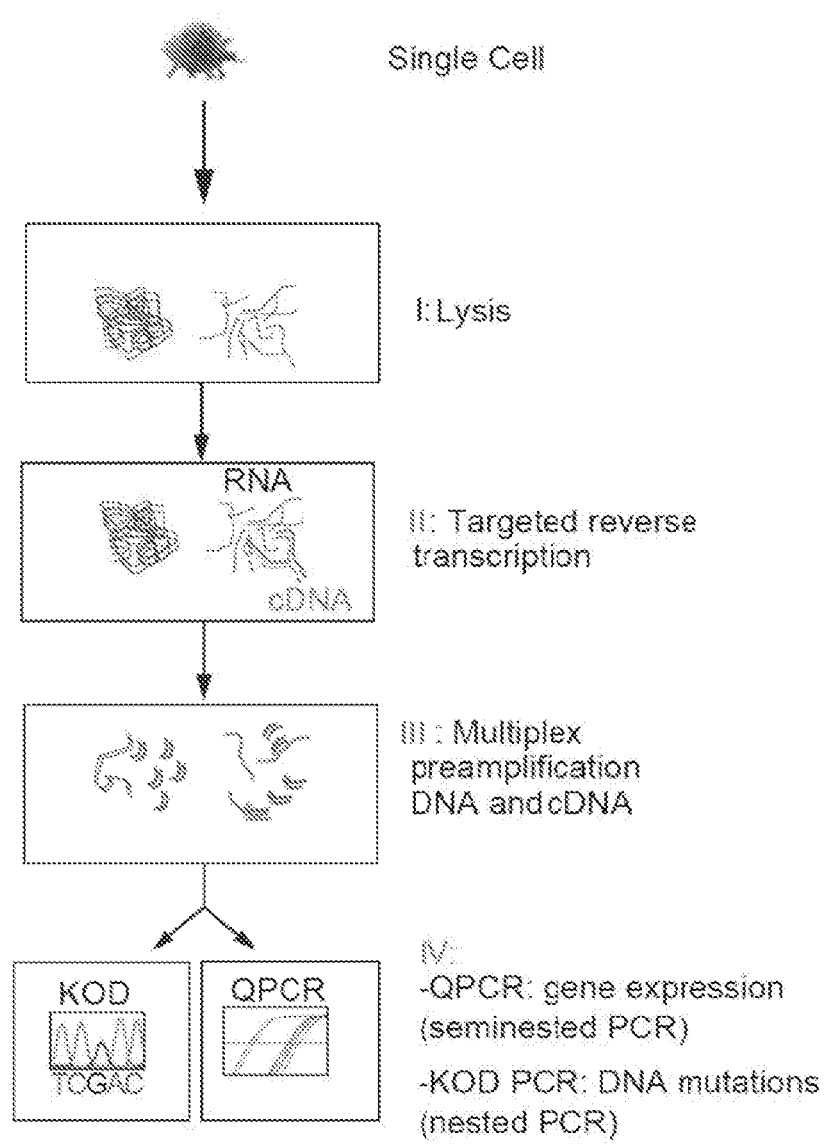
FIG. 1 provides an outline of the scrmPCR method of the disclosure. This method can be used to detect and quantify RNA transcripts and to sequence DNA from the same single cell. A schematic of the method is enclosed as FIG. 1 and is composed of the following steps:
1) Primer design: Primer sets are designed for semi-nested PCR (RNA transcripts) or nested PCR (genomic DNA). In some cases, primers were derived from the literature (Table 1). 2) Reverse transcription: Multiplex reverse primers are added to the lysed single cell, together with a reverse transcriptase enzyme (step II in FIG. 1). 3) Pre-amplification: Multiplex forward primers are added to the mixture, together with primers specific for DNA sequences and a pre-amplification step is performed using an optimized annealing temperature (Step III in FIG. 1). 4) Cleanup: Unused primers are removed by spin column or enzymatic digestion. 5) Dilution of the sample. 6) For RNA analysis, perform qPCR using a semi-nested approach, where a primer is designed to bind a sequence internal to the pre-amplified product and the other primer has been previously used during the pre-amplification step (step IV in FIG. 1) 7) For DNA analysis: PCR using a nested approach where both primers are designed to bind a sequence internal to the pre-amplified product (step IV in FIG. 1).

The method of the present disclosure can be used to simultaneously quantify RNA transcripts and sequence DNA regions from a single cell. The method can be applied to other samples, such as clinical or forensic samples, where nucleic acids are often present in very limited amounts, or to experimental samples containing a low number of cells, such as 2-100 cells.

In a first aspect, there is provided a method of simultaneously analyzing RNA and DNA in a sample, the method comprising the steps of:

(a) contacting the sample with a reverse primer from a first primer pair, the reverse primer from the first primer pair being directed to a target RNA region, and a reverse transcriptase to effect reverse transcription of the RNA into cDNA;

(b) subsequently contacting the sample with:

(i) a forward primer from the first primer pair, the forward primer from the first primer pair being directed to a target cDNA region, (ii) a reverse primer and a forward primer from a second primer pair, the reverse primer and forward primer from the second primer pair being directed to a target DNA region, and (iii) a DNA polymerase
to simultaneously amplify the target cDNA region and the target DNA region; and (c) analyzing the amplified target cDNA region and/or the amplified target DNA region.

Advantageously, the simultaneous amplification of the target cDNA region and the target DNA region in step (b) may form a pre-amplification step that increases the amount of cDNA and/or DNA as templates for further amplification of the target cDNA and/or target DNA regions prior to analysis. The target DNA region may be a target genomic DNA region.

By "primer" is meant an oligonucleotide which, when paired with a strand of DNA or RNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. For example, not all bases in the primer need to reflect the sequence of the template molecule to which the primer will hybridize—the primer need only contain sufficient complementary bases to enable the primer to hybridize to the template. The primer may include additional bases, for example in the form of a restriction enzyme recognition sequence at the 5' end, to facilitate cloning of the amplified DNA. A primer may also include mismatch bases at one or more positions, being bases that are not complementary to bases in the template, but rather are designed to incorporate changes into the DNA upon base extension or amplification.

The term "amplification" or "amplify" relates to the production of additional copies of a nucleic acid. Amplification may be carried out using polymerase chain reaction (PCR) technologies or other nucleic acid amplification technologies well known in the art.

"Primer pairs" can be used for amplification (and identification) of a nucleic acid, e.g., by the polymerase chain reaction (PCR). The "primer pair" may comprise a "forward primer" and a "reverse primer". In a PCR reaction, both strands of a double stranded DNA are amplified. The "forward primer" may bind to one strand of the DNA and allow the synthesis of a primer extension product from the 5' to 3' direction. The "reverse primer" may bind to the complementary strand of DNA, and also allow the synthesis of a primer extension product in the 5' to 3' direction of the complementary DNA strand. In a reverse transcription reaction, the "reverse primer" may bind to an RNA strand and allow the synthesis of a complementary DNA (cDNA) strand in a 5' to 3' direction of the cDNA strand in the presence of a reverse transcriptase enzyme. The "reverse primer" may subsequently be used together with a "forward primer" to amplify the synthesized cDNA strand. PCR primer pairs can be derived from a known sequence, for example, by using computer programs intended for that purpose such as Primer (Version 0.5, 1991, Whitehead Institute for Biomedical Research, Cambridge Mass.) and those used in the Examples disclosed herein (e.g. PrimerBLAST, Ncbi primer design tool, ensembl genome browser, Netprimer). Oligonucleotides for use as primers are selected using software known in the art for such purpose. For example, OLIGO 4.06 software is useful for the selection of PCR primer pairs of up to 30-100 nucleotides each, and for the analysis of oligonucleotides and larger polynucleotides of up to 5,000 nucleotides from an input polynucleotide sequence of up to 32 kilobases.

The methods and reagents for use in PCR amplification reactions, restriction enzyme digestion and subsequent fragment resolution, and nucleic acid sequencing are well known to those skilled in the art. In each case, suitable protocols and reagents will largely depend on individual circumstances. Guidance may be obtained from a variety of sources, such as for example Sambrook et al., Molecular Cloning A Laboratory Manual, Cold Spring Harbor, N.Y., 1989, and Ausubel et al., Current Protocols in Molecular Biology, Greene Publ. Assoc. and Wiley-Intersciences, 1992. A person skilled in the art would readily appreciate that various parameters of these procedures may be altered without affecting the ability to achieve the desired product. For example, in the case of PCR amplification, the salt concentration may be varied. Similarly, the amount of DNA used as a template may also be varied depending on the amount of DNA available or the optimal amount of template required for efficient amplification.

A skilled person would be able to understand that a "reverse transcriptase" is an enzyme that may be used to synthesise cDNA based on an RNA template. A skilled person would also understand that a "DNA polymerase" is an enzyme that can synthesise DNA molecules based on a DNA template.

By "contacting", a primer may be brought into physical association with a sample. This allows, for example, a primer pair to anneal with the DNA present in the sample, and subsequently amplify the DNA by PCR. This also allows a primer to anneal to an RNA strand present in the sample, to allow synthesis of cDNA using a reverse transcriptase enzyme as known to a person skilled in the art.

The method as defined herein allows one to "simultaneously" amplify RNA and DNA in a sample or single cell. The term "simultaneously" means to be able to amplify both RNA and DNA, present in the very same sample or single cell. It may also mean being able to analyze both RNA and DNA from the same sample or single cell.

To the inventor's knowledge, this is the first method that allows targeted analysis of both DNA mutations and RNA transcription in the same single cell. The method has undergone several optimization steps.

Figure 2:
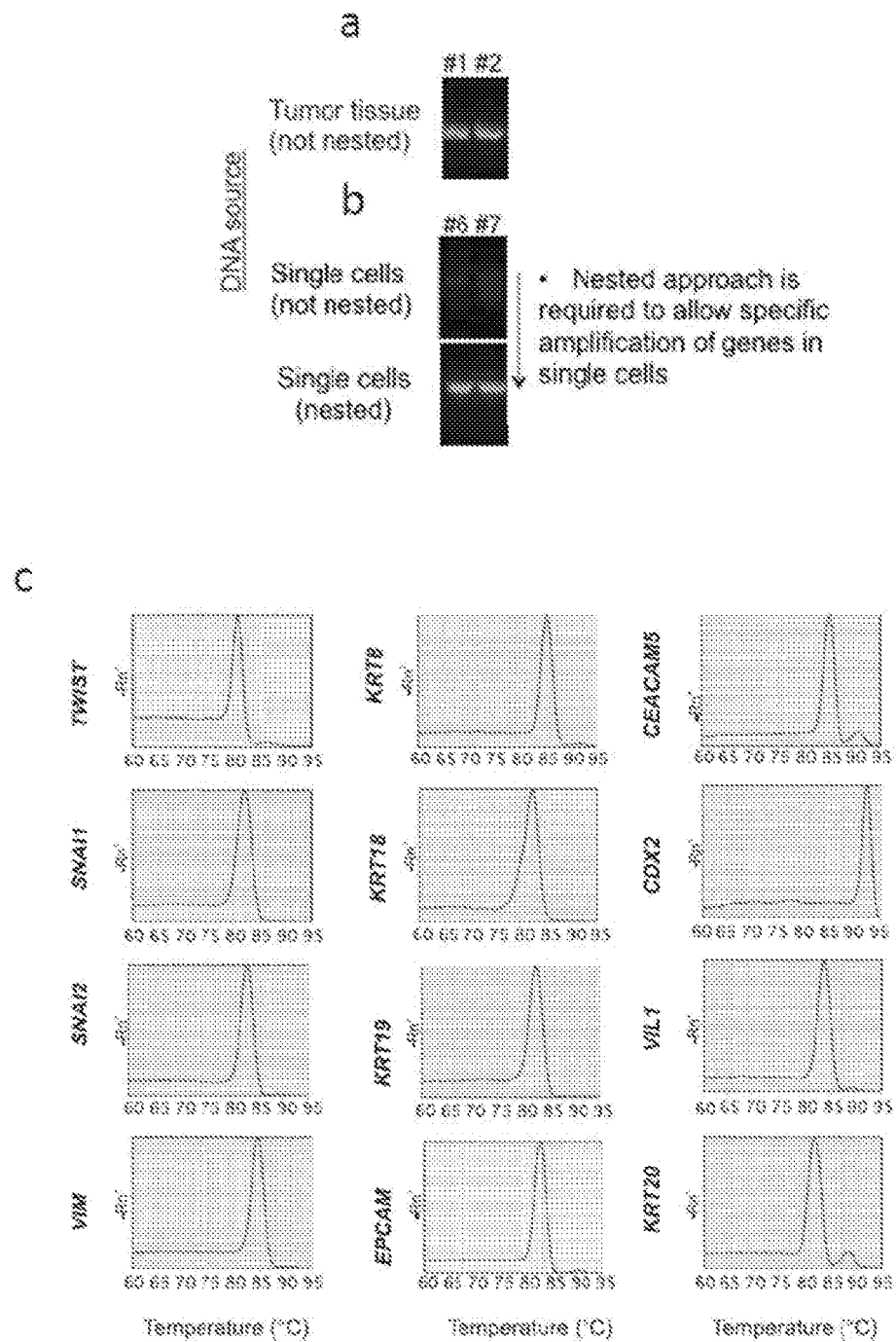
FIG. 2 shows that nested PCR is required for specific amplification of PCR products from single cells. In (a), primers for TP53 exon 6 were optimized to amplify tissue DNA and obtain specific products that can be sequenced. In (b), TP53 exon 6 was preamplified using the same primer pair and the reaction was split in 2 equal amounts. The first part was used in a second round of PCR using the same primer pairs. This resulted in unspecific and inefficient amplification (top panel). Specific PCR products were then obtained by performing the second amplification using a nested pair of primers (bottom panel). (c) shows melting curves of several seminested assays for RNA detection by qPCR, indicating specific amplification of the target product.

The inventors have found that specific amplification of both DNA and RNA can only be achieved by using at least a semi-nested approach for RNA and a fully nested approach for DNA molecules (e.g. see FIG. 2). The term "semi-nested PCR" as used herein refers to a modified PCR technique in which one "nested primer" is used to reduce non-specific binding due to the amplification of unexpected binding sites. A "fully nested approach" would refer to a modified PCR technique where two nested primers are used on either side on a template DNA. The use of "nested primers" allow the specific recognition of a PCR product amplified using a first set of primers, thus eliminating contamination from unwanted products such as primer dimers, hairpins and alternative primer target sequences. The inventors have also found that amplification of DNA and RNA molecules are differentially affected by annealing temperature in the pre-amplification step. A trade-off therefore needs to be set in order to amplify both molecules.

Accordingly, in one embodiment, the method according to the first aspect further comprises the step of: subjecting the sample from step (b) to a semi-nested PCR using the reverse primer in step (a) or the forward primer in step (b)(i), and a nested primer that binds within the amplified target cDNA region. The nested primer may be one that matches or corresponds to the reverse primer in step (a) or the forward primer in step (b)(i). In another embodiment, the method according to the first aspect further comprises the step of: subjecting the sample from step (b) to a nested PCR using a nested primer pair that binds within the amplified target DNA region. In one embodiment, steps (a) and (b) are conducted in the same reaction mixture.

In one embodiment, the method according to the first aspect is performed simultaneously for one or more target RNA regions, and/or one or more target cDNA regions, and/or one or more target DNA regions. Accordingly, one or more reverse primers, each having the same or a differing specificity for a target RNA region may be used in step (a), one or more forward primers, each having the same or a differing specificity for a target cDNA region may be used in step (b)(i), one or more primer pairs, each having the same or a differing specificity for a target DNA region may be used in step (b)(ii), one or more nested primers that bind to a target cDNA region, and one or more nested primer pairs that bind to a target DNA region, may be used.

Advantageously, the method according to the first aspect can be used to analyze RNA and DNA in instances where a limited amount of sample is available.

In one embodiment, the sample comprises a single cell, or a plurality of cells (e.g. a low number of cells comprising about 2 to about 100 cells, about 2 to about 90 cells, about 2 to about 80 cells, about 2 to about 70 cells, about 2 to about 60 cells, about 2 to about 50 cells, about 2 to about 40 cells, about 2 to about 30 cells, about 2 to about 20 cells, about 2 to about 10 cells, about 2 to about 5 cells, about 5 to about 100 cells, about 10 to about 100 cells, about 20 to about 100 cells, about 30 to about 100 cells, about 40 to about 100 cells, about 50 to about 100 cells, about 60 to about 100 cells, about 70 to about 100 cells, about 80 to about 100 cells, or about 90 to about 100 cells). The single cell or plurality of cells may be lysed to release the RNA and DNA contained within the cell (or cells) prior to step (a).

In another embodiment, the sample comprises cell-free RNA, or cell-free DNA.

The RNA or DNA may be present in a low amount, for example from about 1 pg to about 10 ng, about 5 pg to about 10 ng, about 5 pg to about 5 ng, about 5 pg to about 1 ng, about 5 pg to about 500 pg, about 5 pg to about 250 pg, about 5 pg to about 125 pg, about 5 pg to about 100 pg, or about 5 pg to about 50 pg.

The sample may be a sample of tissues, cells, vesicles such as exosomes, body fluids and isolates thereof etc., isolated from a subject. Examples of samples include: whole blood, blood fluids (e.g. serum and plasma), lymph and cystic fluids, sputum, stool, tears, mucus, hair, skin, ascitic fluid, cystic fluid, urine, nipple exudates, nipple aspirates, semen, vaginal fluid, sweat, exosomes or other vesicles, sections of tissues such as biopsy and autopsy samples, frozen sections taken for histologic purposes, archival samples, explants and primary and/or transformed cell cultures derived from patient tissues, clinical samples, forensic samples from crime scenes, soil samples etc.

The single cell or plurality of cells may be a eukaryotic cell, a bacterial cell or an archeal cell, a cell from a pre-implantation embryo, a stem cell, a suspected cancer cell, a suspected tumor-derived cell, a suspected embryonic cell, a cell from a pathogenic organism, or a cell obtained from a crime scene.

In one embodiment, the first primer pair comprises primers that span exon-exon boundaries or are separated by at least one intron on the corresponding DNA region.

In one embodiment, the second primer pair comprises primers that bind to intronic regions of the target DNA region.

The term "exon" refers to the portion of the genomic DNA that becomes a part of the genomic DNA that is converted into the mature messenger mRNA. The term "intron" or "intronic region" refers to the portion of the genomic DNA that is removed by RNA splicing and which would therefore not be present in the final mature mRNA.

The term "analyze" or "analyzing" refers to studying or examining the amplified target cDNA region and/or the amplified target DNA region by various techniques known in the art.

The amplified cDNA region and/or the amplified target DNA region may be studied for its gene expression or for mutations that may be present.

In one embodiment, the analysis in step (c) comprises analyzing the amplified target cDNA for gene expression (e.g. in a gene expression analysis). The gene expression analysis may be conducted using any techniques known in the art, such as quantitative PCR, digital PCR, microarray, and the like.

In one embodiment, the analysis in step (c) comprises analyzing the amplified target DNA for mutations (e.g. in a mutational analysis). The mutational analysis may be conducted using any techniques known in the art, such as Sanger sequencing, Maxam-Gilbert sequencing, Pyrosequencing, Shot-gun sequencing, high-throughput DNA sequencing, Allele-Specific PCR (ASPCR) or High Resolution Melting temperature PCR (HRM).

The pre-amplification in step (b) of the method according to the first aspect may comprise one or more cycling steps. Each cycling step may comprise one or more cycles of amplification (i.e. denaturation, annealing and elongation) at a pre-determined temperature for a pre-determined duration. It would be appreciated that the number of cycling steps, the number of cycles of denaturation, annealing and elongation, the temperature(s) at which the cycles are conducted, and the duration for which each temperature is applied would depend on the reagents used in the amplification reactions, the target cDNA or DNA region, the primers used, the sample(s) to be amplified. In one embodiment, the amplification does not include a final extension step.

In one embodiment, step (b) comprises about 1 to about 50 cycling steps, about 1 to about 40 cycling steps, about 1 to about 30 cycling steps, about 1 to about 25 cycling steps, about 1 to about 20 cycling steps, about 1 to about 10 cycling steps, about 1 to about 5 cycling steps, about 1 to about 4 cycling steps, about 1 to about 3 cycling steps, about 1 cycling step, about 2 cycling steps, or about 3 cycling steps. In one embodiment, step (b) comprises 3 cycling steps.

In one embodiment, each cycling step comprises about 1 to about 50 cycles, about 1 to about 40 cycles, about 1 to about 30 cycles, about 1 to about 25 cycles, about 1 to about 20 cycles, about 1 to about 18 cycles, about 1 to about 15 cycles, about 1 to about 10 cycles, about 1 to about 6 cycles, about 2 cycles, about 4 cycles, about 6 cycles, about 8 cycles, about 10 cycles, about 20 cycles, about 30 cycles, about 40 cycles, or about 50 cycles of denaturation, annealing and elongation. In one embodiment, each cycling step comprises 6 cycles of denaturation, annealing and elongation.

In one embodiment, the annealing and/or elongation temperature in a cycle is about 40° C. to about 75° C., about 40° C. to about 70° C., about 40° C. to about 65° C., about 40° C. to about 60° C., about 40° C. to about 55° C., about 40° C. to about 50° C., about 40° C., about 45° C., about 50° C., about 55° C., about 60° C., about 65° C., about 70° C., or about 75° C.

The annealing and/or elongation temperature for successive cycling steps may be reduced by about 1° C. to about 10° C., about 1° C. to about 9° C., about 1° C. to about 8° C., about 1° C. to about 7° C., about 1° C. to about 6° C., about 1° C. to about 5° C., about 1° C. to about 4° C., about 1° C. to about 3° C., or about 1° C. to about 2° C.

In one embodiment, the annealing and/or elongation is carried out for about 10 seconds to about 10 minutes, about 10 seconds to about 8 minutes, about 10 seconds to about 6 minutes, about 10 seconds to about 4 minutes, about 10 seconds to about 2 minutes, about 10 seconds to about 1 minute, about 1 minute, about 2 minutes, about 4 minutes, about 6 minutes, about 8 minutes, or about 10 minutes.

In one embodiment, the denaturation is carried out at a temperature of about 75° C. to about 120° C., about 75° C. to about 105° C., about 75° C. to about 95° C., about 75° C. to about 90° C., about 75° C. to about 85° C., about 75° C. to about 80° C., about 75° C., about 80° C., about 85° C., about 90° C., about 95° C., about 100° C., about 105° C., about 110° C., about 115° C., or about 120° C. The denaturation may be carried out for about 1 second to about 10 minutes, about 1 second to about 5 minutes, about 1 second to about 4 minutes, about 1 second to about 3 minutes, about 1 second to about 2 minutes, about 1 second to about 1 minute, about 1 second, about 10 seconds, about 20 seconds, about 30 seconds, about 40 seconds, about 50 seconds, about 1 minute, about 2 minutes, about 3 minutes, about 4 minutes, about 5 minutes, or about 10 minutes. In one embodiment, step (b) of the method according to the first aspect comprises:

6 cycles of 60° C. for 4 minutes followed by 95° C. for 1 minute, 6 cycles of 55° C. for 4 minutes followed by 95° C. for 1 minute, and 6 cycles of 50° C. for 4 minutes followed by 95° C. for 1 minute.

In a second aspect, there is provided a method of simultaneously analyzing RNA and DNA in a sample, the method comprising the steps of:

(a) lysing a cell in the sample;

(b) contacting the lysed cell sample with a reverse primer from a first primer pair, the reverse primer from the first primer pair being directed to a target RNA region, and a reverse transcriptase to effect reverse transcription of the RNA into cDNA;

(c) subsequently contacting the lysed cell sample with:

(i) a forward primer from the first primer pair, the forward primer from the first primer pair being directed to a target cDNA region, (ii) a reverse primer and a forward primer from a second primer pair, the reverse primer and forward primer from the second primer pair being directed to a target DNA region, and (iii) a DNA polymerase to simultaneously amplify the target cDNA region and the target DNA region in a pre-amplification step;

(d) subjecting the sample from step (c) to a semi-nested PCR using the reverse primer in step (b) or the forward primer in step (c)(i), a nested primer that binds within the pre-amplified target cDNA region, and a DNA polymerase to further amplify the target cDNA region, and/or subjecting the sample from step (c) to a nested PCR using a nested primer pair that hinds within the pre-amplified target DNA region and a DNA polymerase to further amplify the target DNA region; and (e) analyzing the further amplified target cDNA region and/or the further amplified target DNA region.

In one embodiment of the method of the second aspect, the nested primer in step (d) may be one that matches or corresponds to the reverse primer in step (b) or the forward primer in step (c)(i). In one embodiment of the method of the second aspect, steps (b) and (c) are conducted in the same reaction mixture.

Like the method of the first aspect, the method according to the second aspect may also be performed simultaneously for one or more target RNA regions, and/or one or more target cDNA regions, and/or one or more target DNA regions (such as one or more target genomic DNA regions). Accordingly, one or more reverse primers, each having the same or a differing specificity for a target RNA region may be used in step (b) of the method according to the second aspect, one or more forward primers, each having the same or a differing specificity for a target cDNA region may be used in step (c)(i) of the method according to the second aspect, one or more primer pairs, each having the same or a differing specificity for a target DNA region may be used in step (c)(ii) of the method according to the second aspect, one or more nested primers that bind to a target cDNA region, and one or more nested primer pairs that bind to a target DNA region, may be used in step (d) of the method of the second aspect.

The term "lysing" refers to breaking apart the membrane of a cell. This allows DNA or RNA in the cell to be accessible to contact by, for example, one or more primers and enzymes.

The lysing in step (a) of the method of the second aspect may be conducted using any techniques known in the art, for example, use of a lysis buffer, sonication, freeze-thaw, mechanical disruption, and the like.

In one embodiment, the pre-amplification in step (c) of the method of the second aspect does not include a final extension step.

The samples, primers, primer pairs, analytical techniques, and pre-amplification conditions (such as cycling steps, and temperatures and durations used therein) as described above for the method of the first aspect may also be used in the method of the second aspect.

In a third aspect, there is provided use of the method according to the first or second aspect for determining the DNA profile and/or the gene expression profile of a single cell or a plurality of cells (e.g. a low number of cells comprising about 2 to about 100 cells), or cell-free RNA and/or DNA (e.g. a low amount of DNA and/or RNA comprising about 1 pg to about 10 ng of DNA and/or RNA) derived from a single cell or a plurality of cells.

The term "DNA profile" refers to the characterization of the DNA sequence of a selection of genes within a cell or a plurality of cells. The term "gene expression profile" refers to the characterization of the expression level of a selection of genes within a cell or plurality of cells.

The use may be applied to a biological sample comprising heterogenous cell types from a subject or a low amount of cell-free RNA and/or DNA. The biological sample may be selected from the group consisting of a pre-implantation embryo, tissues, cells (e.g. a stem cell, a suspected cancer cell), body fluids and isolates thereof etc., isolated from a subject. Examples of biological samples include: whole blood, blood fluids (e.g. serum and plasma), lymph and cystic fluids, sputum, stool, tears, mucus, hair, skin, ascitic fluid, cystic fluid, urine, nipple exudates, nipple aspirates, semen, vaginal fluid, sweat, exosomes or other vesicles, sections of tissues such as biopsy and autopsy samples, frozen sections taken for histologic purposes, archival samples, explants and primary and/or transformed cell cultures derived from patient tissues, clinical samples, forensic samples from crime scenes, soil samples etc.

The subject may be a mammal, such as a human. The linkage of the DNA profile to the gene expression profile for the single cell or the plurality of cells, or the low amount of cell-free DNA and/or cell-free RNA may be used to optimize anti-cancer therapy for the subject or for diagnostic/prognostic purposes, as illustrated by the Examples as described herein. Alternatively, the use may be applied to a cell from a pathogenic organism, or a cell obtained from a crime scene, or a low amount of cell-free RNA and/or cell-free DNA derived from a pathogenic organism or a crime scene.

In a fourth aspect, there is provided use of the method according to the first or second aspect for validation of large-scale transcriptomics data sets. For example, the use may be applied to confirm specific results obtained by high-throughput RNA sequencing experiments that have been generated using small-scale samples (such as a biological sample comprising of a single cell or a low number of cells, e.g. about 2 to about 101) cells, or a low amount of RNA). This is important to rule out false positive results and to validate the results using an independent methodology. The method can be used to validate both RNA expression and/or mutational profile results that are generated by high-throughput RNA sequencing.

In a fifth aspect, there is provided a kit for performing the method according to the first or second aspect, or for use according to the third or fourth aspect, wherein the kit comprises:

(a) a primer selected from the group consisting of:
i. the reverse primer of step (a) of the method of the first aspect or step (b) of the method of the second aspect,
ii. the forward primer of step (b)(i) of the method of the first aspect or step (c)(i) of the method of the second aspect,
iii. the primer pair of step (b)(ii) of the method of the first aspect or step (c)(ii) of the method of the second aspect, and
iv. the nested primer and nested primer pair of the method of the first aspect or step (d) of the method of the second aspect;

(b) one or more reagents, selected from the group consisting of:
i. a reverse transcriptase and one or more suitable reaction buffers for the reverse transcription in step (a) of the method of the first aspect or step (b) of the method of the second aspect,
ii. a DNA polymerase and one or more suitable reaction buffers for the amplification in step (b) or the semi-nested or nested PCR of the method of the first aspect, or step (c) or (d) of the method of the second aspect, and
iii. one or more labelled or unlabelled deoxyribonucleotides selected from the group consisting of dATP, dCTP, dGTP, and dTTP or dUTP; and (c) instructions for performing the method according to the first or second aspect, or for use according to the third or fourth aspect.

The kit according to the fifth aspect may include one or more lysis buffers for lysing a cell in a sample prior to the method of the first aspect, or in step (a) of the method of the second aspect. Lysis buffers commonly used in the art, such as alkaline lysis buffers or cell lysis buffers containing proteinase K, or simply buffers containing a detergent or a compound and/or an enzyme that will disrupt the cell and allow its nucleic acids to be released in solution may be used.

The kit according to the fifth aspect may also include probes or dyes for quantitative real-time PCR. Exemplary probes and dyes include, but are not limited to SYBR green dye, EvaGreen, dsGreen, TaqMan probes, hybridization probes and the like.

The kit may also include instructions for designing one or more of the primers of component (a) of the kit of the fifth aspect, and/or optimizing the pre-amplification cycling conditions of step (b) of the method of the first aspect or step (c) of the method of the second aspect.

In one embodiment, the primers and/or reagents are pre-mixed in combinations suitable for the lysis, pre-amplification, and amplification steps described above. In another embodiment, the primers are pre-mixed in combinations suitable for analysis of gene expression profiles or mutation signatures. The primers may be ones that have been designed for amplifying one or more target genes of interest.

In a further embodiment, the kit comprises one or more containers comprising one or more reaction buffers for performing the methods and/or uses described above. In some embodiments, the kit includes software-driven assay protocols for use in commercial PCR instrumentation (such as the Life Technologies 7500 FastDx or Cepheid SmartCycler® II), which may be provided on a CD.

As used herein, the singular form "a", "an" and "the" include plural references unless the context clearly dictates otherwise. For example, the term "a primer" includes a plurality of primers, including mixtures thereof.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

EXAMPLES

Example 1

Primer Design and scrmPCR Protocols

The following protocol steps or materials have been implemented in the method from sources already described elsewhere:

1) Conditions described in Pcixoto et al., specifically:
   a. Use of reverse specific primers for reverse transcriptase reaction.
   b. Use of seminested PCR for RNA transcripts quantitation.
2) Materials from the CellsDirect™ One-Step qRT-PCR Kit (Invitrogen), specifically:
   a. 2X Reaction Mix cat #11753-100
   b. SuperScript® III RT/Platinum® Taq Mix contained in cat #11753-100
3) Conditions described in Protocol PN 100-4109 from the Biomark HD system (Fluidigm) (Sanchez-Freire et al) and
   http://www.fluidigm.com/home/fluidigm/docs/AppNote_2v1Step_pf9.pdf), specifically:
   a. Deposition of single cell in 2× Reaction mix.
   b. Annealing time of the preamplification step (4 minutes).

Primer Design Protocol

Primer Design Method for Detection of Small Amount of RNA in Multiplex Tests (Down to Single Cell Detection)

To design primers for mRNA amplification in the presence of genomic DNA at the single cell scale, there must be an intronic sequence on the genomic DNA between primers, or at least one primer must sit at the exon-exon junction. In addition, the primers need to be specific and should not amplify unwanted products.

This protocol can be used to generate primers for seminested/nested PCRs following the general method of Peixoto et. al. (Peixoto, A., Monteiro, M., Rocha, B. & Veiga-Fernandes, H. *Quantification of multiple gene expression in individual cells. Genome Res.* 14, 1938-1947 (2004)). Seminested PCR is required for robust amplification of RNA-derived gene transcripts. Nested PCR is required for robust amplification of genomic DNA.

Procedure:

The following tools were used (by opening in Firefox):

1) Ncbi primer design tool

This software is based on Primer3 and Blast for optimal primer pair findings. It can also design primers at the exon-exon junction.

Seminested PCR: for the external primer pairs, the parameters used may be varied accordingly depending on sample type and objective of the study.

2) Ensembl genome browser

This webtool allows for straightforward gene selection and curated ID retrieval.

3) Netprimer

This webtool allows checking of the quality of the primers, by rating it accordingly.

The following steps using the above webtools were applied:

a) searched for the gene of interest in Ensembl
b) checked for the correct identification and clicked on "external references"
c) scrolled down and identified the RefSeq identifier
d) copied and pasted the identifier on the ncbi primer design tool window
e) looked for primers using the link provided above or customized stringency
f) checked the primers on the Netprimer application and selected the best primer pair by rating.
g) if no primers were returned, less stringent parameters were used.

Example: Design of CD45 primers.

Forward primer
(SEQ ID NO: 137)
AAGACAACAGTGGAGAAAGGACGCA

Reverse primer
(SEQ ID NO: 138)
CAGTGGGGGAAGGTGTTGGGCT

Product length 159
Exon junction 131/132 (forward primer) on template NM_002838.3

To look for the internal probe, the same search as above may be performed, using the primer with better ratings and constrain the PCR product length to retrieve a primer that sits in the PCR product.

For primers on genomic regions, the following steps were applied:

a) looked for the gene of interest in Ensembl
b) clicked on sequence
c) selected genomic region for sequencing including intronic regions
d) copied and pasted on primer-blast
e) looked for primers targeting the region of interest Two pairs of primers were designed, one with annealing temperature (T) of 60° C., one with annealing T of 65° C.

For design of internal probes, the amplified region was selected by primer set one, copied and pasted in primer-blast. Primers with an annealing T of 60° C. were selected.

Primers Design:

Primers were designed using Primer-BLAST (Ye et al and Bbenek, et al) and using the primer design protocol described above. For each RNA transcript, primers either spanning exon-exon boundaries or primers separated by at least one intron on the corresponding genomic DNA region were designed. This allows primers to specifically amplify RNA transcripts, whereas DNA regions would not be amplified. Furthermore, primers for mutational analysis were designed to hind intronic regions of the target gene. This would avoid amplification of cDNA transcripts that may have arisen from unspecific or specific reverse transcription. (see Primer Design protocol (above) and Tables 1A to 1C).

TABLE 1A

Primers used in scrm-PCR assays (Pre-amplification step)
Pramplification step

| Gene name | ID (transcript or gene) | Marker | Forward primer | Reverse primer |
|---|---|---|---|---|
| CEACAM5 | NM_004363.2 | C | CCCAAGCCCTCCATCTCCAGCAAC (SEQ ID NO: 1) | GCATCCGGGCCATAGAGGACATT (SEQ ID NO: 2) |
| CDX2 | NM_001265.4 | C | TGGGCTGCTGCAAACGCTCAAC (SEQ ID NO: 3) | TTTCGTCCTGGTTTTCACTTGGCTG (SEQ ID NO: 4) |
| KRT20 | NT_01783.15 | C | AAAATGGCCATGCAGAACCT (SEQ ID NO: 5) | GAAGTCCTCAGCAGCCAGTT (SEQ ID NO: 6) |
| FN1 | NT_5403.17 | EMT | CCACGGGAGCCTCGAA (SEQ ID NO: 7) | TAAAACCTCGGCTTCCTCCA (SEQ ID NO: 8) |
| CDH2 | NT_010966.14 | EMT | GGATGAAGATGGCATGGTGT (SEQ ID NO: 9) | CCCAGTCTCTCTTCTGCCTT (SEQ ID NO: 10) |
| SERPINE1 | NT_007933.15 | EMT | GCCAAGAGCGCTGTCAA (SEQ ID NO: 11) | CAGCAGACCCTTCACCAAA (SEQ ID NO: 12) |
| TWIST1 | NM_000474.3 | EMT | ACCTAGATGTCATTGTTTCCAGAGAGCAGAGGTGTGAGGATGGTG (SEQ ID NO: 13) | (SEQ ID NO: 14) |
| SNAI1 | NM_005985.3 | EMT | GACCCCAATCGGAAGCCTAA (SEQ ID NO: 15) | GCGGTGGGGTTGAGGAT (SEQ ID NO: 16) |
| VIM | NM_003380.3 | EMT | GATGTTTCCAAGCCTGACCT (SEQ ID NO: 17) | CAGTGGACTCCTGCTTTGC (SEQ ID NO: 18) |
| SNAI2 | NM_003068.4 | EMT | AGCGAACTGGACACACATACA (SEQ ID NO: 19) | AGGAGGTGTCAGATGGAGGA (SEQ ID NO: 20) |
| FOXC2 | NM_005251.2 | EMT | CGCCTAAGGACCTGGTGAA (SEQ ID NO: 21) | GAAGCGGTCCATGATGAACT (SEQ ID NO: 22) |
| FOXC1 | NM_001453.2 | EMT | CACACCCTCAAAGCCGAACT (SEQ ID NO: 23) | AAAGTGGAGGTGGCTCTGAA (SEQ ID NO: 24) |

TABLE 1A-continued

Primers used in scrm-PCR assays (Pre-amplification step)
Pramplification step

| Gene name | ID (transcript or gene) | Marker | Forward primer | Reverse primer |
|---|---|---|---|---|
| CDH1 | NT_010498.15 | EMT/L(Ep) | GAGAGAGGCCGCGTCCT (SEQ ID NO: 25) | GGCCTTTTGACTGTAATCACAC (SEQ ID NO: 26) |
| KRT18(1) | NM_000224.2 | EMT/L(Ep) | TGCTCACCACACAGTCTGAT (SEQ ID NO: 27) | CACTTTGCCATCCACTAGCC (SEQ ID NO: 28) |
| KRT8 | NM_002273.3 | EMT/L(Ep) | AAGGATGCCAACGCCAAGTT (SEQ ID NO: 29) | CCGCTGGTGGTCTTCGTATG (SEQ ID NO: 30) |
| KR719 | NM_002276.4 | EMT/L(Ep) | CAGCCACTACTACACGACCA (SEQ ID NO: 31) | CGTTGATGTCGGCCTCCA (SEQ ID NO: 32) |
| EPCAM | NT_022184.15 | EMT/L(Ep) | GCAGGTCCTCGCGTTCG (SEQ ID NO: 33) | TCTCCCAAGTTTTGAGCCATTC (SEQ ID NO: 34) |
| TP53 exon 5 | ENSG00000141510 | G | TGTTCACTTGTGCCCTGACT (SEQ ID NO: 35) | CAGCCCTGTCGTCTCTCCAG (SEQ ID NO: 36) |
| TP53 exon 6 | ENSG00000141510 | G | TGGTTGCCCAGGGTCCCCA (SEQ ID NO: 37) | TGGAGGGCCACTGACAACCA (SEQ ID NO: 38) |
| TP53 exon 7 | ENSG00000141510 | G | CTTGCCACAGGTCTCCCCAA (SEQ ID NO: 39) | AGGGGTCAGAGGCAAGCAGA (SEQ ID NO: 40) |
| TP53 exon 8 | ENSG00000141510 | G | TTCCTTACTGCCTCTTGCTT (SEQ ID NO: 41) | AGGCATAACTGCACCCTTGG (SEQ ID NO: 42) |
| BRAF exon 15 (2) | ENSG00000157764 | G | CATAATGCTTGCTCTGATAGG (SEQ ID NO: 43) | GGCCAAAATTTAATCAGTGGA (SEQ ID NO: 44) |
| KRAS exon 2 | ENSG00000133703 | G | TTATAAGGCCTGCTGAAAATGACTGTCATGAAAATGGTCAGAGAAACCTT (SEQ ID NO: 45) | (SEQ ID NO: 46) |
| EGFR | NT_033968.6 | L(Ep) | GTCGGGCTCTGGAGGAAAA (SEQ ID NO: 47) | CTCTGGAGGCTGAGAAAATGAT (SEQ ID NO: 48) |
| PTPRC | NT_004487.19 | L(He) | GACATCATCACCTAGCAGTTCATG (SEQ ID NO: 49) | CAGTGGGGAAGGTGTTGG (SEQ ID NO: 50) |
| VWF | NM_000552.3 | L(En) | ACACAGGGGGACCAAAGAG (SEQ ID NO: 51) | GAGATGCCCGTTCACACCA (SEQ ID NO: 52) |
| PECAM1 | NM_000442.4 | L(He, En) | TCTCAACGGTGACTTGTGG (SEQ ID NO: 53) | GTTCTTCCCATTTTGCACCGT (SEQ ID NO: 54) |
| COL1A1 | NM_000088.3 | L(Me) | TGTTCAGCTTTGTGGACCTC (SEQ ID NO: 55) | GGTTTCCACACGTCTCGGT (SEQ ID NO: 56) |
| CD68 | NM_001251.2 | L/Me | CATTCTTTCACCAGCTGTCCA (SEQ ID NO: 57) | GCACCAGGGCGAGGA (SEQ ID NO: 58) |
| MCAM | NM_006500.2 | L(En) | CTCGGTCCCAGGAGTACC (SEQ ID NO: 59) | TGTACAAACCACTCGACTCCA (SEQ ID NO: 60) |
| FCGR3A | NM_000569.6 | L(He) | CCCTTGCCAGACTTCAGACT (SEQ ID NO: 61) | GGGAGATCTTCAGTCCGCAT (SEQ ID NO: 62) |
| GYPA | NM_002099.6 | L(Er) | CTAGCAGGCTAAGGTCAGACA (SEQ ID NO: 63) | GTGTCCCGTTTGTGCGTATC (SEQ ID NO: 64) |
| ITGA2H | NM_000419.3 | L(Me) | CTTCTATGCAGGCCCCAAT (SEQ ID NO: 65) | AGCCTACATTTCGGGTCTCATC (SEQ ID NO: 66) |
| DCSTAMP | NM_030788.3 | L(He) | CTCCCGCTGAATAAGGAGGAA (SEQ ID NO: 67) | TCTTGAGTTCCTTGTTTCTCTCCGT (SEQ ID NO: 68) |
| CD34 | NM_001773.2 | S/L(En) | CCTTCTGGGTTCATGAGTCTTGACATGTCGTTTCTGTGATGTTTGTTGTG (SEQ ID NO: 69) | (SEQ ID NO: 70) |
| ACTB | NM_001101.3 | QC | CTGGCACCACACCTTCTACA (SEQ ID NO: 71) | TAGCACAGCCTGGATAGCAA (SEQ ID NO: 72) |
| FOLH1 | NT_009237.18 | TEC | CGGATATTGTACCACCTTTCAGT (SEQ ID NO: 73) | AGCAGGGTCGGAGTAGAGAA (SEQ ID NO: 74) |

TABLE 1A-continued

Primers used in scrm-PCR assays (Pre-amplification step)
Pramplification step

| Gene name | ID (transcript or gene) | Marker | Forward primer | Reverse primer |
|---|---|---|---|---|
| ENG | NT_008470.19 | L(En) | GTGACGGTGAAGGTGGAACTGA (SEQ ID NO: 75) | TTGAGGTGTGTCTGGGAGCT (SEQ ID NO: 76) |
| KDR | NM_002253.2 | L(En) | GAAATGACACTGGAGCCTACAAG (SEQ ID NO: 77) | AATGGACCCGAGACATGGAAT (SEQ ID NO: 78) |
| CDH5 | NM_001795.3 | L(En) | GTTCACGCATCGGTTGTTCAAT (SEQ ID NO: 79) | GCCTGCTTCTCTCGGTCCAA (SEQ ID NO: 80) |
| TEK | NT_008413.19 | L(En) | CTTATTTCTGTGAAGGGCGAGTT (SEQ ID NO: 81) | CTCCCTTGTCCACAGTCATAGT (SEQ ID NO: 82) |
| ANGPT2 | NM_001147.2 | L(En) | AACACTCCCTCTCGACAAACAAATT (SEQ ID NO: 83) | CTGTAGTTGGATGATGTGCTTGTC (SEQ ID NO: 84) |
| HPRT1 | NM_000194.2 | QC | TGACCAGTCAACAGGGGACA (SEQ ID NO: 85) | GGTCCTTTTCACCAGCAAGCT (SEQ ID NO: 86) |
| UHC | NM_021009.5 | QC | TCGGCCTTAGAACCCCAGTA (SEQ ID NO: 87) | ACGAAGATCTGCATTGTCAAGTG (SEQ ID NO: 88) |

References and Legend
(1) derived from Hesse et al. (2001) *J. Cell Sci.* 114, 2569
(2) derived from Sakaizawa et al. Br. J. Cancer (2012) 106, 939
Legend:
C: Colon-specific
EMT: Epithelial-mesenchymal transition marker
L: Lineage marker
G: Gene
QC: Quality control
TEC: Tumor endothelial cell marker
S: Stem cell marker
Ep: Epithelial marker
He: Hematopoietic cell marker
En: Endothelial cell marker
Mn: Megakaryocyte/platelet marker
Mo: Monocyte-macrophage marker
Er: Erythrocyte marker

TABLE 1B

Primers used in scrm-PCR assays for nested and semi-nested amplification
(Amplification Step)

| Gene name | Allows DNA/RNA discrimination | Forward primer (Amplification step) | Reverse primer |
|---|---|---|---|
| CEACAM5 | Reverse primer on exon junction | TGTGGTGGGTAAACAATCAGAGCC (SEQ ID NO: 89) | GCATCCGGGCCATAGAGGACATT (SEQ ID NO: 2) |
| CDX2 | Reverse primer on exon junction | CGGCGGAACCTGTGCGAGTG (SEQ ID NO: 90) | TTTCGTCCTGGTTTTCACTTGGCTG (SEQ ID NO: 4) |
| KRT20 | 2141 bp intron in DNA sequence | GCGACTACAGTGCATATTACAGA (SEQ ID NO: 91) | GAAGTCCTCAGCAGCCAGTT (SEQ ID NO: 6) |
| FN1 | 830 bp intron in DNA sequence | CAAGCCCGGTTGTTATGACA (SEQ ID NO: 92) | TAAAACCTCGGCTTCCTCCA (SEQ ID NO: 8) |
| CDH2 | 1690 bp intron in DNA sequence | AAGTTCCTGATATATGCCCAAGA (SEQ ID NO: 93) | CCCAGTCTCTCTTCTGCCTT (SEQ ID NO: 10) |
| SERPINE1 | 1148 bp intron in DNA sequence | AGAACTTCAGGATGCAGATGTCT (SEQ ID NO: 94) | CAGCAGACCCTTCACCAAA (SEQ ID NO: 12) |
| TWIST1 | Forward primer on exon junction | CCAGAGAAGGAGAAAATGGACAGT (SEQ ID NO: 95) | GCAGAGGTGTGAGGATGGTG (SEQ ID NO: 14) |
| SNAI1 | 682 bp intron in DNA sequence | GACCCCAATCGGAAGCCTAA (SEQ ID NO: 15) | GTAGGGCTGCTGGAAGGTAA (SEQ ID NO: 96) |
| VIM | 761 bp intron in DNA sequence | GATGTTTCCAAGCCTGACCT (SEQ ID NO: 17) | TGTACCATTCTTCTGCCTCCT (SEQ ID NO: 97) |
| SNAI2 | 745 bp intron in DNA sequence | AGCGAACTGGACACACATACA (SEQ ID NO: 19) | GTGGAATGGAGCAGCGGTAG (SEQ ID NO: 98) |

TABLE 1B-continued

Primers used in scrm-PCR assays for nested and semi-nested amplification
(Amplification Step)

| Gene name | Allows DNA/RNA discrimination | Forward primer | Reverse primer |
|---|---|---|---|
| FOXC2 | NA (single exon coding gene) | GCTCATCACCATGGCCATC (SEQ ID NO: 99) | GAAGCGGTCCATGATGAACT (SEQ ID NO: 22) |
| FOXC1 | NA (single exon coding gene) | CACACCCTCAAAGCCGAACT (SEQ ID NO: 23) | GAGGGATATTCTGTTCGCTGGT (SEQ ID NO: 100) |
| CDH1 | 63258 bp intron in DNA sequence | GGCAGAGTGAATTTTGAAGATTGC (SEQ ID NO: 101) | GGCCTTTTGACTGTAATCACAC (SEQ ID NO: 26) |
| KRT18(1) | 641 bp intron in DNA sequence | TGGAGGACCGCTACGCCCTA (SEQ ID NO: 102) | CCAAGGCATCACCAAGACTA (SEQ ID NO: 103) |
| KRT8 | 159 bp intron in DNA sequence | GCTGGAGGGCGAGGAGA (SEQ ID NO: 104) | CCGCTGGTGGTCTTCGTATG (SEQ ID NO: 30) |
| KRT19 | 2745 bp intron in DNA sequence | TGCGGGACAAGATTCTTGGT (SEQ ID NO: 105) | CGTTGATGTCGGCCTCCA (SEQ ID NO: 32) |
| EPCAM | 4118 bp intron in DNA sequence | CCGCAGCTCAGGAAGAATGT (SEQ ID NO: 106) | TCTCCCAAGTTTTGAGCCATTC (SEQ ID NO: 34) |
| TP53 exon 5 | Primers on intronic sequences | TTCAACTCTGTCTCCTTCCT (SEQ ID NO: 107) | CAGCCCTGTCGTCTCTCCAG (SEQ ID NO: 36) |
| TP53 exon 6 | Primers on intronic sequences | GCCTCTGATTCCTCACTGAT (SEQ ID NO: 108) | TTAACCCCTCCTCCCAGAGA (SEQ ID NO: 109) |
| TP53 exon 7 | Primers on intronic sequences | AAGGCGCACTGGCCTCATCTT (SEQ ID NO: 110) | AGGGGTCAGAGGCAAGCAGA (SEQ ID NO: 40) |
| TP53 exon 8 | Primers on intronic sequences | AGTGGTAATCTACTGGGACGG (SEQ ID NO: 111) | ACCTCGCTTAGTGCTCCCTG (SEQ ID NO: 112) |
| BRAF exon 15(2) | Primers on intronic sequences | CATAATGCTTGCTCTGATAGG (SEQ ID NO: 43) | TAGCCTCAATTCTTACCATC (SEQ ID NO: 113) |
| KRAS exon 2 | Primers on intronic sequences | TTATAAGGCCTGCTGAAAATGACT (SEQ ID NO: 45) | GCAAAGAATGGTCCTGCACCAGTAAT (SEQ ID NO: 114) |
| EGFR | 122920 bp intron in DNA sequence | TCTGGAGGAAAAGAAAGTTTGC (SEQ ID NO: 115) | CTCTGGAGGCTGAGAAAATGAT (SEQ ID NO: 48) |
| PTPRC | 53092 bp intron in DNA sequence | CAACAGTGGAGAAAGGACGCA (SEQ ID NO: 116) | CAGTGGGGAAGGTGTTGG (SEQ ID NO: 50) |
| VWF | Forward primer on exon junction | TGCCTCCAAAGGGCTGTATC (SEQ ID NO: 117) | GAGATGCCCGTTCACACCA (SEQ ID NO: 52) |
| PECAM1 | 12457 bp intron in DNA sequence | CAGTCTTCACTCTCAGGATGC (SEQ ID NO: 118) | GTTCTTCCCATTTTGCACCGT (SEQ ID NO: 54) |
| COL1A1 | 1463 bp intron in DNA sequence | TGTTCAGCTTTGTGGACCTC (SEQ ID NO: 55) | GTGGGATGTCTTCGTCTTGG (SEQ ID NO: 119) |
| CD68 | 311 bp intron in DNA sequence | AAAGTTTCTCCTGCCCCAGT (SEQ ID NO: 120) | GCACCAGGGCGAGGA (SEQ ID NO: 58) |
| MCAM | 1724 bp intron in DNA sequence | CTCGGTCCCAGGAGTACC (SEQ ID NO: 59) | CGGCCATTCTTGTACCAGATGA (SEQ ID NO: 121) |
| FCGR3A | Reverse primer on exon junction & intron in DNA seq | CCCTTGCCAGACTTCAGACT (SEQ ID NO: 61) | TTTCCCCAGCCCCTCCA (SEQ ID NO: 122) |
| GYPA | 20010 bp introns in DNA sequence | CAGGAACCAGCTCATGATCTC (SEQ ID NO: 123) | GTGTCCCGTTTGTGCGTATC (SEQ ID NO: 64) |
| ITGA2B | 3242 bp intron in DNA sequence | GGCGGCGTGTTCCTGT (SEQ ID NO: 124) | AGCCACATTTCGGGTCTCATC (SEQ ID NO: 66) |
| DCSTAMP | Reverse primer on exon junction | ACCTGGGGCTGTTTTTCCTC (SEQ ID NO: 125) | TCTTGAGTTCCTTGTTTCTCTCCGT (SEQ ID NO: 68) |

TABLE 1B-continued

Primers used in scrm-PCR assays for nested and semi-nested amplification
(Amplification Step)

| Gene name | Allows DNA/RNA discrimination | Forward primer | Reverse primer |
|---|---|---|---|
| CD34 | Forward and reverse primers on exon junction | CTACCCCAGAGTTACCTACCCA (SEQ ID NO: 126) | TGTCGTTTCTGTGATGTTTGTTGTG (SEQ ID NO: 70) |
| ACTB | 441 bp intron in DNA sequence | CTGGCACCACACCTTCTACA (SEQ ID NO: 71) | TAGCACAGCCTGGATAGCAA (SEQ ID NO: 72) |
| FOLH1 | 6811 bp intron in DNA sequence | CCAGAGGGCGATCTAGTGTA (SEQ ID NO: 127) | AGCAGGGTCGGAGTAGAGAA (SEQ ID NO: 74) |
| ENG | 256 bp intron in DNA sequence | GTGACGGTGAAGGTGGAACTGA (SEQ ID NO: 75) | AGTATTCTCCAGTGGTCCAGATCT (SEQ ID NO: 128) |
| KDR | 3192 bp intron in DNA sequence | GAAATGACACTGGAGCCTACAAG (SEQ ID NO: 77) | TGTTGGTCACTAACAGAAGCA (SEQ ID NO: 129) |
| CDH5 | 2143 bp intron in DNA sequence | CACGCCTCTGTCATGTACCA (SEQ ID NO: 130) | GCCTGCTTCTCTCGGTCCAA (SEQ ID NO: 80) |
| TEK | 10352 bp intron in DNA sequence | CTTATTTCTGTGAAGGGCGAGTT (SEQ ID NO: 81) | GTAGCTGGTAGGAAGGAAGCT (SEQ ID NO: 131) |
| ANGPT2 | 6144 bp intron in DNA sequence | GGACCAGACCAGTGAAATAAACAA (SEQ ID NO: 132) | CTGTAGTTGGATGATGTGCTTGTC (SEQ ID NO: 84) |
| HPRT1 | Reverse primer on exon junction & introns in DNA seq | TGACACTGGCAAAACAATGCA (SEQ ID NO: 133) | GGTCCTTTTCACCAGCAAGCT (SEQ ID NO: 86) |
| UBC | Reverse primer on exon junction | AAAGTAGTCCCTTCTCGGCG (SEQ ID NO: 134) | ACGAAGATCTGCATTGTCAAGTG (SEQ ID NO: 88) |

References and Legend
(1) derived from Hesse et al. (2001) J. Cell Sci. 114, 2569
(2) derived from Sakaizawa et al. Br. J. Cancer (2012) 106, 939

TABLE 1C

Primers used in scrm-PCR assays (Amplification products and qPCR melt curve peak)

| Gene name | Amplification product (bp) | qPCR melt curve peak (° C.) |
|---|---|---|
| CEACAM5 | 187 | 85.4 |
| CDX2 | 75 | 92.6 |
| KRT20 | 122 | 82.2 |
| FN1 | 113 | 81.8 |
| CDH2 | 184 | 83.2 |
| SERPINE1 | 81 | 84.8 |
| TWIST1 | 208 | 86 |
| SNAI1 | 72 | 82.4 |
| VIM | 100 | 84.8 |
| SNAI2 | 140 | 83.4 |
| FOXC2 | 82 | 83.7 |
| FOXC1 | 146 | 76.1 |
| CDH1 | 107 | 83 |
| KRT18(1) | 210 | 89.2 |
| KRT8 | 72 | 83.5 |
| KRT19 | 144 | 86.35 |
| EPCAM | 179 | 82.9 |
| TT53 exon 5 | 248 | NA |
| TT53 exon 6 | 182 | NA |
| TP53 exon 7 | 219 | NA |
| TP53 exon 8 | 141 | NA |
| BRAF exon 15(2) | 197 | NA |
| KRAS exon 2 | 177 | NA |
| EGFR | 87 | 81.75 |
| PTPRC | 155 | 83.5 |
| VWF | 275 | 86.2 |
| PECAM1 | 173 | 86.4 |
| COL1A1 | 108 | 88 |
| CD68 | 84 | 85.5 |
| MCAM | 175 | 86.8 |
| FCGR3A | 90 | 81.8 |
| GYPA | 177 | 81/84 |
| ITGA2B | 91 | 88.4 |
| DCSTAMP | 172 | 78.1 |
| CD34 | 155 | 82.3 |
| ACTB | 166 | 88.5 |
| FOLH1 | 189 | 82 |
| ENG | 133 | 87.5 |
| KDR | 115 | 81 |
| CDH5 | 107 | 80.8 |
| TEK | 88 | 82.4 |
| ANGPT2 | 97 | 82.9 |
| HPRT1 | 94 | 82.3 |
| UBC | 174 | 87.9 |

References and Legend
(1) derived from Hesse et al. (2001) J. Cell Sci. 11.4, 2569
(2) derived from Sakaizawa et al. Br. J. Cancer (2012) 106, 939 scrmPCR Protocol

1) Single cells were micromanipulated in 5 µl 2× Reaction Buffer (CellsDirect™ One-Step qRTPCR Kit (Invitrogen)) and stored at −80° C. until use.

2) Single cell RNA transcripts were reverse transcribed at 50° C. for 30 min using SuperScript® III RT (Invitrogen) and a mix of 100 nM target reverse primers. The reverse transcriptase component was inactivated at 95° C. for one minute. Next, the samples were placed on ice, and was proceeded immediately to the next step.

3) A pre-amplification round was next performed by adding a mix of forward primers (matching the reverse primers added in step 2) and primer pairs for specific DNA regions.

4) Preamplification was performed similarly as described for the Protocol PN 100-4109 from the Biomark HD system (Fluidigm), using 4 minutes annealing time but changing the annealing temperature to the following cycling steps:

6× cycles: 4', 60° C.-1', 95° C.
6× cycles: 4', 55° C.-1', 95° C.
6× cycles: 4', 50° C.-1', 95° C.

5) Primers cleanup from the samples was performed using standard methods (e.g. spin columns such as Axygen Axyprep PCR Clean-up Kit-Cat #14-223-018).

6) Samples were diluted 1/20-1/50 and stored at −20 until further use. This resulted in at least 200 µl of preamplified sample, which is sufficient for 100 reactions.

7) For RNA transcript quantitation, quantitative PCR was performed on a ViiA7 Instrument (Applied Biosystems) using 2 ul of preamplification reaction from 5), seminested primer pairs according to the target transcript (Table 1B) and the SensiFAST SYBR Lo-ROX Kit (Bioline) following the manufacturer protocol. To analyze selected DNA mutational hotspots, PCR was performed by using 2 ul of preamplification reaction from 5), nested PCR primer pairs (Table 1B) and a mastermix containing a proof reading polymerase (KOD Mastermix, EMD Millipore) following manufacturer's instructions. PCR products were separated on agarose gel, specific bands were excised and sequenced using the Sanger method. Step 7 can be performed using any qPCR method and the listed primers. PCR for DNA sequence can be performed using any Taq polymerase with proofreading activity and mutation detection can be performed also using qPCR techniques such as Allele specific PCR (ASPCR) or High resolution melting temperature PCR (HRM).

Example 2

Tumour-Derived Endothelial Microemboli Prevalent in Early Stage Colorectal Cancer Patients Patient samples and clinical data. All subjects had given informed written consent to participate. Clinical samples were obtained between July 2012 and April 2014 according to protocols approved by the Institutional Review Boards (IRB) of the National University of Singapore, Fortis Surgical Hospital and Singapore Health Services (SingHealth). Consecutive blood samples from 82 CRC patients were provided by Fortis Surgical Hospital (FSH) and National Cancer Center, Singapore (NCC). Blood samples from 45 healthy subjects were provided by the Singapore Consortium of Cohort Studies (SCCS). All samples were collected in EDTA Vacutainer tubes (Becton-Dickinson) and processed within 6 h at the Institute of Bioengineering and Nanotechnology. Two cases were excluded from analysis because of technical failure of the microfiltration device. Wherever available, matched tumour and metastatic samples were immediately frozen after resection, and stored at −80° C. until use. Clinicopathologic data for participating subjects are described in Supplementary Table 6 and were collected retrospectively after completion of CTM counts. Clinical data collection was conducted without prior knowledge of CTM counts. Similarly, clinical data for CRC patients were not known at the time of CTM count except for diagnosis and preoperative status of FSH samples. Tumour area was calculated by width×length.

Cell lines and culture. HCT 116, COLO 201, SW480, SW620, DLD-1 and RKO colorectal cancer cell lines, BJ-5ta immortalized human foreskin fibroblasts and HUVECs were from ATCC. HUVECs were used at passage 1 and 2 and cultured in EGM-2 medium (Lonza). All other cell lines were cultured in DMEM (Life Technologies) supplemented with 10% FBS. Cells were maintained in a humidified incubator at 37° C. in the presence of 5% $CO_2$.

Device fabrication and assembly. Silicon microsieves were fabricated as described (Lim et al). Briefly, the microsieve consists of a silicon disk having an overall diameter (ø) of 7.3 mm and a support ring of thickness 300 µm. The central capture region has ø 5.3 mm and 60 µm thickness containing 100,000 circular pores obtained by deep reactive ion etching. To embed the microsieve in a sterile 3-ml syringe, an acrylic sleeve insert was designed, consisting of an inlet channel of ø8.58 mm tapered to a ø5.54 mm channel, which corresponded to the microsieve cell capture region. The sleeve insert housed the microsieve and silicone O-rings (0.5 mm-thick) that ensured good sealing and cushioning as shown in FIG. 9b. The retrieval device was assembled as follow. Firstly, the rubber plug of a 3 ml syringe plunger was removed and a hole of 5.5 mm diameter was created using a punch cutter. The perforated rubber plug was placed in the 3-ml syringe. Next, an O-ring was placed in the slot of sleeve insert, followed by microsieve and another O-ring. Finally the sleeve insert with microsieve and O-rings was placed in the 3-ml syringe above the perforated rubber plug. This arrangement enabled the microfiltration of cells by size from whole blood and the subsequent retrieval of captured cells from the upper surface of microsieve in a convenient set-up.

Microfiltration. To optimize blood microfiltration, 5 µM CellTracker (Life Technologies) labelled cells were added to donor blood at 10-50 cells per ml of whole blood. Blood was filtered at various flow rates by means of a peristaltic pump (Ismatec). After 6 washes using PBS, 0.5% BSA and 2 mM EDTA, cells were resuspended in culture medium. Subsequently, cell nuclei were stained using Hoechst 33342 (Life Technologies), and cells were retrieved to determine retrieval efficiency and fold depletion of contaminating WBCs. In some experiments, CellTracker positive cells remaining on the microsieve were also counted.

Percent retrieval efficiency was calculated as follow:

% Retrieval Efficiency=(Retrieved cells)×100/ (Spiked Cells)

Fold depletion from 1 ml whole blood was calculated as follow:

Fold Depletion=(WBCs in Whole Blood)/(WBCs in Microfiltrate)

WBC count in microfiltrate is defined as the number of any Hoechst 33342 positive, CellTracker negative event in the case of experimental enrichment or by any CD45 positive event in the case of clinical sample analysis. All clinical samples were immediately processed for the indicated downstream applications using optimized parameters described in FIGS. 5b and c. To estimate ideal target WBC depletion, micromanipulation on serial dilution of PBMCs containing 50 CellTracker positive HCT 116 cells was performed. Five thousand fold depletion allowed micromanipulation of pure HCT 116 cells without contaminant white blood cells. The ideal target retrieval efficiency was chosen based on literature search on existing label-free CTC isolation devices (Cima et al). Microfiltration of clinical samples was performed using 2 ml whole blood for each device and optimized microfiltration conditions.

On-sieve immunofluorescence. Suspension cells were stained for 30 min directly 'on sieve' after 5 washes in PBS containing 0.5% BSA, 2 mM EDTA and human FcR Blocking Reagent (Miltenyi Biotec) using following fluorescent-labelled antibodies: anti-CD45 1:200 (clone 2D1; eBioscience), anti-Ep-CAM 1:20 (9C4, BioLegend), anti-CD31 1:20 (WM59, BioLegend), anti-CD144 1:10 (55-7H1, BD), anti-CD41 1:20 (HIP8, BioLegend) anti-CD42B 1:20 (HIP1, BioLegend). For intracellular antigens, the Inside Stain kit (Miltenyi Biotec) and human FcR Blocking Reagent were used with following antibodies: anti-VWF 1:200 (rabbit polyclonal A 0082, DAKO, conjugated in-house to Alexa 488 or Alexa 555 using Life Technologies APEX Antibody Labeling Kit), anti-Vimentin (V9, Santa Cruz Biotechnology), anti-pan Cytokeratin (C11, Cell Signaling Technology). Nuclei were stained using Hoechst 33342 (Life Technologies). In some experiments, Calcein AM (Life Technologies) was used to identify living cells. After a washing step, cells were retrieved and visualized in suspension under an inverted fluorescence microscope (IX81, Olympus) for imaging, counting and/or micromanipulation. Images were recorded using the MetaMorph software (Molecular Devices) with a CoolSNAP HQ2 CCD Camera (Photometrics).

CTM definition and count. CTM were defined in this study by "any CD45$^-$ cell or CD45$^-$ cellular cluster with a major axis of >10 µm and having at least 2 clearly distinct nuclei". In the studies described herein, all cells defined as such, stained positive for endothelial markers CD31, CD144 or VWF (FIG. 7b). Importantly, the cellular populations belonging to the megakaryocytic lineages, having large and lobulated single nuclei or large and round single nuclei, were excluded. These cells had characteristic cytomorphology easily discernible from CTM, stained positive for CD41 and CD42B, and were predominantly observed in CRC patients undergoing treatment, but also in some healthy volunteers and treatment-naive CRC patients. Single endothelial cells, owing to their smaller diameter that would allow them to pass through the microsieve, were also excluded from the analysis. CTM were counted by applying these inclusion and exclusion criteria by adding the microfiltrate obtained from 2 ml of whole blood to a well of a 96-well plate. After a short centrifugation step, CTM were identified and counted by manually scanning the target well three times using a 20× objective. A positive sample was defined by the detection of at least one CTM.

Target cell identification, micromanipulation and storage. Target cells were manually micropipetted using a mouth pipette attached to a 25-ml syringe. Briefly, cells were identified from total cell retrieval by means of bright field image, nuclear staining and specific fluorescent signals. Target single-cells or CTM were then micropipetted in a 10-µl droplet of wash buffer, followed by deposition in 0.2-ml PCR tubes containing appropriate buffer: 5 µl of 2× Reaction buffer (CellsDirect One-Step qRT-PCR Kit, Life Technologies) for scrmPCR, 2 µl of PBS for whole genome amplification or 2 µl of SuperBlock buffer (Thermo Scientific) for low-input RNA-Seq. Cells were stored immediately at −80° C. until use. In some cases, the complete microfiltrate was spun down, and stored at −80° C. until further use.

Single-cell RNA and mutational analysis PCR (scrmPCR). Primers were designed using Primer-BLAST (Ye et al). For each RNA transcript, primers were desginated either spanning exon-exon boundaries or primers separated by at least one intron on the corresponding genomic DNA region. Primers for mutational analysis were designed to bind intronic regions of the target gene (Tables 1A-C). The method for scrmPCR was highlighted in FIG. 1 as described in Example 1 above. This method could be used to simultaneously detect and quantify RNA transcripts and sequence DNA hotspots in the same cell. Briefly, single-cell RNA transcripts were reverse transcribed at 50° C. for 30 min using SuperScript III Reverse Transcriptase (Invitrogen) and a mix of 500 nM target reverse primers. A preamplification round (Table 1A) was then performed using Platinum Taq DNA polymerase (Invitrogen) by adding a matching mix of forward primers to the transcript-specific reverse primers and primers pairs for targeted genomic regions. Preamplification cycling was conducted by alternating annealing and denaturation steps without extension as follow: 6× cycles at 60° C., 4 min, 95° C., 1 min; 6× cycles at 55° C., 4 min, 95° C., 1 min; 6× cycles at 50° C., 4 min, 95° C., 1 min. Primers cleanup was performed using the Axyprep PCR Clean-up Kit (Axygen). Samples were diluted 1/20 and stored at −20° C. until further use. For RNA transcript quantitation, quantitative PCR was performed on a ViiA7 Instrument (Applied Biosystems) using 2 µl of preamplification reaction, semin-ested primer pairs according to the target transcript (Table 1B) and the SensiFAST SYBR Lo-ROX Kit (Bioline) following manufacturer's protocol. Relative gene expression was normalized using ACTB as reference gene. To analyze selected DNA mutational hotspots, PCR was performed by using 2 µl of preamplification reaction, nested PCR primer pairs (Table 1B) and a master mix containing a proof-reading polymerase (KOD Hot Start Master Mix, EMD Millipore) following manufacturer's instructions. For KRAS exon 2 sequencing in tumour and normal tissue (FIG. 4b), PCR amplification was performed using the following forward primer, TTTGTATTAAAAGGTACTGGTGGAG (SEQ ID NO: 135) and reverse primer, CCTTTATCTGTAT CAAAGAATGGTC (SEQ ID NO: 136). PCR products were separated on agarose gel; specific bands were excised and sequenced using the Sanger method.

Nucleic Acid Extraction. Complete microfiltrates or isolated cells were subjected to RNA extraction using the RNAqueous-Micro Total RNA Isolation Kit (Ambion) following manufacturer's instructions. Total RNA from tissues was isolated using the RNeasy mini kit (Qiagen). DNA from tissues was isolated using DNeasy mini kit (Qiagen).

CTM targeted resequencing and array comparative genomic hybridization (aCGH). Single-CTM were subjected to whole genome amplification using the GenomePlex Single-cell Whole Genome Amplification Kit (Sigma) and following manufacturer's instructions. Tissue DNA (50 pg) samples were amplified using the same procedure. For targeted resequencing, a custom gene panel targeting axons for NRAS, CTNNB1, PIK3CA, EGFR, BRAF, PTEN, KRAS, AKTI and TP53 genes (~6.1 kb) was designed. The libraries were constructed using Ion AmpliSeq Library Kits 2.0 (Life Technologies) with 10 ng of input DNA. Targeted resequencing run was performed on Ion Torrent Personal Genome Machine (PGM) Sequencer (Life Technologies). Variants were called using Ion Torrent Variant Caller Plugin in high stringency settings. aCGH was performed by hybridizing 250 ng of DNA to CytoScan 750 K arrays (Affymetrix) with manufacturer's instructions and reagents. Data were analyzed and visualized using Chas software version 2.1 (Affymetrix).

CTM and tissues cDNA synthesis and RNA-Seq. cDNA was synthesised from single-CTM and 10 pg of tissue RNA with the SMARTer Ultra Low RNA kit (Clontech Laboratories) using long distance PCR (LDPCR) with 25 cycles and 18 cycles respectively. For each sample, cDNA was sheared using the Adaptive Focused Acoustics system (Covaris). Libraries using NEBNext DNA Library Prep Master Mix kit (New England Biolabs) were constructed. All libraries were barcoded using unique indexes and pooled for RNA sequencing run on the Illumina HiSeq 2000 platform. Data were mapped to Human Genome version 19 (hg19) using Tophat (version 2) (Trapnell et al, 2009). Cufflinks (version 2.2) (Trapnell, C. et al, 2010) was used to quantify gene expression as FPKM (Fragments Per Kilobase of transcript per Million mapped reads).

RNA-Seq data principal component analysis. Principal component analysis on the complete RNA-Seq dataset (FIG. 16) was performed. Rank correlations coefficients were calculated by selecting the top 300 genes sorted by their maximum loading in the 1st to 3rd principal component. From this list, the Spearman rank correlation coefficient (p) was calculated for each CTM and tissues and the resulting data were plotted as a heatmap. Dendrograms were generated by average linkage clustering.

Figure 14A:
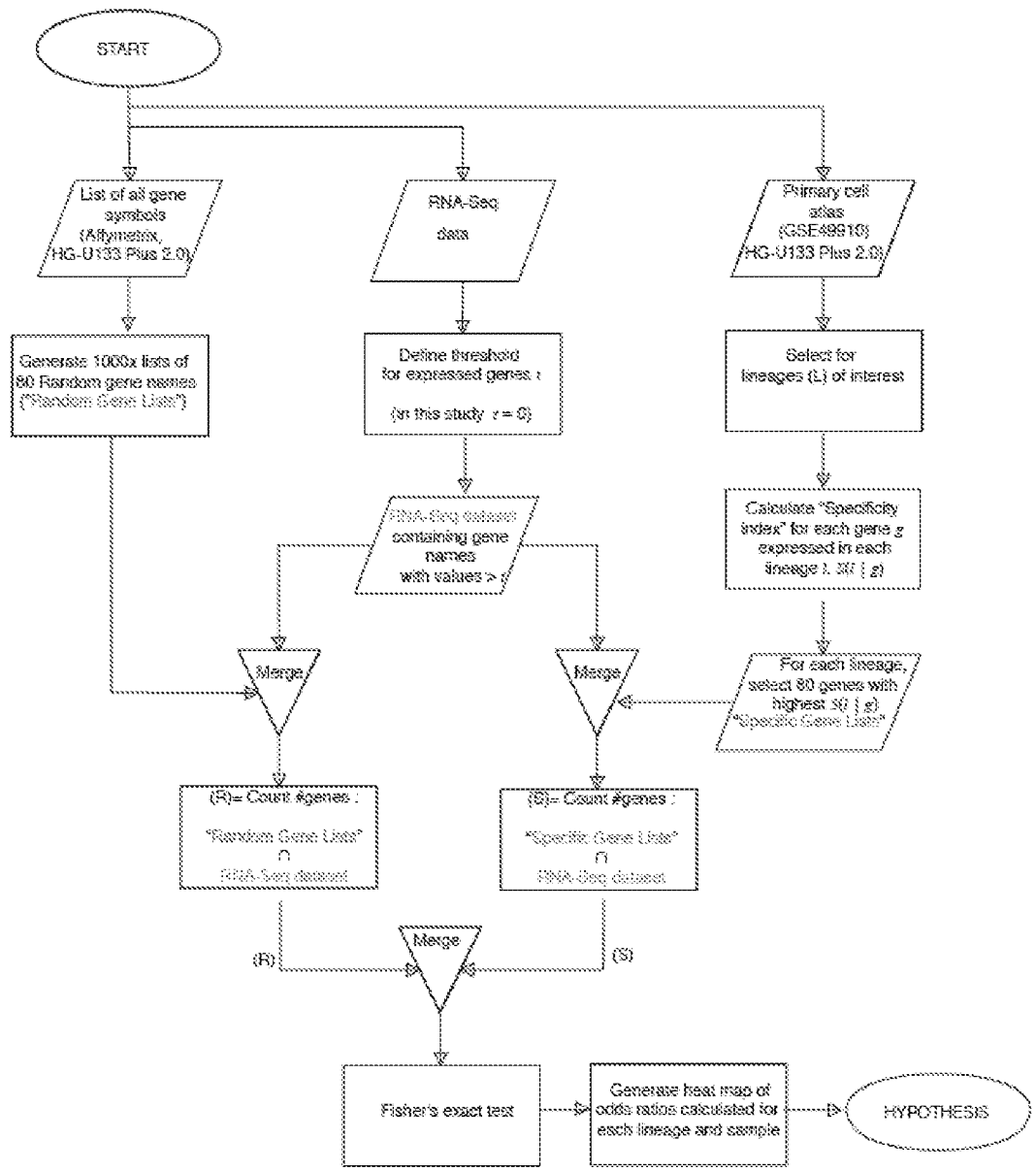
FIG. 14 shows a lineage inference workflow. (a) is a flow chart of the lineage inference workflow. (b) shows selected genes with highest specificity index for representative lineages are verified for specificity using BioGPS (Wu et al) (c) shows gene expression level of markers commonly used in CTC research to denote epithelial cells. Note KRT18 expression in the endothelial lineages and EPCAM expression in hematopoictic cells.
Figure 15:
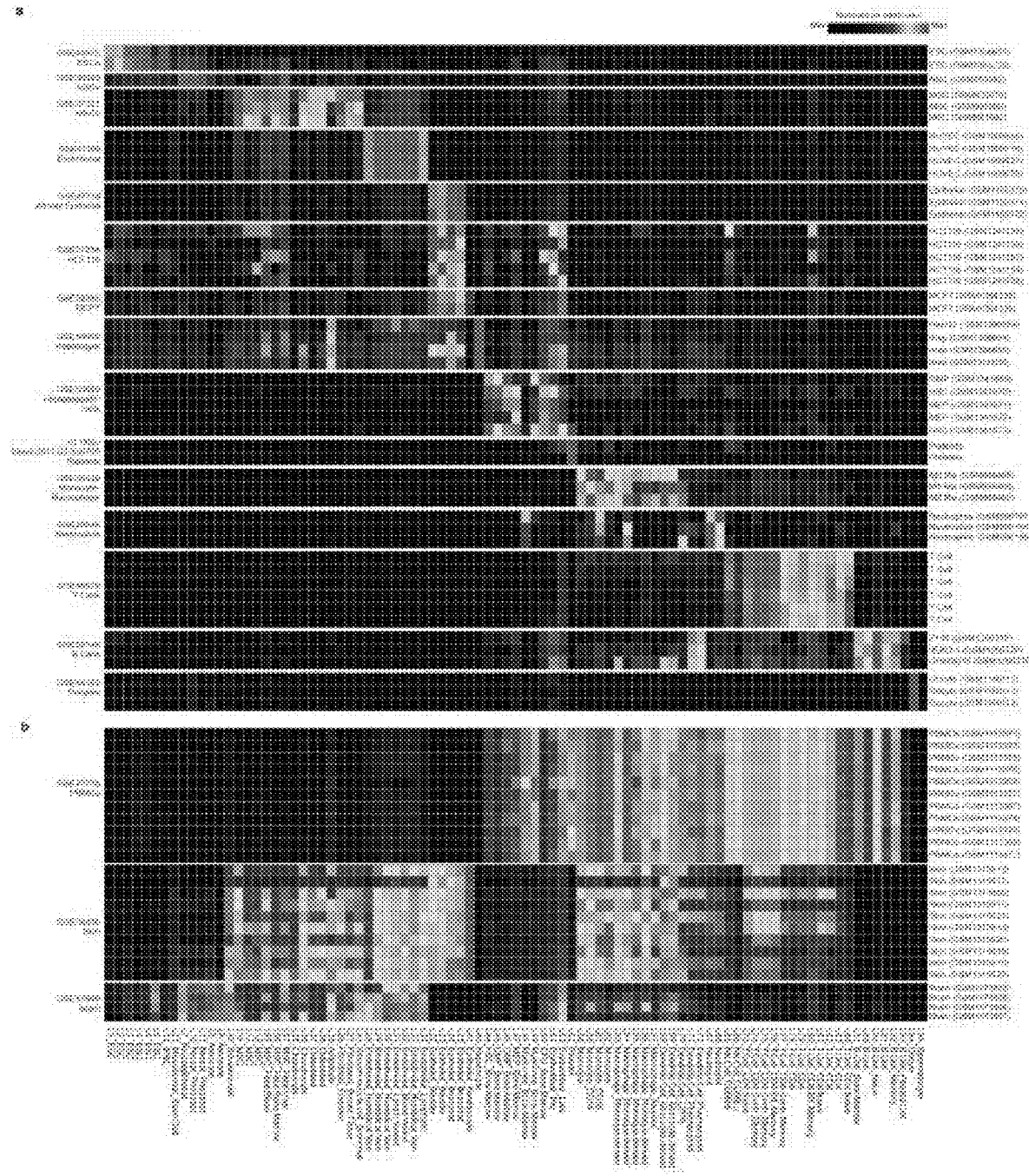
FIG. 15 shows a lineage inference algorithm validation. (a) shows heat maps comparing number of genes enriched for each sample (rows) and lineage (columns) over random enrichment. Samples are published RNA-Seq data from selected lineages. Each coloured box represents a normalized odds ratio of the respective Fisher's exact test from 0 (black) to 1 (light grey). (b) Same as in (a), except that whole tissues or complex cell mixtures such as PBMCs, skin and brain datasets are used.

RNA-Seq data lineage inference. Workflow for lineage inference is presented in FIG. 14a and was implemented in an R script. Briefly, the primary cell atlas dataset (GSE49910) (Mabbott et al) was obtained and expression data from 298 different experiments were selected, corresponding to N=42 different cell types or 'lineages'. For each gene g in each lineage l, a 'specificity index' S was calculated based on Shannon information entropy and the Q statistics introduced by Schug et al., $$S_{(l|g)} = -\sum_{l=1}^{N} p_{(l|g)} \cdot \log_2(p_{(l|g)}) - \log_2(p_{(l|g)})$$

where p(l|g) is the relative expression of the gene g in the lineage l. Gene specificity was confirmed by visualizing expression data of genes with high specificity index using BioGPS (FIG. 14b). For each lineage the top 80 genes with highest specificity index ('specific genes') were selected. 80 genes were chosen as this provided the best resolution in the analysis reported herein. Next, for each RNA-Seq sample, the number of genes specific for each lineage was calculated. At the same time, 1,000× lists of 80 randomly selected genes were generated from the Affymetrix HG-U133_Plus_2 gene list ('random genes') and the average number of genes present by chance in each experimental RNA-Seq profile was determined. Finally, it was examined whether the number of enriched specific genes was equal to the number of randomly enriched genes by performing a Fisher exact test for each tested lineage in each experimental sample. The odds ratios for each test were mean-centered, scaled and visualized in a heat map comprising all tested lineages. The final results were used to generate hypotheses on cellular lineages based on the distribution of the normalized odds ratios. The algorithm was validated using published RNA-Seq datasets generated from various cell types and tissues (FIG. 15).

Endothelial progenitor cell (EPC) assay. Colony-forming EPC assay was performed as previously described (Kalka et al, Colombo et al). Briefly, living endothelial CTM were counted in 2-ml microfiltrates by CD144 and Calcein AM fluorescent staining. Unstained microfiltrates from 2 ml of blood from a second device was then placed in culture on 96-well plate coated with fibronectin (1 µg/cm$^2$) (Sigma-Aldrich) in the presence of EGM-2 cell culture medium (Lonza). Presence of CTM was confirmed by bright field microscopy before incubation. HUVECs were used as positive control as follow: 10,000 HUVECs were spiked in 2 ml of donor blood and isolated by microfiltration using two devices. In one device, retrieved HUVECs were quantified by CD144 and Calcein AM staining. HUVECs retrieved from the other device were seeded at defined numbers (5, 10, 20, 40, 80 and 160 cells) in octuplicate wells. After 2 days, the medium was changed and cells were allowed to grow for a total of 30 days by changing half of the medium every other day. Presence and viability of colonies were monitored every week under bright field microscopy. After 30 days, cells were detached by trypsinisation, stained using CD144 antibodies, Calcein AM and Hoechst 33342, and quantified under an IX81 (Olympus) inverted fluorescence microscope.

Microvessel density and lumen count. Microvessel density (MVD) count was performed using immunofluorescence images of CD31-stained tissue sections as described previously (Wild et al, Gupta et al) and using ImageJ (Schneider et al). Briefly, fresh tissues were embedded in Tissue-Tek O. C. T Compound (Sakura) and stored at −80'C until further use. From all available tissues, five-micrometer cryostat sections were cut on poly-L-lysine slides, fixed in PBS containing 4% paraformaldehyde for 8 min, washed in PBS, and stained using PE-anti-CD antibodies (1:20, clone WM59, BioLegend). The whole tumour area for each tissue section was imaged with a 10× objective by means of an IX71 microscope system (Olympus) and the MetaMorph software (Molecular Devices). Before imaging and throughout MVD and lumen count, patient's IDs were blinded to avoid subjective bias during data acquisition and analysis.

Endothelial cell isolation from fresh tissues. Endothelial cells were isolated from normal colon and tumour tissues as previously described (Van Beijnum et al) with minor modifications of the protocol. Briefly, fresh tissues were minced and digested for 60 min at 37° C. using collagenase, dispase and DNAse as described. After a Ficoll-Paque density centrifugation step, a two-step magnetic selection was performed using MACS reagents and materials (Miltenyi Biotec) following manufacturer's instructions. First, CD45-expressing cells were depleted by negative selection in LD columns, after labelling the cells with anti-CD45 magnetic beads and Human FcR Blocking Reagent. The CD45-depleted fraction was next collected and a second labelling was performed by adding anti-CD31 magnetic heads and human FcR Blocking Reagent. After a positive selection using MS columns the fraction with enriched CD31$^+$CD45$^-$ cells was stored at −80° C. until further use.

Statistical analysis. Statistical analysis was performed in R environment (version 3.1.0) (R Core Team et al). Unpaired samples were tested using two-tailed Wilcoxon-Mann-Whitney U test with Bonferroni correction in case of multiple comparisons. For each test, exact P value with location parameter (Hodges-Lehmann estimate $\hat{\Delta}$) and its 95% confidence interval (CI) were computed using the 'coin' package (Zeilcis et al). For paired samples, a two-tailed exact Wilcoxon signed-rank test was used. ROC curves with AUC and 95% CI intervals were computed using the 'pROC' package (Robin et al). For easy interpretation and comparison of effect sizes, the effect size r for each statistical test was derived as follows: $r=|Z|/\sqrt{n}$ where Z is the Z score of the Wilcoxon-Mann-Whitney U or the Wilcoxon signed-rank test (Rosenthal, et al). r from AUC was derived as described in Rice & Harris (Rice et al). As introduced by Cohen (Cohen et al), the following interpretations were applied: r=0.1, small effect; r=0.3, medium effect; r=0.5, large effect. Boxplots are shown as boxes representing the interquartile range (IQR) with a line across the box indicating the median, whiskers indicate 1.5×IQR. To derive the minimal sample size required to the case control study, it was first assumed there was no association between presence of CTM and presence of CRC (null hypothesis) and for a target power of 0.95, a minimal sample size of n=72 was estimated using the pwr.chisq.test function of the 'pwr' package (Champely et al). An effect size w=0.5 at the significance level of 0.01 was assumed, where w=0.5 was chosen based on a pilot test of five CRC patients (FIG. 10b), information derived from four healthy controls with negative CTM counts and a review of the literature that reported no CTM in healthy individuals but widespread presence of CTM in cases in various cancer types (Supplementary Table 1). Correlations in FIG. 18 were tested using Kendall's tau (T) coefficient and its derived P value. For lineage inference and principal component analysis of RNA-Seq data, Fisher's exact tests and Spearman correlation coefficient (p) were used respectively, as described in the dedicated method paragraphs. Level of significance was set at 0.05. One asterisk (*), P<0.05; two asterisks (), P<0.01; three asterisks (*), P<0.001; not significant (ns), P≥0.05.

Results of Analysis

Circulating tumour microemboli (CTM) are clusters of cells commonly observed in blood sampled from cancer patients. CTM have been generally described as malignant entities for over 50 years and their investigation might yield insights on tumour progression and clinical outcomes. However, comprehensive characterization of these structures has not yet been presented. Here it is shown that contrary to current consensus, CTM isolated from colorectal cancer patients are not cancerous but represent a distinct population of tumour-derived endothelial cells. CTM do not mirror the genetic variations of matching tumours, yet CTM express epithelial and mesenchymal transcripts in agreement with previous reports on circulating tumour cell phenotyping. Transcriptome analysis of single-CTM reveals their identity as endothelial cells with further results indicating their tumor origin and mature phenotype. Widespread presence of endothelial CTM was found in blood sampled from preoperative, early stage cancer patients but not in healthy donors, suggesting endothelial CTM count as potential indicator for colorectal cancer. Endothelial CTM should not be confused with bona fide circulating tumour cells although their analysis might be helpful diagnostically, and provide direct information on the underlying tumour vasculature during treatment and disease course.

Figure 5:
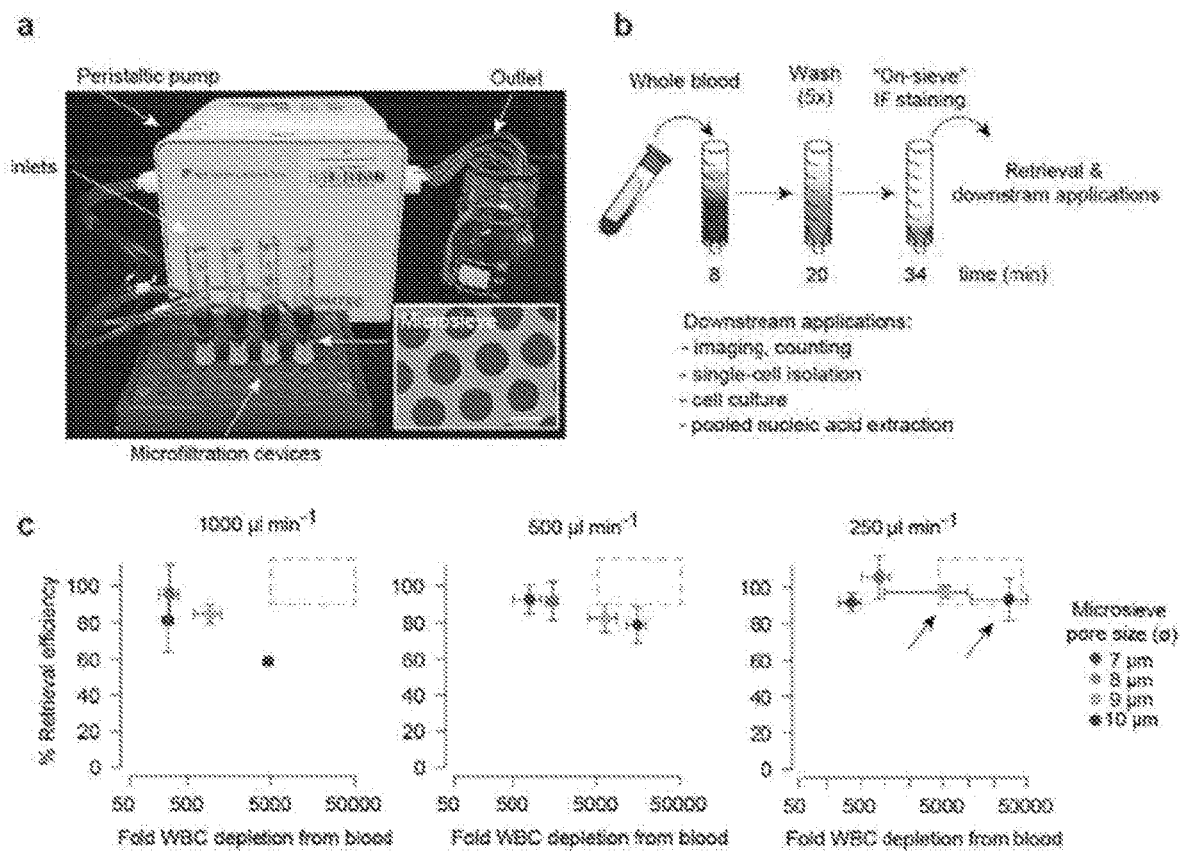
FIG. 5 shows the retrieval of circulating tumour cells using a microfiltration device. (a) shows the device setup. Microfiltration devices enclosing a silicon microsieve (inset, scale bar=10 µm) are connected to a peristaltic pump for flow rate control. (b) shows the microfiltration procedure for various downstream applications. The numbers indicate procedure time for each step. (c) shows optimization of retrieval efficiency and purity for downstream single-cell micromanipulation. The individual scatter plots represent experiments using various flow rates and microsieve pore diameters. Black dashed rectangle indicates the target area of >90% retrieval efficiency and >5×10$^3$ WBC depletion for optimal downstream handling of retrieved cells. Data points are means±s.e.m. of three independent experiments under each condition.
Figure 10:
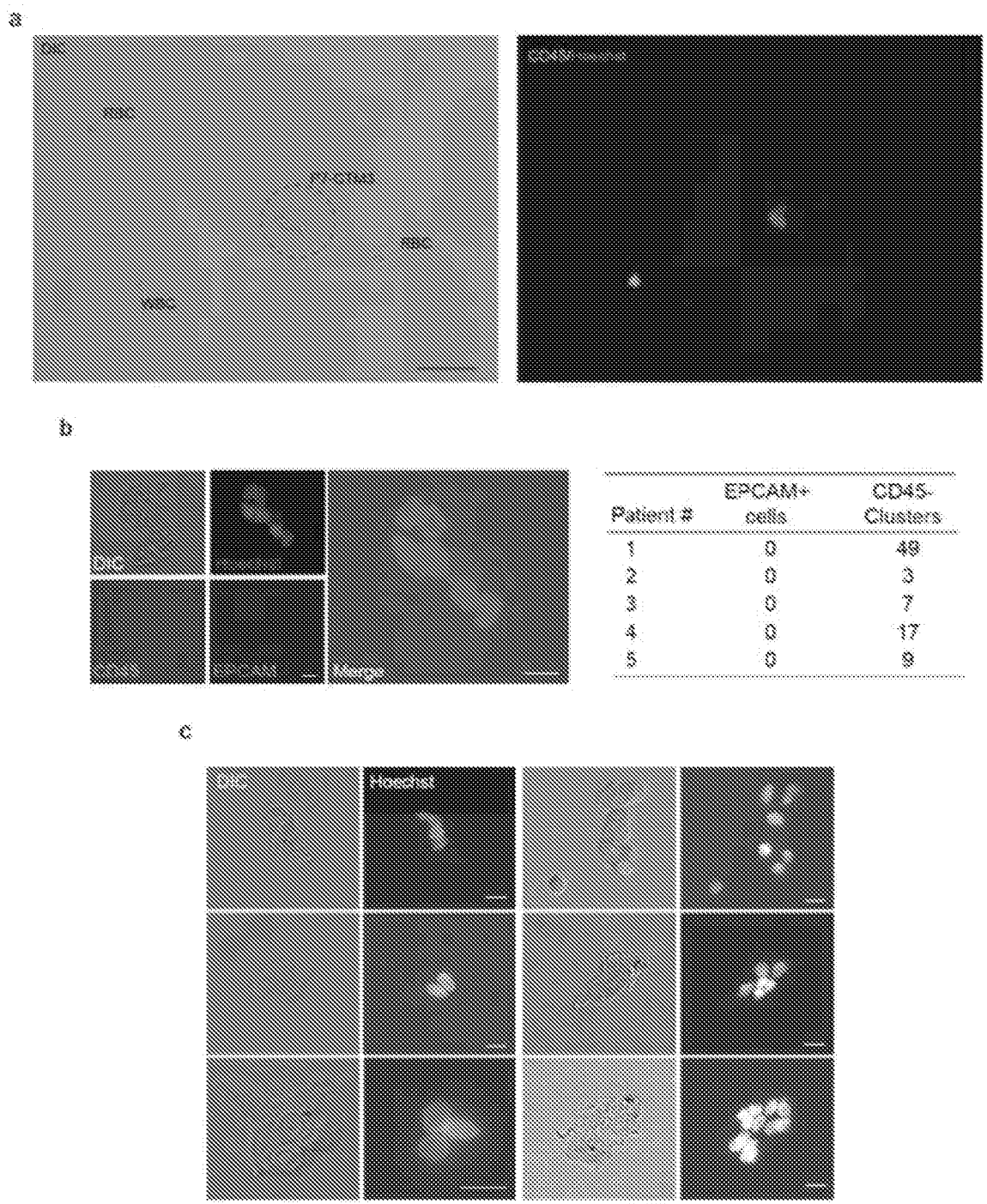
FIG. 10 shows characterization and definition of CTM. (a) shows a representative uncropped image of a CD45$^-$ CTM (P7-CTM3, sec also FIG. 1, FIG. 4a and FIG. 6a) in 100 of wash buffer, indicating purity of sample suitable for downstream analysis, and showing the presence of target CD45$^-$ CTM and sparse RBCs and a WBC, before final micromanipulation (Sec Methods). Scale bar 50 μm. (b) shows representative immunofluorescence of CD45 and Ep-CAM of CTM retrieved from 5 CRC patients. The table indicates CD45$^-$ CTM counts for each staining and patient. Scale bars=10 μm. (c) Representative cytomorphology of CTM. Scale bars=10 μm. DIC: differential interference contrast.

To analyze transcriptional and genetic profiles of circulating tumour cells (CTCs), a label-free, size-based microfiltration device that enables both retrieval and downstream micromanipulation of CTCs (FIG. 5a, b and FIG. 9a-c). was developed. CTC enrichment and retrieval efficiency was optimised by spiking 1 ml of donor blood with 30 SW620 cells, a colorectal cancer (CRC) cell line with similar median size as CTCs (FIG. 9d). An optimal tradeoff between retrieval efficiency and cell purity was obtained using a flow rate of 0.25 ml min$^{-1}$ and pore sizes of 9-10 μm. This resulted in >90% SW620 retrieval efficiency with >5×10$^3$ fold depletion of white blood cells (FIG. 5c), allowing for a variety of downstream applications beyond cell counting (FIG. 5b, FIG. 9f and FIG. 10a). Similar results were obtained using additional CRC cell lines (FIG. 9f).

Figure 4:
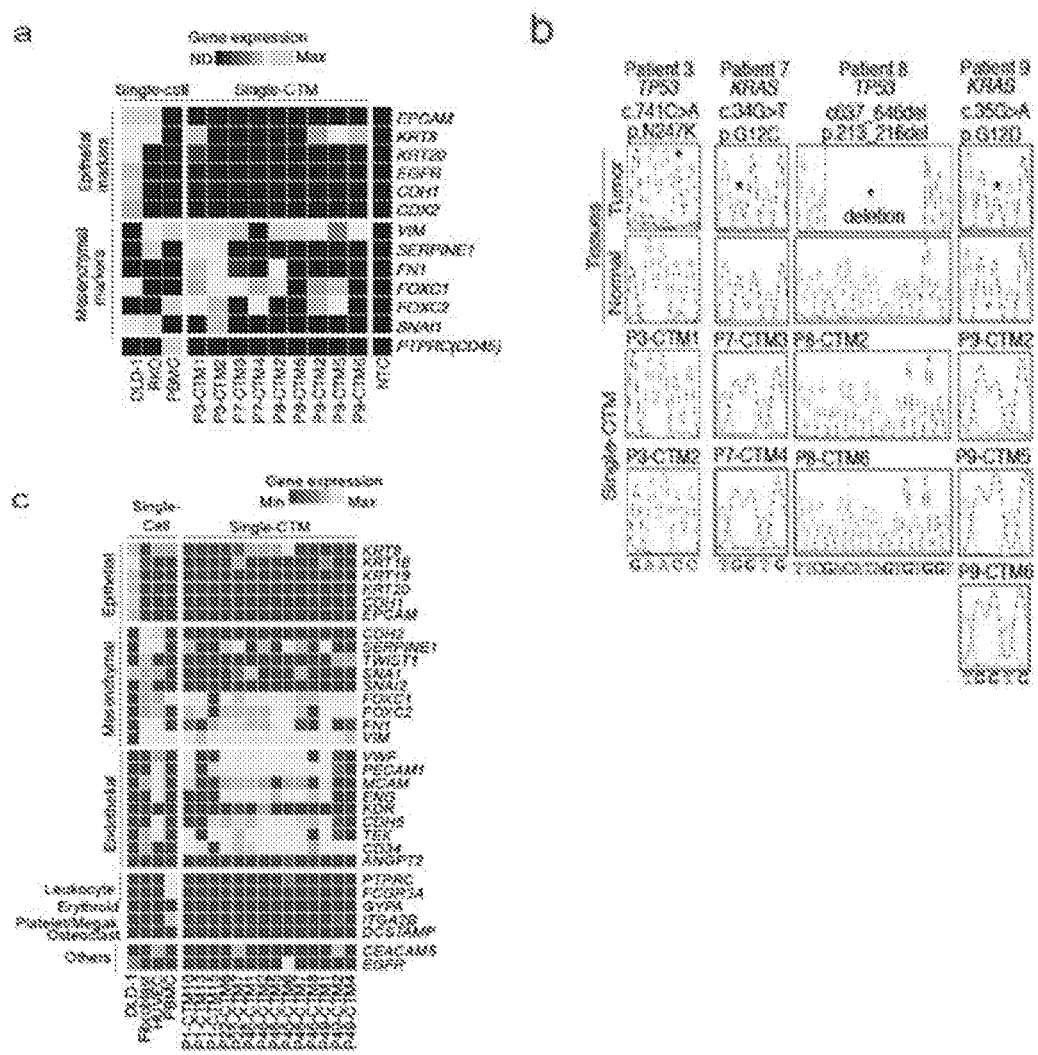
FIG. 4 provides the proof of principle for the scrmPCR method of the disclosure using single cells and single clusters of cells isolated from clinical samples. Single cells or single clusters of unknown origin isolated from blood of colorectal cancer patients were micro-manipulated and subjected to scrmPCR as described herein. In (a), the gene expression of several epithelial and mesenchymal markers shows the predominant mesenchymal nature of single clusters. The expression of PTPRC (CD45) is also shown. Colours represent gene expression from absent (dark grey) to maximum (light grey). NTC, no template control. In (b), results of Sanger sequencing of targeted gene region mutated in matching colorectal cancer tissues show that the same clusters shown in (a) do not contain mutations and are thus not related to the tumor epithelium. (c) shows the use of the latest scrmPCR protocol containing additional assays to quantify transcripts from a set of clusters, to show that clusters express transcripts belonging to the endothelial lineage. Heat map represents scrmPCR gene expression in control single-cells and 14 CTM (n=4 patients). Color scale indicate gene expression from low or absent (dark grey) to high (light grey).
Figure 6:
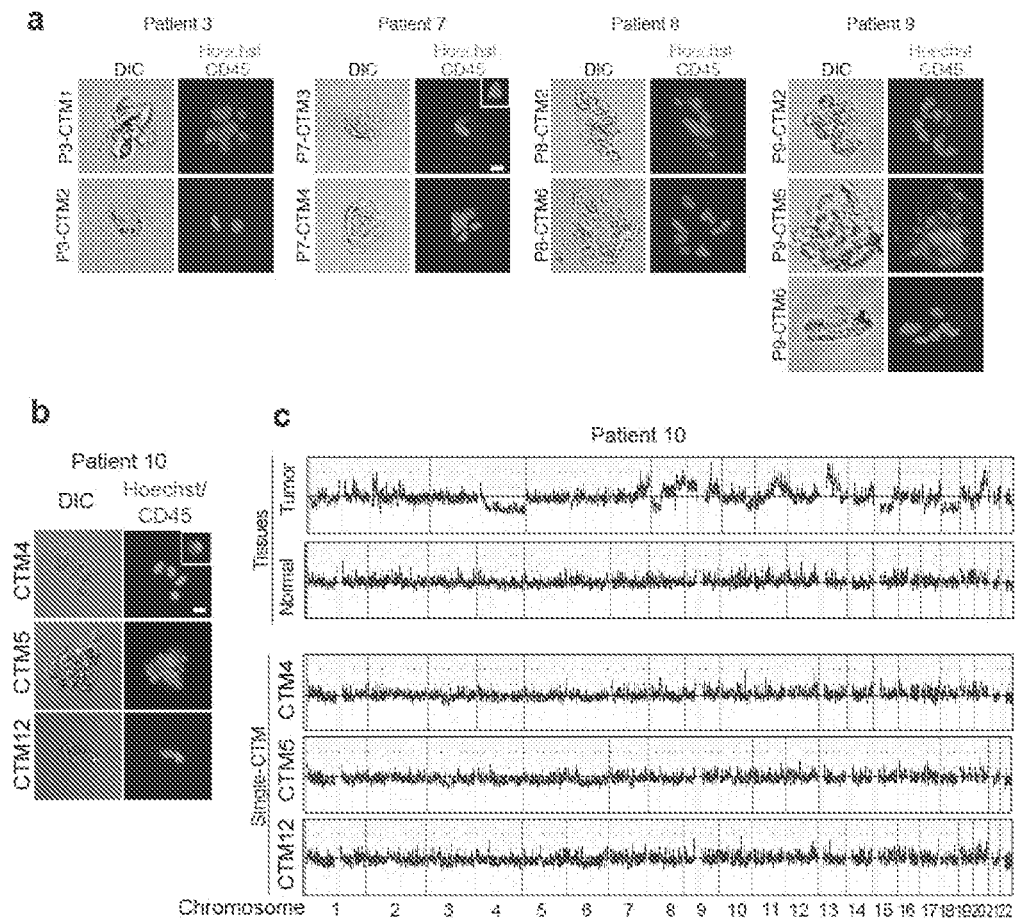
FIG. 6 shows that CTM express EMT markers, but do not mirror primary tumour mutations or chromosome abnormalities. (a) shows images of nine CTM from 4 CRC patients with known primary tumour mutations micro-manipulated in single tubes for downstream scrmPCR. (b) CTM aCGH shows images of three CTM from a representative CRC patient with known chromosomal abnormality. (c) shows aCGH analysis of CTM shown in (b) with matching normal and tumour tissues.
Figure 11:
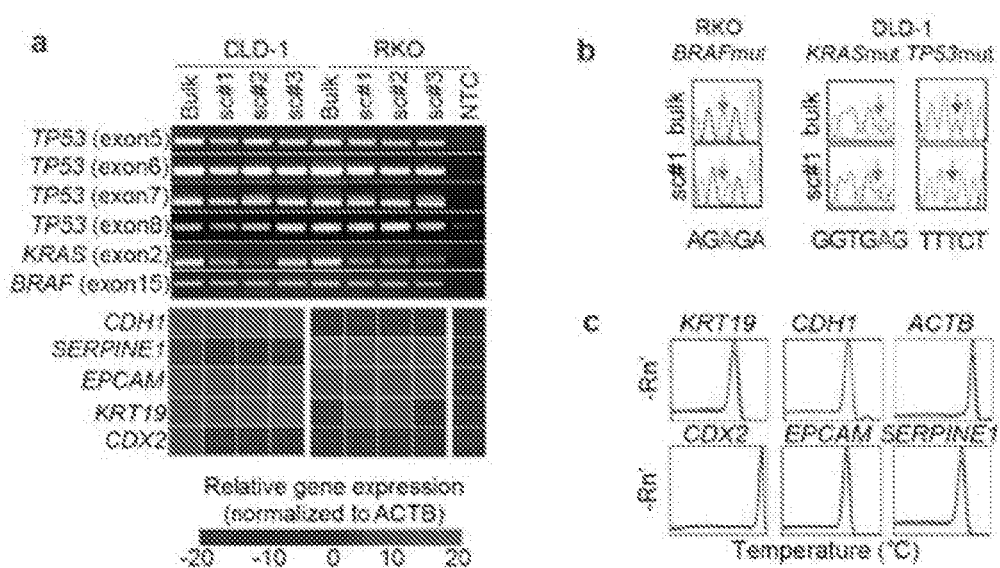
FIG. 11 shows scrmPCR proof of principle using an epithelial-like (DLD-1) and a mesenchymal-like (RKO) CRC cell line. (a) shows DNA amplification (gel electrophoresis) and RNA quantitation (heat map) for the indicated genes and single or hulk cells. (h) shows sequence chromatograms from DNA hotspots of known mutant alleles in RKO and DLD-1 single-cells. (c) shows melt curve plots of the indicated genes from qPCR reactions. sc, single-cell. NTC, no template control. Rn, normalized reporter signal

Microfiltrates derived from a pilot series of five patients were next tested and stained for epithelial cell adhesion molecule (hp-CAM), a canonical CTC marker, and CD45, a marker for white blood cells. Ep-CAM positive cells were not detected. However, it was noted that there were large aberrant clusters of Ep-CAM$^-$/CD45$^-$ cells present (FIG. 10b). First described in 1959, many studies have reported malignant circulating cell clusters or circulating tumour microenaboli (CTM) (Supplementary Table 1). The CTM that have been isolated displayed similar cytomorphology consistent with malignancy such as atypical nuclei, prominent nucleoli, and high nuclear-to-cytoplasmic ratio (FIG. 10a-c). In addition, lack of hp-CAM staining suggested a drift from the epithelial phenotype, an event previously reported for CTCs. It was therefore hypothesized that CTM harboured DNA alterations mirroring the primary tumour. To confirm the presence of DNA mutations in single-cells undergoing epithelial-mesenchymal transition (EMT), the polymerase chain reaction (PCR) protocol as described herein was established for the simultaneous quantitation of RNA transcripts and detection of DNA mutations at the single-cell scale (Single-cell RNA and Mutational Analysis PCR or 'scrmPCR') (FIG. 1, FIG. 11, Tables 1A-1C). scrmPCR in 9 CTM derived from 4 patients revealed the presence of epithelial and mesenchymal markers including SERPINE1, FOXC1 and KRT8, in line with epithelial-mesenchymal profiles reported previously for breast cancer CTCs (FIGS. 4a and 6a). These results were confirmed by panCK and Vimentin immunostaining (FIG. 11a and Cima et al). These CTM were next sequenced for mutations present in the corresponding primary tumours. Surprisingly, all tested DNA sequences hotspots matched the wild-type alleles (FIG. 4b). Targeted high-throughput DNA sequencing was further applied to 8 commonly mutated genes in DNA amplified from 16 single-CTM (6 patients) and matching tumour tissues. Again, matching mutations between tumour tissues and associated CTM (Supplementary Tables 2 and 3) could not be detected. Using amplified DNA from 12 CTM (4 patients), array comparative genomic hybridization (aCGH) was next performed. In fact, CTCs from lung cancer patients have been shown to reproducibly mirror cancer tissue copy number variations (Ni. X, et al). Here, the CTM had instead normal cytogenetic profiles in contrast to matched primary tumours (FIG. 6b-c and FIG. 11b-c). In summary, single-cell scale analysis of 26 CTM from 10 patients, while displaying epithelial-mesenchymal marker expression, did not mirror DNA anomalies found in matching tumour tissues. This suggested a source for CTM that was unrelated to the tumour epithelium.

Figure 12:
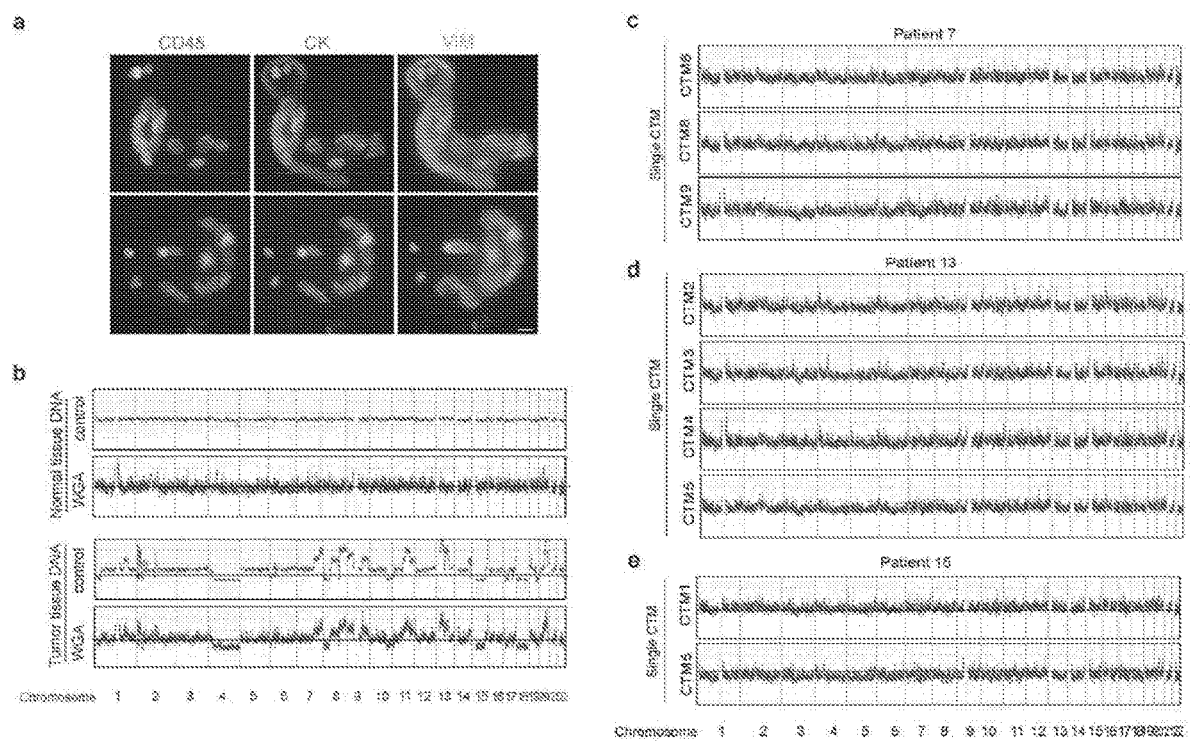
FIG. 12 shows that CTM express EMT markers but have normal chromosomal structures. (a) shows representative 4-colour immunofluorescence of two CTM for CD45, Vimentin (VIM), pan-Keratin (CK) and DAPI, indicating heterogeneous mesenchymal and epithelial markers expression. (b) shows a control experiment to assess the impact of whole genome amplification (WGA) for aCGH experiments using single-cells. (c-e) each shows aCGH of single-CTM for the indicated patients similar to normal tissue DNA shown in (b).
Figure 13:
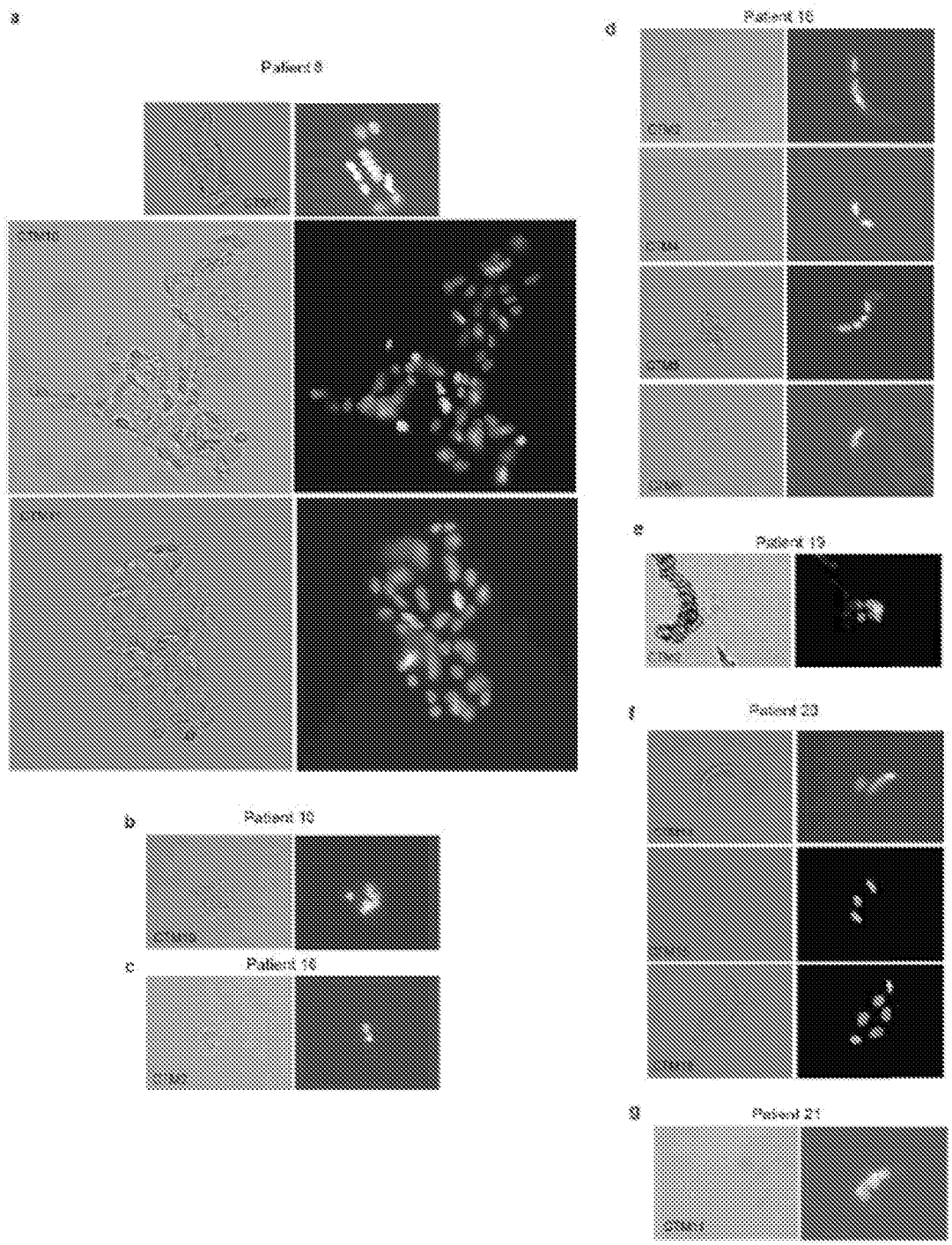
FIG. 13 shows that cytomorphology of CTM used for RNA-Seq. (a-g) each shows differential interference contrast (DIC) and Hoechst 33342 images of CTM used for RNA-Seq for each respective patients. No images are available for patient P1.
Figure 16:
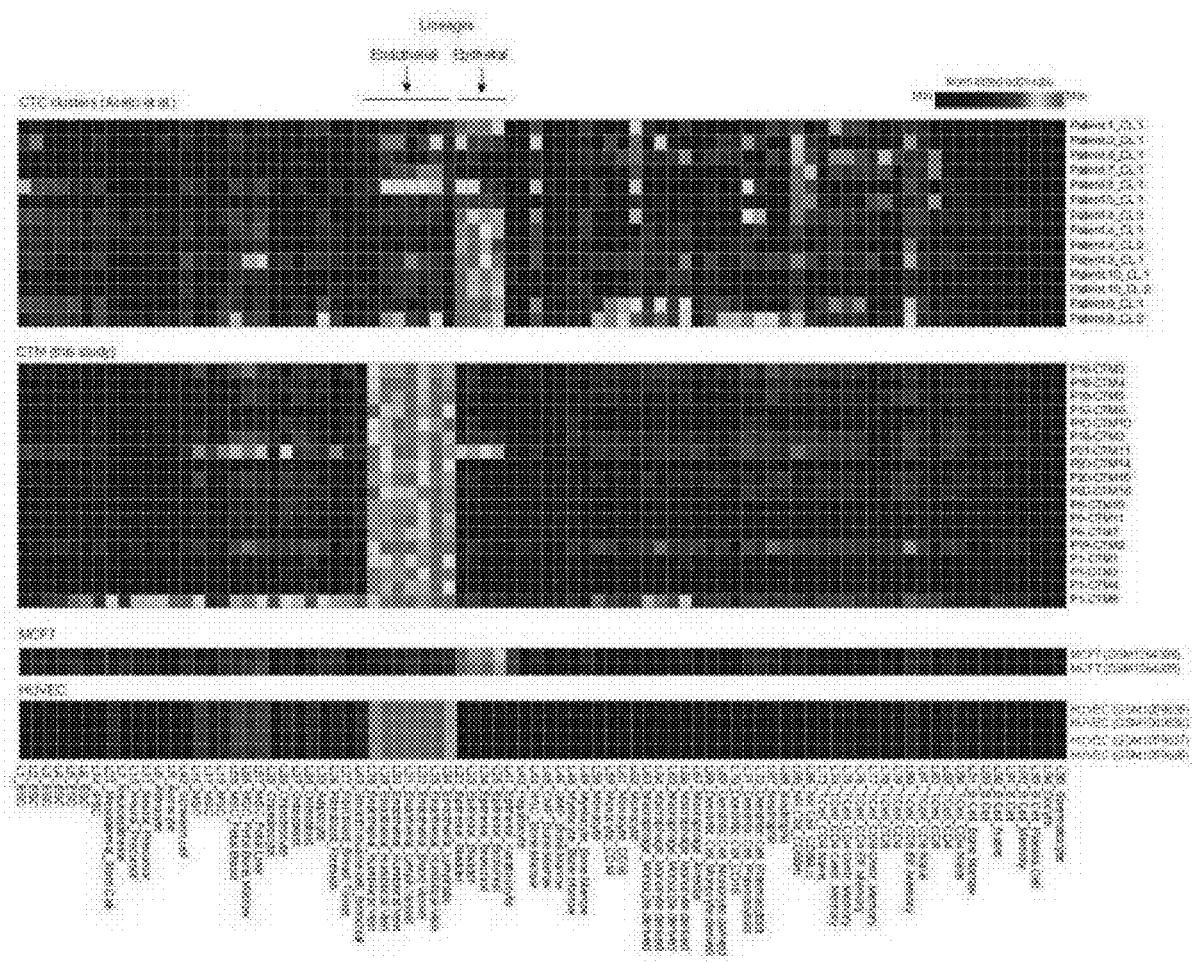
FIG. 16 shows a comparison between CTM and CTC-clusters reported in Aceto et al. Lineage inference of CTC clusters data from Aceto et al. shows enrichment with epithelial cell types. Platelet and red blood cell signals were removed from this analysis. RNA-Seq data from CTM analyzed in this study are shown for comparison. MCF7 and HUVEC RNA-Seq are shown as positive controls.

Next, 18 single-CTM from 8 patients and matching normal colon and tumour tissues were subjected to RNA expression profiling by high-throughput sequencing (RNA-Seq) (FIG. 12, FIG. 16, Supplementary Table 4). A workflow for the inference of cellular lineages from transcriptional profiles was further developed (FIG. 14, FIG. 15). In a comparison including 42 different cell types, all CTM transcriptomes were associated with the cell types of the endothelial lineage (FIG. 7a). The presence of a series of endothelial lineage markers together with general EMT markers by scrmPCR was confirmed in an additional 14 CTM (FIG. 4c). Endothelial cells are considered a specialized epithelium, and are known to express both Vimentin (often used as a mesenchymal marker) and various keratins (classic markers of epithelium). All CTM, including those with malignant cytomorphology, stained without exception for endothelial markers such as CD31, VWF or CD144 (FIG. b) but were negative for CD45 or markers of megakaryocytic lineages CD41 and CD42B. This indicated that in the CRC patients, all CTM detected were of endothelial origin. In addition, single tumour cells within CTM were not detected as reported previously elsewhere. The present findings were in line with El-Heliebi et al., who reported CD31 expression on circulating non-hematologic cells (CNHC) from kidney cancer patients, but were dissimilar from a recent report that described CTC clusters of malignant origins (Aceto et al). Lineage inference from the RNA-Seq data of CTC-clusters described in Aceto et al. in fact indicated the presence of epithelial derived cells (FIG. 15). CTM characterized in the present study represented thus a distinct population of circulating endothelial cell clusters in CRC patients.

Figure 17:
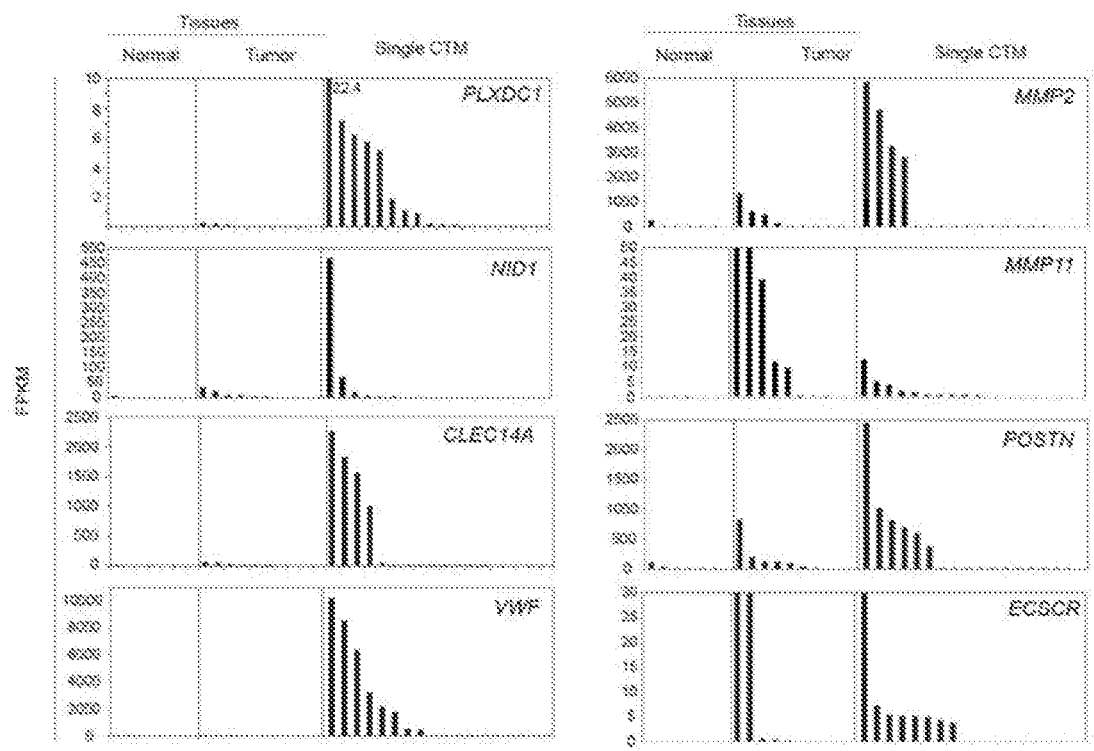
FIG. 17 shows tumour endothelial markers expressed in CTM. Additional tumor endothelial markers were expressed in normal, tumour tissues and CTM using RNA-Seq data. PLXDC1, plexin domain containing 1 (tumor endothelial marker 3/7) (St Croix et al); MMP2, matrix metallopeptidase 2 (St Croix et al); N1D1, nidogen 1 (St Croix et al); MMP11 (St Croix et al), matrix metallopeptidase 11; CLEC14A, C-type lectin domain family 14, member A (Mura et al); POSTN, periostin (Borgia et al); VWF, von Willebrand factor (Zanetta et al); ECSCR, endothelial cell surface expressed chemotaxis and apoptosis regulator (Herbert et al).

An endothelial progenitor clonogenic assay (Kalka et al and Colombo et al) revealed a mature phenotype for CTM as living CTM failed to proliferate on fibronectin substrate over a 30-day period (FIG. 7c). Principal component analysis of CTM-derived RNA-Seq data showed stronger associations with the tumour tissue transcriptome as compared to the normal colon tissue transcriptome (FIG. 7d). To test if CTM were tumour-derived, paired samples from 17 CRC patients 0-24 h before and 24-72 h were collected after surgical tumour resection (n =34). Tumour removal caused a sharp decline of endothelial CTM, supporting the direct link between the tumour and CTM (FIG. 7e and Supplementary Table 5). Folate hydrolase (FOLH1), the gene encoding for prostate-specific membrane antigen (PSMA), is specifically expressed in tumour vasculature of various cancer types, but absent in normal vasculature and peripheral blood. FOLH1 was indeed expressed in $CD31^+CD45^-$ cells isolated from fresh CRC tissues and in CTM isolated from the blood of 7/10 CRC patients, but not in endothelial cells isolated from normal tissues or in healthy donor peripheral blood mononuclear cells (PBMCs). This result further supported the tumour origin of endothelial CTM (FIG. 7f). Additionally, RNA-Seq data of CTM revealed the expression of several tumour endothelial markers, including CD276 (FIG. 7g and FIG. 17). It was further asked whether CTM numbers might correlate with features of the underlying tumour vasculature, by counting blood vessels in tumour tissues derived from patients with low or high CTM count. Although the median number of vessel units did not differ, the median number of lumens was significantly higher in patients with high CTM counts (FIG. 7h). Taken together, it was shown that CTM in colorectal cancer patients were not malignant entities but clusters of tumour-derived mature endothelial cells.

Figure 18:
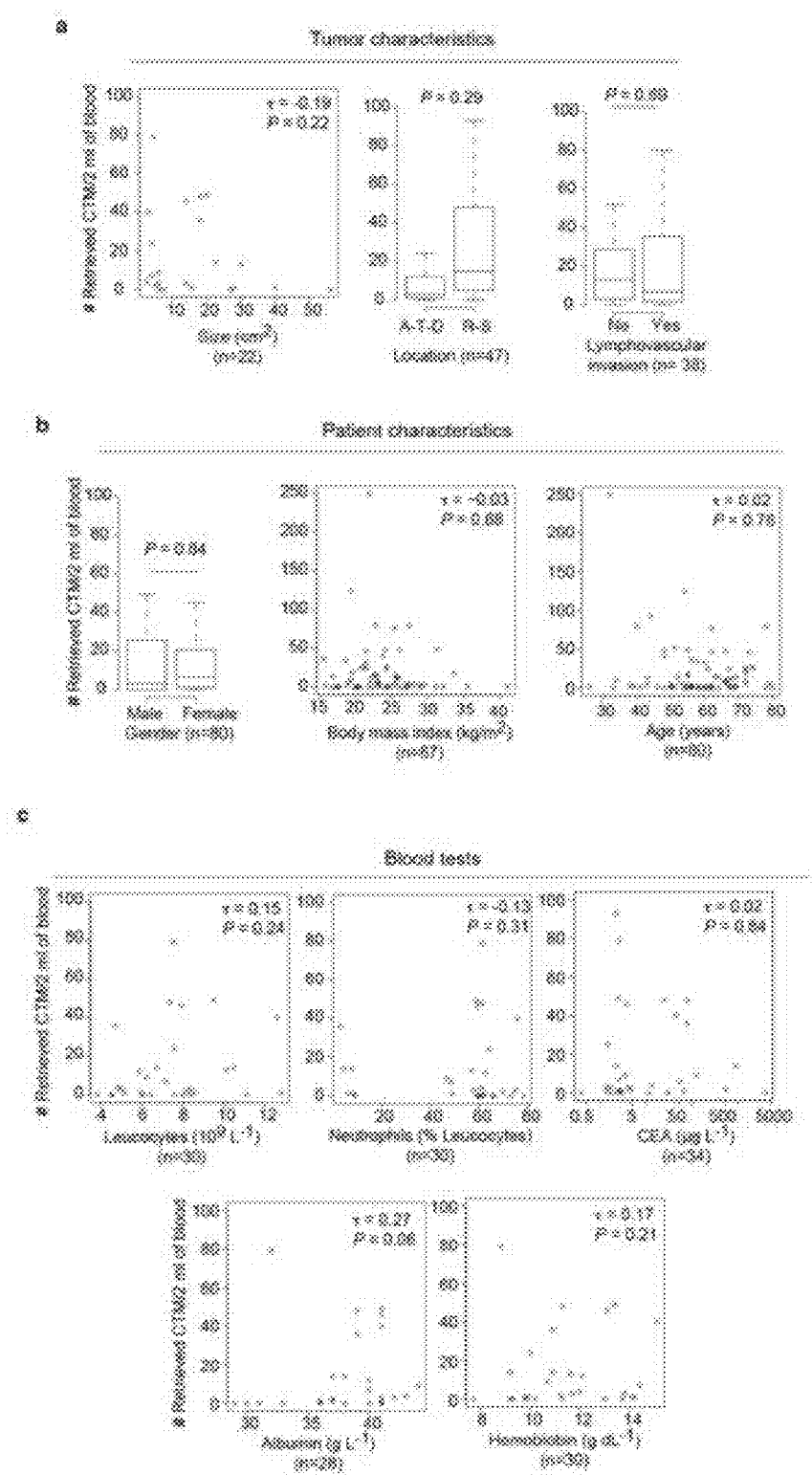
FIG. 18 shows that CTM counts do not correlate with inflammatory markers or other variables. (a-c) show the association of CTM number with the indicated tumour characteristics, patient's characteristics, and blood test values respectively. Correlations are shown as dot plots and measured using the Kendall's z coefficient and its derived P value. Comparisons of dichotomized variables are shown as boxplots and differences are quantified using P values from two-tailed exact Wilcoxon-Mann-Whitney U tests.

Because of the above-described associations between CTM and the primary tumour, it was next asked if endothelial CTM were informative indicators of CRC. Endothelial CTM from a total of 141 clinical specimens from 125 subjects (45 control healthy volunteers and a consecutive series of 80 CRC patients, including CTM counts from above-mentioned patients) were counted. At least one endothelial CTM in 76.2% (61/80) of CRC patients but only in 2.2% (1/45) of healthy individuals was observed (FIG. 8a). It was found that treatment-naive patients presented with significantly higher endothelial CTM counts as compared to patients that underwent therapeutic interventions for CRC (n=80) (FIG. 8h). However, endothelial CTM count did not associate with clinical parameters such as tumour stage, grade or presence of distant metastasis (FIG. 8b, Supplementary Tables 6 and 7) or with other variables, including inflammatory markers (FIG. 18). In particular, endothelial CTM numbers in time series analysis indicated that surgical resection events has the strongest effect on CTM distribution, confirming the results in FIG. 7c and further supporting the association of endothelial CTM with the presence of a primary tumour (FIG. 8c). The presence of endothelial CTM in 86.5% of treatment-naive patients (45/52), but only of 2.2% of healthy controls (1/45) indicated that CTM count might be useful in assisting CRC diagnosis. Area under the curve (AUC) of the receiving operator characteristic (ROC) curve comparing treatment-naive patients and healthy controls was 0.930 (FIG. 8d). Remarkably, CRC patients with low pathologic tumour stage (stage≤IIA) were also positive for endothelial CTM in 86.4% (19/22) of cases, with AUC=0.922 (FIG. 8e). Taken together, these results further confirmed the association between endothelial CTM counts and presence of a primary tumour. Moreover, widespread presence of endothelial CTM in treatment-naive patients but not in healthy individuals indicated the potential use of endothelial CTM count as a diagnostic adjunct for CRC.

In conclusion, the isolation, retrieval and analysis of single circulating tumour microemboli (CTM) from colorectal cancer patients is reported here. It is presented for the first time transcriptome profiling of single-CTM and, in contrast to current consensus, several lines of evidence for the tumour endothelial origin of CTM are provided. Endothelial CTM were detected as structures of multiple cells. As such, CTM might be shed from the chaotic tumour vasculature undergoing pathological angiogenesis, a recognized early event in CRC tumour progression. Preclinical models might reveal the mechanisms underlying tumor endothelial cell shedding in circulation, and are currently under investigation. In contrast to CTCs, which are often detected in patients with advanced diseases, CTM were tumor-derived entities prevalent in early stage and preoperative CRC patients. Endothelial CTM counts represent therefore an intriguing modus for early CRC detection. In this study, the presence of CTC clusters was not detected as reported in Aceto et al. This might be the result of differences in patient profiles. In fact, Aceto et al. analyzed blood samples from terminal breast cancer patients, whereas blood samples in this study were mostly derived from preoperative CRC patients. Further studies would need to address specificities of circulating endothelial cell clusters in various diseases. Interestingly, tissue-specific molecular signatures have been demonstrated in endothelial cells from various organs, indicating that CTM might be traced back to their organ of origin based on the expression of specific gene sets. Because of their cellular morphology reminiscent of malignancy, keratins expression and the mixed epithelial and mesenchymal marker profiles, endothelial CTM should not be confused with bona fide malignant CTCs undergoing EMT. At the same time, endothelial CTM analysis might contribute to early colorectal cancer detection and provide direct information on the underlying tumour vasculature during treatment and disease course.

SUPPLEMENTARY TABLE 1

Selected publications including circulating tumor cell clusters or CTM described as cancerous entities (1959-2014)

| # | Year | Article reporting CTM or CTC clusters as cancerous entity | Experimental evidence used to define malignancy |
|---|---|---|---|
| 1 | 1959 | Engell, H.[54] | Cytomorphology |
| 2 | 1960 | Finkel, G. C., & Teshkoff, G. H.[1] | Cytomorphology |
| 3 | 1964 | Seal, S. H.[5] | Cytomorphology |
| 4 | 1964 | Sellwood, R. A. et al.[55] | Cytomorphology |
| 5 | 1965 | Cole, W. H. et al.[56] | Cytomorphology |
| 6 | 1971 | Song, J., et al.[57] | Cytomorphology |
| 7 | 1973 | Griffiths, J. D. et al.[58] | Cytomorphology |
| 8 | 1975 | Salsbury, A. J.[2] | Cytomorphology |
| 9 | 1979 | Ejeckam, G. C. et al.[59] | Cytomorphology/Myeloperoxidase staining |
| 10 | 1988 | Glaves. D. et al.[60] | Cytomorphology/CK staining |
| 11 | 1992 | Aboulafia, D. M.[61] | Cytomorphology/CK staining |
| 12 | 2000 | Vona, G. et al.[3] | Cytomorphology/AFP staining |
| 13 | 2001 | Molnar, B. et al.[62] | Keratin magnetic labeling |
| 14 | 2004 | Vona, G. et al.[63] | Cytomorphology/AFP staining |
| 15 | 2004 | Allard, W. J. et al.[64] | Cytomorphology/CD45-keratin staining |
| 16 | 2007 | Patertini-Brechot, P. & Benall, N. L.[6] | Cytomorphology |
| 17 | 2010 | Stott, S. L. et al.[65] | PSMA/CD45, CK7,8/CD45 stainings |
| 18 | 2010 | Hou, J. M. et al.[66] | Cytomorphology/CD45-NSE stainings |
| 19 | 2011 | Hou, J. M. et al.[67] | CD45/various epithelial and mesenchymal markers immunostainings |
| 20 | 2011 | Khoja, L. et al.[68] | Cytomorphology/CD45-CK stainings |
| 21 | 2011 | Desitter, I. et al.[69] | Cytomorphology/CD45-CK stainings |
| 22 | 2011 | Hofman, V. J. et al.[70] | Cytomorphology |
| 23 | 2011 | Hofman, V. et al.[71] | Cytomorphology |
| 24 | 2012 | Hou, J. M. et al.[72] | EPCAM/CD45/CK/Ki67/Mcl-1 stainings |
| 25 | 2012 | Kling, J. | CD45-CK stainings |
| 26 | 2012 | Cho, E. H. et al.[73] | CD45-CK stainings |
| 27 | 2012 | Krebs, M. G. et al.[74] | Cytomorphology/CD45 |
| 28 | 2012 | Marnnucci, D. et al.[75] | CD45-CK stainings |
| 29 | 2013 | Yu, M. et al.[4] | Epithelial and mesenchymal transcript and protein markers, high-throughput RNA sequencing |
| 30 | 2014 | Aceto, N et al.[20] | Various stainings including PSMA. EPCAM, CK Single cell high-throughout sequencing |

SUPPLEMENTARY TABLE 2

Targeted high-throughput sequencing of single CTM do not mirror matching primary tumor mutations

| Gene | Position | Type | Zygosity | Genotype | ExonicFunc.refGene | Patient 13 P13-Turner |
|---|---|---|---|---|---|---|
| KRAS | KRAS: chr12: 25398284 | SNP | Het | C/T | nonsynonymous SNV | N/A |
| PIK3CA | PIK3CA:chr3: 178936095 | SNP | Het | A/G | nonsynonymous SNV | N/A |
| TP53 | TP53: chr17: 7574003 | SNP | Het | G/A | stopgain SNV | N/A |
| TP53 | TP53: chr17: 7577120 | SNP | Het | C/T | nonsynonymous SNV | N/A |
| TP53 | TP53: chr17: 7578202 | DEL | Het | ACACTATGTCG/A | | N/A |
| TP53 | TP53: chr17: 7578407 | SNP | Het | G/C | nonsynonymous SNV | 32.33082707 |
| TP53 | TP53: chr17: 7578463 | INS | Het | C/CG | frameshift insertion | N/A |
| TP53 | TP53: chr17: 7578645 | SNP | Het | C/T | | N/A |

Treshold: 10%

| Gene | P13-CTM2 | P13-CTM3 | P13-CTM4 | P13-CTM5 | P10-Tumor | Patient 10 P10-CTM1 | P10-CTM4 | P10-CTM5 |
|---|---|---|---|---|---|---|---|---|
| KRAS | NA | NA | NA | NA | NA | NA | NA | NA |
| PIK3CA | NA | NA | NA | NA | NA | NA | NA | NA |
| TP53 | NA | NA | NA | NA | NA | NA | NA | NA |
| TP53 | NA | NA | NA | NA | 49.17458729 | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | 98.61111111 | NA | NA | NA |

Threshold: 10%

| Gene | P10-CTM10 | P10-CTM12 | Patient 14 P14-Tumor | P14-CTM1 | P14-CMT2 | Patient 15 P15-Tumor | P15-CTM5 |
|---|---|---|---|---|---|---|---|
| KRAS | NA | NA | 68.43291995 | NA | NA | NA | NA |
| PIK3CA | NA | NA | NA | NA | NA | 59.6774193b | NA |
| TP53 | NA | NA | NA | NA | NA | 76.29072682 | NA |

SUPPLEMENTARY TABLE 2-continued

Targeted high-throughput sequencing of single CTM do not mirror matching primary tumor mutations

| | | | | | | |
|---|---|---|---|---|---|---|
| TP53 | NA | NA | NA | NA | NA | NA | NA |
| TP53 | NA | NA | NA | NA | NA | NA | NA |
| TP53 | NA | NA | NA | NA | NA | NA | NA |
| TP53 | NA | NA | 47.32098147 | NA | NA | NA | NA |
| TP53 | NA | NA | NA | NA | NA | NA | NA |

Threshold: 10%

| | Patient 7 | | | | Patient 8 | |
|---|---|---|---|---|---|---|
| Gene | P7-Tumor | P7-CMT6 | P7-CTM8 | P7-CTM9 | P8-Tumor | P8-CMT12 |
| KRAS | NA | NA | NA | | NA | NA | NA |
| PIK3CA | NA | NA | NA | | NA | NA | NA |
| TP53 | NA | NA | NA | | NA | NA | NA |
| TP53 | NA | NA | NA | | NA | NA | NA |
| TP53 | NA | NA | NA | | NA | 81.56565657 | NA |
| TP53 | NA | NA | NA | | NA | NA | NA |
| TP53 | NA | NA | NA | | NA | NA | NA |
| TP53 | NA | NA | NA | | NA | NA | NA |

Threshold: 10%

SUPPLEMENTARY TABLE 3

Sparse CTM mutations are not detected in matching primary tumor tissues

| | | | | | | Patient 13 | |
|---|---|---|---|---|---|---|---|
| Gene | Position | Type | Zygosity | Genotype | ExonicFunc.refGene | P13-Tumor | P13-CTM2 |
| AKT1 | AKT1:chr14:105258943 | SNP | Het | T/C | nonsynonymous SNV | NA | NA |
| AKT1 | AKT1:chr14:105258954 | SNP | Het | C/T | synonymous SNV | NA | NA |
| AKT1 | AKT1:chr14:105258963 | SNP | Het | A/G | synonymous SNV | NA | NA |
| AKT1 | AKT1:chr14:105259001 | SNP | Het | C/T | NA | NA | NA |
| AKT1 | AKT1:chr14:105259015 | SNP | Het | T/C | NA | NA | NA |
| BRAF | BRAF:chr7:140453027 | SNP | Het | T/C | NA | NA | NA |
| BRAF | BRAF:chr7:140453110 | SNP | Het | G/A | stopgain SNV | NA | NA |
| BRAF | BRAF:chr7:140453135 | SNP | Hom | A/A | synonymous SNV | NA | NA |
| BRAF | BRAF:chr7:140453160 | DEL | Het | AT/A | | NA | NA |
| BRAF | BRAF:chr7:140453221 | SNP | Het | G/T | NA | NA | NA |
| CTNNB1 | CTNNB1:chr3:41265533 | SNP | Het | A/C | NA | NA | NA |
| EGFR | EGFR:chr7:55240848 | SNP | Hom | G/G | NA | NA | NA |
| EGFR | EGFR:chr7:55241616 | DEL | Hom | T/T | | NA | NA |
| EGFR | EGFR:chr7:55241661 | SNP | Het | C/T | synonymous SNV | NA | NA |
| EGFR | EGFR:chr7:55241727 | SNP | Het | G/A | synonymous SNV | NA | NA |
| EGFR | EGFR:chr7:55241730 | SNP | Hom | T/T | synonymous SNV | NA | NA |
| EGFR | EGFR:chr7:55249014 | SNP | Het | A/G | nonsynonymous SNV | NA | NA |
| EGFR | EGFR:chr7:55249133 | SNP | Het | T/C | nonsynonymous SNV | NA | NA |
| EGFR | EGFR:chr7:55260481 | SNP | Het | T/C | nonsynonymous SNV | NA | NA |
| EGFR | EGFR:chr7:55260492 | SNP | Het | T/C | synonymous SNV | NA | NA |
| KRAS | KRAS:chr12:25378745 | SNP | Het | A/G | NA | NA | 12 |
| KRAS | KRAS:chr12:25380190 | SNP | Het | A/G | nonsynonymous SNV | NA | NA |
| KRAS | KRAS:chr12:25380261 | SNP | Het | G/C | nonsynonymous SNV | NA | NA |
| KRAS | KRAS:chr12:25380262 | SNP | Het | C/T | nonsynonymous SNV | NA | NA |
| KRAS | KRAS:chr12:25380285 | SNP | Het | GT | nonsynonymous SNV | NA | NA |
| KRAS | KRAS:chr12:25380307 | SNP | Het | A/C | nonsynonymous SNV | NA | NA |
| KRAS | KRAS:chr12:25380309 | DEL | Het | GT/G | | NA | NA |
| KRAS | KRAS:chr12:25398236 | SNP | Het | A/G | nonsynonymous SNV | NA | NA |
| NRAS | NRAS:chr1:115256498 | SNP | Hom | T/T | stopgain SNV | NA | NA |
| NRAS | NRAS:chr1:115258685 | SNP | Het | C/T | nonsynonymous SNV | NA | NA |
| PIK3CA | PIK3CA:chr3:178916625 | SNP | Het | A/G | synonymous SNV | NA | NA |
| PIK3CA | PIK3CA:chr3:178916635 | SNP | Het | G/A | nonsynonymous SNV | NA | NA |
| PIK3CA | PIK3CA:chr3:178916638 | DEL | Het | | TGGGGCATCCACTT/G | NA | NA |
| PTEN | PTEN:chr10:89685300 | DEL | Hom | C/C | | NA | NA |
| PTEN | PTEN:chr10:89690872 | SNP | Het | T/C | NA | NA | NA |
| PTEN | PTEN:chr10:89690906 | SNP | Het | T/C | NA | NA | NA |
| PTEN | PTEN:chr10:89692825 | DEL | Het | CT/C | | NA | NA |
| PTEN | PTEN:chr10:89692891 | SNP | Het | A/G | synonymous SNV | NA | NA |
| PTEN | PTEN:chr10:89692916 | SNP | Het | A/T | nonsynonymous SNV | NA | NA |
| PTEN | PTEN:chr10:89711843 | SNP | Het | A/G | NA | NA | NA |
| PTEN | PTEN:chr10:89711866 | SNP | Het | G/A | NA | NA | NA |
| PTEN | PTEN:chr10:89711910 | SNP | Het | T/C | synonymous SNV | NA | NA |
| PTEN | PTEN:chr10:89711998 | SNP | Het | T/C | nonsynonymous SNV | NA | NA |
| PTEN | PTEN:chr10:89720698 | SNP | Het | A/G | synonymous SNV | NA | NA |
| PTEN | PTFN:chr10:89720707 | SNP | Het | C/T | synonymous SNV | NA | NA |
| PTEN | PTEN:chr10:89720709 | SNP | Het | C/T | nonsynonymous SNV | NA | NA |

SUPPLEMENTARY TABLE 3-continued

Sparse CTM mutations are not detected in matching primary tumor tissues

| TP53 | TP53:chr17:7572967 | SNP | Het | T/C | nonsynonymous SNV | NA | NA |
| TP53 | TP53:chr17:7573857 | SNP | Het | A/G | NA | NA | NA |
| TP53 | TP53:chr17:7576637 | SNP | Het | T/A | nonsynonymous SNV | NA | NA |
| TP53 | TP53:chr17:7577102 | SNP | Het | C/T | nonsynonymous SNV | NA | NA |
| TP53 | TP53:chr17:7577127 | DEL | Het | CAA/C | | NA | NA |
| TP53 | TP53:chr17:7577396 | SNP | Het | T/C | NA | NA | NA |
| TP53 | TP53:chr17:7577444 | SNP | Het | A/G | NA | NA | NA |
| TP53 | TP53:chr17:7577450 | SNP | Het | A/G | NA | NA | NA |
| TP53 | TP53:chr17:7577559 | SNP | Hom | A/A | nonsynonymous SNV | NA | NA |
| TP53 | TP53:chr17:7578155 | SNP | Het | A/G | NA | NA | NA |
| TP53 | TP53:chr17:7578237 | SNP | Hom | T/T | synonymous SNV | NA | NA |
| TP53 | TP53:chr17:7578297 | SNP | Het | C/T | NA | NA | NA |
| TP53 | TP53:chr17:7578369 | DEL | Hom | A/A | | NA | NA |
| TP53 | TP53:chr17:7578385 | SNP | Hom | T/T | nonsynonymous SNV | NA | NA |
| TP53 | TP53:chr17:7578389 | DEL | Hom | G/G | | NA | NA |
| TP53 | TP53:chr17:7578399 | SNP | Het | G/A | synonymous SNV | NA | NA |
| TP53 | TP53:chr17:7578400 | SNP | Het | G/A | nonsynonymous SNV | NA | NA |
| TP53 | TP53:chr17:7578502 | SNP | Het | A/G | nonsynonymous SNV | NA | NA |
| TP53 | TP53:chr17:7578645 | SNP | Hom | T/T | | NA | NA |
| TP53 | TP53:chr17:7579393 | SNP | Het | A/G | synonymous SNV | NA | NA |
| TP53 | TP53:chr17:7579432 | SNP | Het | A/G | | NA | 14.814815 |
| TP53 | TP53:chr17:7579432 | DEL | Het | AG/AGG | | NA | NA |

Treshold: 10%

| | | | | Patient 10 | | | |
|---|---|---|---|---|---|---|---|
| Gene | P13-CTM3 | P13-CTM4 | P13-CTM5 | P10-Tumor | P10-CTM1 | P10-CTM4 | P10-CTM5 | P10-CTM10 |
| AKT1 | NA | NA | NA | NA | 26.869159 | NA | NA | NA |
| AKT1 | NA | NA | NA | NA | NA | NA | 12.262357 | NA |
| AKT1 | NA | NA | NA | NA | 15.242494 | NA | NA | NA |
| AKT1 | NA | NA | NA | NA | NA | NA | 11.568123 | NA |
| AKT1 | NA | NA | NA | NA | NA | 39.308963 | NA | NA |
| BRAF | NA | NA | NA | NA | NA | NA | NA | NA |
| BRAF | NA | NA | NA | NA | NA | NA | NA | NA |
| BRAF | NA | NA | NA | NA | NA | NA | NA | NA |
| BRAF | NA | NA | NA | NA | NA | NA | NA | NA |
| BRAF | NA | NA | NA | NA | NA | NA | NA | NA |
| CTNNB1 | NA | NA | NA | NA | NA | NA | NA | NA |
| EGFR | NA | NA | 100 | NA | NA | NA | NA | NA |
| EGFR | NA | NA | 100 | NA | NA | NA | NA | NA |
| EGFR | NA | NA | NA | NA | NA | NA | NA | NA |
| EGFR | NA | NA | NA | NA | NA | NA | NA | NA |
| EGFR | NA | NA | 100 | NA | NA | NA | NA | NA |
| EGFR | NA | NA | NA | NA | NA | NA | NA | NA |
| EGFR | NA | NA | NA | NA | NA | NA | NA | 13.173653 |
| EGFR | NA | 25.728643 | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | 58.930373 | NA | NA | NA | NA | NA |
| KRAS | NA | NA | NA | NA | NA | NA | NA | NA |
| NRAS | NA | NA | NA | NA | NA | NA | NA | NA |
| NRAS | NA | NA | 20.731097 | NA | NA | NA | NA | NA |
| PIK3CA | NA | NA | NA | NA | NA | NA | NA | NA |
| PIK3CA | NA | NA | NA | NA | NA | NA | NA | NA |
| PIK3CA | NA | NA | NA | NA | NA | NA | NA | NA |
| PTEN | NA | NA | NA | NA | NA | NA | NA | 100 |
| PTEN | NA | NA | 10.619469 | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | 13.293944 |
| PTEN | NA | NA | NA | NA | NA | NA | NA | 13.543307 |
| PTEN | NA | NA | NA | NA | NA | NA | NA | NA |
| PTEN | NA | NA | 14.035088 | NA | NA | NA | NA | NA |
| PTEN | NA | NA | NA | NA | NA | NA | NA | NA |
| TP53 | NA | NA | NA | NA | NA | NA | NA | 34.554974 |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |

SUPPLEMENTARY TABLE 3-continued

Sparse CTM mutations are not detected in matching primary tumor tissues

| TP53 | NA | NA | NA | NA | NA | NA | NA | NA |
|---|---|---|---|---|---|---|---|---|
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | 38.157895 |
| TP53 | NA | NA | NA | NA | NA | NA | NA | NA |
| TP53 | NA | NA | NA | NA | NA | NA | NA | 59.375 |

Threshold. 10%

| | | Patient 14 | | | Patient 15 | | Patient 7 | |
|---|---|---|---|---|---|---|---|---|
| Gene | P10-CTM12 | P14-Tumor | P14-CTM1 | P14-CTM2 | P15-Tumor | P15-CTM5 | P7-Tumor | P7-CTM6 |
| AKT1 | NA | NA | NA | NA | NA | NA | NA | NA |
| AKT1 | NA | NA | NA | NA | NA | NA | NA | NA |
| AKT1 | NA | NA | NA | NA | NA | NA | NA | NA |
| AKT1 | NA | NA | NA | NA | NA | NA | NA | NA |
| AKT1 | NA | NA | NA | NA | NA | NA | NA | NA |
| BRAF | NA | NA | 37.5 | NA | NA | NA | NA | NA |
| BRAF | NA | NA | NA | 64.839468 | NA | NA | NA | NA |
| BRAF | NA | NA | NA | 100 | NA | NA | NA | NA |
| BRAF | NA | NA | 30.30303 | NA | NA | NA | NA | NA |
| BRAF | NA | NA | 56.149733 | NA | NA | NA | NA | NA |
| CTNNB1 | NA | NA | 23.333333 | NA | NA | NA | NA | NA |
| EGFR | NA | NA | NA | NA | NA | NA | NA | NA |
| EGFR | NA | NA | NA | NA | NA | NA | NA | NA |
| EGFR | NA | NA | NA | NA | NA | NA | NA | NA |
| EGFR | NA | NA | 50 | NA | NA | NA | NA | NA |
| EGFR | NA | NA | NA | NA | NA | NA | NA | NA |
| EGFR | 17.751479 | NA | NA | NA | NA | NA | NA | NA |
| EGFR | NA | NA | NA | NA | NA | NA | NA | NA |
| EGFR | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | 33.766234 | NA | NA | NA | NA | NA |
| KRAS | NA | NA | 11.538462 | NA | NA | NA | NA | NA |
| KRAS | NA | NA | NA | NA | NA | NA | NA | NA |
| KRAS | NA | NA | NA | 42.857143 | NA | NA | NA | NA |
| NRAS | NA | NA | NA | NA | NA | NA | NA | NA |
| NRAS | NA | NA | NA | NA | NA | NA | NA | NA |
| PIK3CA | NA | NA | 22.413793 | NA | NA | NA | NA | NA |
| PIK3CA | NA | NA | NA | NA | NA | NA | NA | NA |
| PIK3CA | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | 18.233296 | NA | NA |
| PTEN | NA | NA | NA | NA | NA | NA | NA | NA |
| PTEN | NA | NA | 10.344828 | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | 72.727273 | NA | NA | NA | NA | NA |
| PTEN | NA | NA | NA | NA | NA | NA | NA | NA |
| PTEN | NA | NA | 47.727273 | NA | NA | NA | NA | NA |
| TP53 | NA | NA | NA | NA | NA | NA | NA | NA |
| TP53 | NA | NA | 13.571429 | NA | NA | NA | NA | NA |
| TP53 | NA | NA | NA | NA | NA | NA | NA | NA |
| TP53 | NA | NA | 19.088319 | NA | NA | NA | NA | NA |
| TP53 | 10.515774 | NA | NA | NA | NA | NA | NA | NA |
| TP53 | NA | NA | NA | NA | NA | NA | NA | NA |
| TP53 | NA | NA | NA | NA | NA | NA | NA | NA |

SUPPLEMENTARY TABLE 3-continued

Sparse CTM mutations are not detected in matching primary tumor tissues

| Gene | | | | | | | | |
|------|---|---|---|---|---|---|---|---|
| TP53 | NA | NA | NA | NA | NA | 100 | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | 100 |
| TP53 | NA | NA | NA | NA | NA | NA | NA | 100 |
| TP53 | NA | NA | NA | NA | NA | NA | NA | 100 |
| TP53 | NA | NA | NA | NA | NA | NA | NA | 97.345133 |
| TP53 | NA | NA | 11.188811 | NA | NA | NA | NA | NA |
| TP53 | NA | NA | 17.241379 | NA | NA | NA | NA | NA |
| TP53 | NA | NA | NA | NA | NA | NA | NA | 100 |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |

Threshold. 10%

| Gene | P7-CTMB | P7-CTM9 | Patient 8 P8-Tumor | P8-CTM12 |
|------|---------|---------|---------|----------|
| AKT1 | NA | NA | NA | NA |
| AKT1 | NA | NA | NA | NA |
| AKT1 | NA | NA | NA | NA |
| AKT1 | NA | NA | NA | NA |
| AKT1 | NA | NA | NA | NA |
| BRAF | NA | NA | NA | NA |
| BRAF | NA | NA | NA | NA |
| BRAF | NA | NA | NA | NA |
| BRAF | NA | NA | NA | NA |
| BRAF | NA | NA | NA | NA |
| CTNNB1 | NA | NA | NA | NA |
| EGFR | NA | NA | NA | NA |
| EGFR | NA | NA | NA | NA |
| EGFR | 35 | NA | NA | NA |
| EGFR | NA | NA | NA | NA |
| EGFR | NA | NA | NA | NA |
| EGFR | 23.880597 | NA | NA | NA |
| EGFR | NA | NA | NA | NA |
| EGFR | NA | NA | NA | NA |
| KRAS | NA | NA | NA | NA |
| KRAS | NA | NA | NA | 19.626168 |
| KRAS | NA | NA | NA | NA |
| KRAS | NA | NA | NA | 16.8 |
| KRAS | NA | NA | NA | NA |
| KRAS | NA | NA | NA | NA |
| KRAS | NA | NA | NA | NA |
| NRAS | NA | 98.372966 | NA | NA |
| NRAS | NA | NA | NA | NA |
| PIK3CA | NA | NA | NA | NA |
| PIK3CA | NA | NA | NA | 91.941392 |
| PIK3CA | NA | NA | NA | 88.489209 |
| PTEN | NA | NA | NA | NA |
| PTEN | NA | NA | NA | NA |
| PTEN | NA | NA | NA | NA |
| PTEN | 40 | NA | NA | NA |
| PTEN | NA | NA | NA | NA |
| PTEN | 18.518519 | NA | NA | NA |
| PTEN | 19.485294 | NA | NA | NA |
| PTEN | NA | NA | NA | NA |
| PTEN | NA | NA | NA | NA |
| PTEN | 11.666667 | NA | NA | NA |
| PTEN | NA | NA | NA | NA |
| PTEN | NA | NA | NA | NA |
| TP53 | NA | NA | NA | NA |
| TP53 | NA | NA | NA | NA |
| TP53 | NA | NA | NA | NA |
| TP53 | 10.714286 | NA | NA | NA |
| TP53 | NA | NA | NA | NA |
| TP53 | NA | NA | NA | NA |
| TP53 | NA | 13.157895 | NA | NA |
| TP53 | NA | 18.421053 | NA | NA |
| TP53 | NA | NA | NA | NA |
| TP53 | NA | NA | NA | 14.220183 |
| TP53 | NA | NA | NA | 98.536585 |
| TP53 | NA | NA | NA | 93 |

SUPPLEMENTARY TABLE 3-continued

Sparse CTM mutations are not detected in matching primary tumor tissues

| | | | | |
|---|---|---|---|---|
| TP53 | NA | NA | NA | NA |
| TP53 | NA | NA | NA | NA |
| TP53 | NA | NA | NA | NA |
| TP53 | NA | NA | NA | NA |
| TP53 | NA | NA | NA | NA |
| TP53 | NA | NA | NA | NA |
| TP53 | NA | NA | NA | 100 |
| TP53 | NA | NA | NA | NA |
| TP53 | NA | NA | NA | NA |
| TP53 | NA | NA | NA | NA |

Threshold 10%

SUPPLEMENTARY TABLE 4

RNA-seq data, uniquely mapped reads to hg19 exons

| ID | #Unique reads mapped to hg19 exons |
|---|---|
| P10-T | 9,824,250 |
| P19-Met | 9,200,220 |
| P1-N | 12,046,807 |
| P1-TUc | 11,627,650 |
| P1-TUd | 10,474,561 |
| P1-TUs | 12,120,551 |
| P18-N | 11,691,022 |
| P18-T | 10,077,598 |
| P10-N | 11,940,709 |
| P21-N | 12,115,725 |
| P21-T | 10,030,315 |
| P20-N | 9,710,218 |
| P20-T | 7,196,431 |
| P8-N | 9,574,544 |
| P8-T | 9,413,088 |
| P19-N | 9,868,631 |
| P19-T | 9,156,651 |
| P8-CTM10 | 7,055,733 |
| P8-CTM11 | 6,873,889 |
| P16-CTM2 | 772,636 |
| P21-CTM11 | 6,526,429 |
| P19-CTM2 | 741,682 |
| P1-CTM1 | 3,368,445 |
| P1-CTM3 | 4,825,103 |
| P1-CTM4 | 5,493,502 |
| P10-CTM10 | 2,916,536 |
| P18-CTM4 | 357,115 |
| P18-CTM6 | 3,113,219 |
| P20-CTM16 | 1,001,059 |
| P20-CTM14 | 896,617 |
| P1-CTM8 | 620,380 |
| P18-CTM5 | 1,363,670 |
| P8-CTM7 | 3,763,227 |
| P20-CTM15 | 1,424,262 |
| P18-CTM2 | 1,007,933 |

Legend:
P, patient
T, tumor tissue
c, center
d, deep
s, superficial
N, normal tissue
Met, metastasis
CTM, circulating tumor microembolus

SUPPLEMENTARY TABLE 5

Pre- and post surgery CTM count. Data from FIG. 4e

| Patient | CTM count Pre | CTM count Post |
|---|---|---|
| P05 | 9 | 6 |
| P19 | 2 | 0 |
| P22 | 124 | 0 |
| P54 | 0 | 3 |
| P64 | 4 | 0 |
| P66 | 46 | 0 |
| P67 | 1 | 0 |
| P69 | 0 | 0 |
| P71 | 79 | 2 |
| P72 | 24 | 0 |
| P73 | 48 | 0 |
| P74 | 13 | 2 |
| P75 | 3 | 0 |
| P77 | 1 | 0 |
| P78 | 1 | 0 |
| P80 | 0 | 0 |
| P82 | 36 | 0 |

Pre: CTM count in blood 0-24 hrs before surgery
Post: CTM count in blood 24-72 hrs after surgery

SUPPLEMENTARY TABLE 6

Baseline patients and healthy donors characteristics

| Characteristic | Patients | Controls |
|---|---|---|
| Total, n | 80 | 45 |
| Age, yr, median (range) | 60 (26-80) | 45 (26-81) |
| Gender, n (%) | | |
| Male | 48 (60) | 19 (43) |
| Female | 32 (40) | 25 (57) |
| Ethnicity, n (%) | | |
| Chinese | 56 (70) | |
| Other | 24 (30) | |
| Tumor Location n (%) | | |
| Recto-sigmoid | 67 (77) | |
| Other | 18 (23) | |
| Stage, n (%) | | |
| ≤ IIA | 26 (35) | |
| IIB-IIIC | 26 (35) | |
| IV | 22 (30) | |
| Grade, n (%) | | |
| 1-2 | 58 (89) | |
| 3-4 | 7 (11) | |
| Metastatic CRC, n (%) | | |
| M0 (no distant metastasis) | 54 (72) | |
| M1 (distant metastasis) | 21 (28) | |

SUPPLEMENTARY TABLE 6-continued

Baseline patients and healthy donors characteristics

| Characteristic | Patients | Controls |
|---|---|---|
| Treatment, n (%) | | |
| Untreated | 52 (65) | |
| Neoadjuvant | 11 (14) | |
| Surgery* | 5 (6) | |
| Adjuvant | 4 (5) | |
| Palliative | 8 (10) | |

Figure 3:
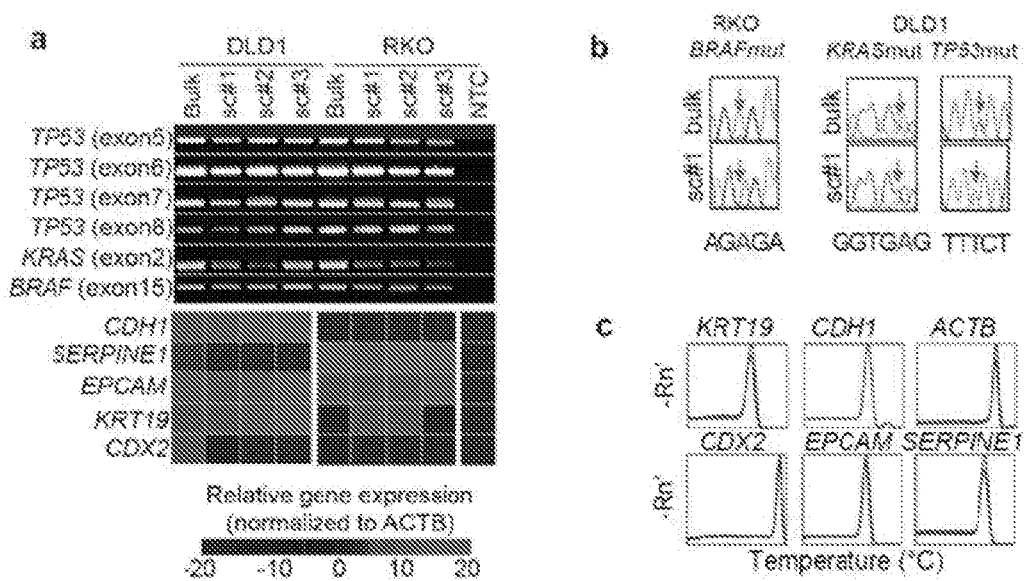
FIG. 3 provides the proof of principle for the scrmPCR method of the disclosure. Single DLD1 and RKO cells (colorectal cancer cell lines) were micro-manipulated in 5 µl 2× Reaction Buffer (CellDirect kit). scrmPCR was then performed as described herein, with the results shown in (a). Genomic regions belonging to TP53, KRAS and BRAF genes were amplified. PCR products were subjected to Sanger sequencing and known hotspot mutations that have been previously characterized in both cell lines were detected as shown in (b). At the same time several transcripts from the same cells were amplified and shown to have variable gene expression in both cell lines. Gene expression specificity was verified by the melting curve peak temperature and by the presence of a single peak, as shown in (c).

*post op. data from FIG. 3e not included

SUPPLEMENTARY TABLE 7

CTM count for each baseline sample type and number of single CTM analyzed in this study

| Patient ID | Abbreviation | Source | Baseline sample type | CTM count* |
|---|---|---|---|---|
| Donor 1 | D01 | NUH | Healthy | 0 |
| Donor 2 | D02 | NUH | Healthy | 0 |
| Donor 3 | D03 | NUH | Healthy | 0 |
| Donor 4 | D04 | NUH | Healthy | 0 |
| Donor 5 | D05 | NUH | Healthy | 0 |
| Donor 6 | D06 | NUH | Healthy | 0 |
| Donor 7 | D07 | NUH | Healthy | 0 |
| Donor 8 | D08 | NUH | Healthy | 0 |
| Donor 9 | D09 | NUH | Healthy | 0 |
| Donor 10 | D10 | NUH | Healthy | 0 |
| Donor 11 | D11 | NUH | Healthy | 0 |
| Donor 12 | D12 | NUH | Healthy | 0 |
| Donor 13 | D13 | IBN | Healthy | 0 |
| Donor 14 | D14 | NUH | Healthy | 0 |
| Donor 15 | D15 | NUH | Healthy | 0 |
| Donor 16 | D16 | NUH | Healthy | 0 |
| Donor 17 | D17 | NUH | Healthy | 0 |
| Donor 15 | D18 | NUH | Healthy | 0 |
| Donor 19 | D19 | NUH | Healthy | 0 |
| Donor 20 | D20 | NUH | Healthy | 0 |
| Donor 21 | D21 | NUH | Healthy | 0 |
| Donor 22 | D22 | NUH | Healthy | 0 |
| Donor 23 | D23 | NUH | Healthy | 0 |
| Donor 24 | D24 | NUH | Healthy | 0 |
| Donor 25 | D25 | NUH | Healthy | 0 |
| Donor 26 | D26 | NUH | Healthy | 0 |
| Donor 27 | D27 | NUH | Healthy | 0 |
| Donor 28 | D28 | NUH | Healthy | 0 |
| Donor 29 | D29 | IBN | Healthy | 0 |
| Donor 30 | D30 | IBN | Healthy | 0 |
| Donor 31 | D31 | IBN | Healthy | 0 |
| Donor 32 | D32 | IBN | Healthy | 0 |
| Donor 33 | D33 | NUH | Healthy | 0 |
| Donor 34 | D34 | NUH | Healthy | 0 |
| Donor 35 | D35 | NUH | Healthy | 0 |
| Donor 36 | D36 | NUH | Healthy | 0 |
| Donor 37 | D37 | NUH | Healthy | 0 |
| Donor 38 | D38 | NUH | Healthy | 0 |
| Donor 39 | D39 | NUH | Healthy | 0 |
| Donor 40 | D40 | NUH | Healthy | 0 |
| Donor 41 | D41 | NUH | Healthy | 0 |
| Donor 42 | D42 | NUH | Healthy | 0 |
| Donor 43 | D43 | NUH | Healthy | 0 |
| Donor 44 | D44 | NUH | Healthy | 9 |
| Donor 45 | D45 | NUH | Healthy | 0 |
| Patient 01 | P01 | NCC | CRC - Treatment Naive | 49 |
| Patient 02 | P02 | NCC | CRC - Treatment Naive | 3 |
| Patient 03 | P03 | FSH | CRC - Treatment Naive | 7 |
| Patient 04 | P04 | NCC | CRC - Palliative | 17 |
| Patient 05 | P05 | NCC | CRC - Treatment Naive | 9 |
| Patient 06 | P06 | FSH | CRC - Post Neoadjuvant | 0 |
| Patient 07 | P07 | FSH | CRC - Treatment Naive - Early stage | 26 |
| Patient 08 | P08 | FSH | CRC - Treatment Naive - Early stage | 76 |
| Patient 09 | P09 | FSH | CRC - Treatment Naive - Early stage | 52 |
| Patient 10 | P10 | FSH | CRC - Treatment Naive | 26 |
| Patient 11 | P11 | NCC | CRC - Palliative | 1 |
| Patient 12 | P12 | NCC | CRC - Palliative | 0 |
| Patient 13 | P13 | FSH | CRC - Treatment Naive - Early stage | 32 |
| Patient 14 | P14 | FSH | CRC - Treatment Naive - Early stage | 3 |
| Patient 15 | P15 | FSH | CRC - Treatment Naive - Early stage | 13 |
| Patient 16 | P16 | FSH | CRC - Treatment Naive | 2 |

SUPPLEMENTARY TABLE 7-continued

CTM count for each baseline sample type and number of single CTM analyzed in this study

| Patient ID | Abbreviation | Source | Baseline sample type | CTM count* |
|---|---|---|---|---|
| Patient 17 | P17 | FSH | CRC - Treatment Naive | 0 |
| Patient 18 | P18 | FSH | CRC - Treatment Naive - Early stage | 9 |
| Patient 19 | P19 | NCC | CRC - Treatment Naive | 2 |
| Patient 20 | P20 | FSH | CRC - Treatment Naive | 80 |
| Patient 21 | P21 | FSH | CRC - Treatment Naive | 16 |
| Patient 22 | P22 | FSH | CRC - Post Neoadjuvant | 124 |
| Patient 23 | P23 | FSH | CRC - Treatment Naive - Early stage | 12 |
| Patient 24 | P24 | FSH | CRC - Treatment Naive - Early stage | 23 |
| Patient 25 | P25 | FSH | CRC - Treatment Naive | 45 |
| Patient 26 | P26 | FSH | CRC - Treatment Naive | 5 |
| Patient 27 | P27 | FSH | CRC - Treatment Naive - Early stage | 34 |
| Patient 28 | P28 | FSH | | NA |
| Patient 29 | P29 | FSH | CRC - Post Neoadjuvant | 15 |
| Patient 30 | P30 | FSH | CRC - Treatment Naive | 3 |
| Patient 31 | P31 | FSH | CRC - Treatment Naive | 0 |
| Patient 32 | P32 | FSH | CRC - Treatment Naive - Early stage | 18 |
| Patient 33 | P33 | FSH | CRC - Post Neoadjuvant | 3 |
| Patient 34 | P34 | FSH | CRC - Treatment Naive - Early stage | 2 |
| Patient 35 | P35 | FSH | CRC - Post Neoadjuvant | 2 |
| Patient 36 | P36 | FSH | CRC - Post Neoadjuvant | 0 |
| Patient 37 | P37 | FSH | CRC - Post Neoadjuvant | 1 |
| Patient 38 | P38 | FSH | | NA |
| Patient 39 | P39 | FSH | CRC - Treatment Naive | 0 |
| Patient 40 | P40 | FSH | CRC - Treatment Naive - Early stage | 1 |
| Patient 41 | P41 | FSH | CRC - Treatment Naive | 2 |
| Patient 42 | P42 | FSH | CRC - Treatment Naive - Early stage | 3 |
| Patient 43 | P43 | FSH | CRC - Treatment Naive | 93 |
| Patient 44 | P44 | FSH | CRC - Treatment Naive | 48 |
| Patient 45 | P45 | FSH | CRC - Treatment Naive | 9 |
| Patient 46 | P46 | FSH | CRC - Treatment Naive | 249 |
| Patient 47 | P47 | FSH | CRC - Treatment Naive - Early stage | 0 |
| Patient 48 | P48 | FSH | CRC - Treatment Naive | 6 |
| Patient 49 | P49 | FSH | CRC - Treatment Naive | 25 |
| Patient 50 | P50 | FSH | CRC - Treatment Naive - Early stage | 0 |
| Patient 51 | P51 | NCC | CRC - Palliative | 24 |
| Patient 52 | P52 | NCC | CRC - Palliative | 0 |
| Patient 53 | P53 | NCC | CRC - Post Surgery | 0 |
| Patient 54 | P54 | NCC | CRC - Post Neoadjuvant | 0 |
| Patient 55 | P55 | NCC | CRC - Post Surgery | 0 |
| Patient 56 | P56 | NCC | CRC - Post Surgery | 0 |
| Patient 57 | P57 | NCC | CRC - Post Adjuvant | 0 |
| Patient 56 | P56 | NCC | CRC - Post Adjuvant | 6 |
| Patient 59 | P59 | NCC | CRC - Palliative | 1 |
| Patient 60 | P60 | NCC | CRC - Palliative | 0 |
| Patient 61 | P61 | NCC | CRC - Post Surgery | 0 |
| Patient 62 | P62 | NCC | CRC - Palliative | 3 |
| Patient 63 | P63 | NCC | CRC - Post Neoadjuvant | 40 |
| Patient 64 | P64 | NCC | CRC - Post Neoadjuvant | 4 |
| Patient 65 | P65 | NCC | CRC - Post Surgery | 0 |
| Patient 66 | P66 | NCC | CRC - Treatment Naive | 46 |
| Patient 67 | P67 | NCC | CRC - Treatment Naive | 1 |
| Patient 68 | P68 | NCC | CRC - Post Adjuvant | 0 |
| Patient 69 | P69 | NCC | CRC - Treatment Naive - Early stage | 0 |
| Patient 70 | P70 | NCC | CRC - Treatment Naive | 7 |
| Patient 71 | P71 | NCC | CRC - Treatment Naive | 79 |
| Patient 72 | P72 | NCC | CRC - Treatment Naive - Early stage | 24 |
| Patient 73 | P73 | NCC | CRC - Treatment Naive | 48 |
| Patient 74 | P74 | NCC | CRC - Treatment Naive - Early stage | 13 |
| Patient 75 | P75 | NCC | CRC - Treatment Naive - Early stage | 3 |
| Patient 76 | P76 | NCC | CRC - Treatment Naive | 12 |
| Patient 77 | P77 | NCC | CRC - Treatment Naive - Early stage | 1 |
| Patient 78 | P78 | NCC | CRC - Treatment Naive | 1 |
| Patient 79 | P79 | NCC | CRC - Treatment Naive, Early stage | 14 |
| Patient 80 | P80 | NCC | CRC - Treatment Naive | 0 |
| Patient 81 | P81 | NCC | CRC - Treatment Naive | 14 |
| Patient 82 | P82 | NCC | CRC - Post Neoadjuvant | 36 |

Legend:
NUH, National University Hospital Singapore
IBN, Institute of Bioengineering and Nanotechnology, Singapore
FSH, Fortis Surgical Hospital, Singapore
NCC, National Cancer Center, Singapore
CRC, Colorectal cancer
Early stage, stage ≤ IIA
*post-OP samples from FIG. 3f not included

REFERENCE

Aboulafia, D. M. Carcinocythemia. A terminal manifestation of metastatic breast cancer. West. J. Med. 157, 672-674 (1992).

Allard, W. J. et al. Tumor cells circulate in the peripheral blood of all major carcinomas but not in healthy subjects or patients with nonmalignant diseases. Clin. Cancer Res. 10, 6897-6904 (2004).

Aceto, N. et al. Circulating tumor cell clusters are oligoclonal precursors of breast cancer metastasis. Cell 158, 1110-1122 (2014).

Bbenek, K., Kunkel, A. T., (1993). "The fidelity of retroviral reverse transcriptases". In Skalka, M. A., Goff, P. S. Reverse transcriptase. New York: Cold Spring Harbor Laboratory Press. p. 85.ISBN 0-87969-382-7.

Borgia, B. et al. A proteomic approach for the identification of vascular markers of liver metastasis. Cancer Res. 70, 309-318 (2010).

Champely, S. pwr: Basic Functions for Power Analysis. (R Foundation for Statistical Computing, Vienna, 2009), Cima, I. et al. Label-free isolation of circulating tumor cells in microfluidic devices: current research and perspectives. Biomicrofluidics 7, 011810 (2013).

Cohen, J. Statistical Power Analysis for the Behavioral Sciences. (L. Erlbaum Associates, 1988).

Cole, W. H., Roberts, S. S., Webb, R. S., Strehl, F. W. & Oates, G. D. Dissemination of cancer with special emphasis on vascular spread and implantation. Ann. Surg. 161, 753-770 (1965).

Colombo, E., Calcaterra, F., Cappelletti, M., Mavilio, D. & Della Bella, S. Comparison of fibronectin and collagen in supporting the isolation and expansion of endothelial progenitor cells from human adult peripheral blood. PLoS One 8, e66734 (2013).

Coumans, F. A. W., van Dalum, G., Beck, M. & Terstappen, L. W. M. M. Filter characteristics influencing circulating tumor cell enrichment from whole blood. *PLoS One* 8, e61770 (2013).

Cho, E. H. et al. Characterization of circulating tumor cell aggregates identified in patients with epithelial tumors. *Phys. Biol.* 9, 016001 (2012).

Desitter, I. et al. A new device for rapid isolation by size and characterization of rare circulating tumor cells. Anticancer Res. 31,427-441 (2011).

Ejeckam, G. C., Sogbein, S. K. & McLeish, W. A. Carcinocythemia due to metastatic oat-cell carcinoma of the lung. Can. Med. Assoc. J. 120,336-338 (1979).

Engell, H. C. Cancer cells in the blood; a five to nine year follow up study. *Ann. Surg.* 149, 457-461 (1959).

El-Heliebi, A. et al. Are morphological criteria sufficient for the identification of circulating tumor cells in renal cancer? J. Transl. Med. 11, 214 (2013).

Finkel, G. C. & Tishkoff, G. H. Malignant cells in a peripheral blood smear: report of a case. N. Engl. J. Med. 262, 187-188 (1960).

Glaves, D., Hubert, R. P. & Weiss, L. Haematogenous dissemination of cells from human renal adenocarcinomas. Br. J. Cancer 57, 32-35 (1988).

Griffiths, J. D., McKinna, J. A., Rowbotham, H. D., Tsolakidis, P. & Salsbury, A. J. Carcinoma of the colon and rectum: circulating malignant cells and five-year survival. Cancer 31, 226-236 (1973).

Gupta, G. P. et al. Mediators of vascular remodelling co-opted for sequential steps in lung metastasis. Nature 446,765-770 (2007).

Herbert, J. M. J., Stekel, D., Sanderson, S., Heath, V. L. & Bicknell, R. A novel method of differential gene expression analysis using multiple eDNA libraries applied to the identification of tumour endothelial genes. BMC Genomics 9,153 (2008).

Hofman, V. J. et al. Cytopathologic detection of circulating tumor cells using the isolation by size of epithelial tumor cell method: promises and pitfalls. Am. J. Clin. Pathol. 135, 146-156 (2011).

Hofman, V. et al. Preoperative circulating tumor cell detection using the isolation by size of epithelial tumor cell method for patients with lung cancer is a new prognostic biomarker. Clin. Cancer Res. 17, 827-835 (2011).

Hou, J.-M. et al. Circulating tumor cells, enumeration and beyond. Cancers (Basel). 2, 1236-1250 (2010).

Hou, J.-M. et al. Circulating tumor cells as a window on metastasis biology in lung cancer. Am. J. Pathol. 178, 989-996 (2011).

Hou, J. M. et al. Clinical significance and molecular characteristics of circulating tumor cells and circulating tumor microemboli in patients with small-cell lung cancer. J. Clin. Oncol. 30, 525-532 (2012).

Kalka, C. et al. Transplantation of ex vivo expanded endothelial progenitor cells for therapeutic neovascularization. Proc. Natl. Acad. Sci. USA 97, 3422-3427 (2000).

Khoja, L. et al. A pilot study to explore circulating tumour cells in pancreatic cancer as a novel biomarker. Br. J. Cancer 106, 508-16 (2012).

Kling, J. Beyond counting tumor cells. *Nat. Biotechnol.* 30, 578-580 (2012).

Krebs, M. G. et al. Analysis of circulating tumor cells in patients with non-small cell lung cancer using epithelial marker-dependent and -independent approaches. J. Thorac. Oncol. 7, 306-315 (2012).

Lim, L. S. et al. Microsieve lab-chip device for rapid enumeration and fluorescence in situ hybridization of circulating tumor cells. *Lab on a Chip* 12, 4388-4396 (2012).

Mabbott, N. A., Baillie, J. K., Brown, H., Freeman, T. C. & Hume, D. A. An expression atlas of human primary cells: inference of gene function from coexpression networks. BMC Genomics 14, 632 (2013).

Marrinucci, D. et al. Fluid biopsy in patients with metastatic prostate, pancreatic and breast cancers. Phys. Biol. 9, 016003 (2012).

Molnar, B., Ladanyi, A., Tanko, L., Sréter, L. & Tulassay, Z. Circulating tumor cell clusters in the peripheral blood of colorectal cancer patients. Clin. Cancer Res. 7, 4080-4085 (2001).

Mura, M. et al. Identification and angiogenic role of the novel tumor endothelial marker CLEC14A. Oncogene 31, 293-305 (2012).

Ni, X. et al. Reproducible copy number variation patterns among single circulating tumor cells of lung cancer patients. Proc. Natl. Acad. Sci. USA 110, 21083-21088 (2013).

Paterlini-Brechot, P. & Benali, N. L. Circulating tumor cells (CTC) detection: clinical impact and future directions. Cancer Lett. 253, 180-204 (2007).

Peixoto, A., Monteiro, M., Rocha., B. & Veiga-Fernandes, H. Quantification of multiple gene expression in individual cells. Genome Res. 14, 1938-1947 (2004).

R Core Team. R: A Language and Environment for Statistical Computing. (R Foundation for Statistical Computing, Vienna, 2005).

Rice, M. E. & Harris, G. T. Comparing effect sizes in follow-up studies: ROC Area, Cohen's d, and r. Law Hum. Behav. 29,615-620 (2005).

Robin, X. et al. pROC: an open-source package for R and S+ to analyze and compare ROC curves. BMC Bioinformatics 12, 77 (2011).

Rosenthal, R. Meta-analytic Procedures for Social Research. (SAGE Publications, 1991).

Salsbury, A. J. The significance of the circulating cancer cell. Cancer Treat. Rev. 2, 55-72 (1975).

Sanchez-Freire, V., Ebert, A. D., Kalisky, T., Quake, S. R. & Wu, J. C. Microfluidic single-cellreal-time PCR for comparative analysis of gene expression patterns. Nature protocols 7, 829-38 (2012).

Schneider, C. A., Rasband, W. S. & Eliceiri, K. W. NIH Image to ImageJ: 25 years of image analysis. Nature Methods 9, 671-675 (2012).

Schug, J. et al. Promoter features related to tissue specificity as measured by Shannon entropy. Genome Biol. 6, R33 (2005).

Seal, S. H. A sieve for the isolation of cancer cells and other large cells from the blood. Cancer 17, 637-642 (1964).

Sellwood, R. A., Kuper, S. W., Burn, J. I. & Wallace, E. N. Circulating cancer cells. Br. Med. J. 1, 1683-1686 (1964).

Song, J., From, P., Morrissey, W. J. & Sams, J. Circulating cancer cells: pre- and post-chemotherapy observations. Cancer 28, 553-561 (1971).

St Croix, B. et al. Genes expressed in human tumor endothelium. Science 289, 1197-1202 (2000).

Stott, S. L et al. Isolation of circulating tumor cells using a microvortex-generating herringbone-chip. Proc. Natl. Acad. Sci. USA 107, 18392-18397 (2010).

Trapnell, C., Pachter, L. & Salzberg, S. L. TopHat: discovering splice junctions with RNA-Seq. Bioinformatics 25, 1105-1111 (2009).

Trapnell, C. et al. Transcript assembly and quantification by RNA-Seq reveals unannotated transcripts and isoform switching during cell differentiation. Nat. Biotechnol. 28, 511-515 (2010).

Wild, R., Ramakrishnan, S., Sedgewick, J. & Griffioen, A. W. Quantitative assessment of angiogenesis and tumor vessel architecture by computer-assisted digital image analysis: effects of VEGF-toxin conjugate on tumor microvessel density. Microvasc. Res. 59, 368-376 (2000).

Wu, C. et al. BioGPS: an extensible and customizable portal for querying and organizing gene annotation resources. Genome Biol. 10, R130 (2009).

Ye, J. et al. Primer-BLAST: A tool to design target-specific primers for polymerase chain reaction. BMC Bioinformatics 13, 134 (2012).

Yu, M. et al. Circulating breast tumor cells exhibit dynamic changes in epithelial and mesenchymal composition. Science 339, 580-584 (2013).

Van Beijnum, J. R., Rousch, M., Castermans, K., van der Linden, E. & Griffioen, A. W. Isolation of endothelial cells from fresh tissues. Nat. Protoc. 3, 1085-1091 (2008).

Vona, G. et al. Isolation by size of epithelial tumour cells: a new method for the immunomorphological and molecular characterization of circulating tumor cells. Am. J. Pathol. 156, 57-63 (2000).

Vona, G. 590 et al. Impact of cytomorphological detection of circulating tumor cells in patients with liver cancer. Hepatology 39, 792-797 (2004).

Zanetta, L. et al. Expression of Von Willebrand factor, an endothelial cell marker, is up-regulated by angiogenesis factors: a potential method for objective assessment of tumor angiogenesis. Int. J. Cancer 85, 281-288 (2000)

Zeileis, A., Wiel, M., Hornik, K. & Hothorn, T. Implementing a class of permutation tests: The coin package. J. Stat. Softw. 28, 1-23 (2008).

What is claimed is:

1. A method of simultaneously analyzing RNA and DNA in a sample, the method comprising the operations of:
   (a) contacting the sample with a reverse primer from a first primer pair, the reverse primer from the first primer pair being directed to a target RNA region, and a reverse transcriptase to effect reverse transcription of the RNA into cDNA;
   (b) subsequently contacting the sample with:
      (i) a forward primer from the first primer pair, the forward primer from the first primer pair being directed to a target cDNA region,
      (ii) a reverse primer and a forward primer from a second primer pair, the reverse primer and forward primer from the second primer pair being directed to a target DNA region, and
      (iii) a DNA polymerase to simultaneously amplify the target cDNA region and the target DNA region;
   (c) (A) subjecting the sample from operation (b) to a semi-nested PCR using the reverse primer in operation (a) or the forward primer in operation (b)(i), a nested primer that binds within the pre-amplified target cDNA region, and a DNA polymerase to further amplify the target cDNA region; and/or
      (B) subjecting the sample from operation (b) to a nested PCR using a nested primer pair that binds within the pre-amplified target DNA region and a DNA polymerase to further amplify the target DNA region; and
   (d) analyzing the amplified target cDNA region and/or the amplified target DNA region;
   wherein the sample comprises a single cell; and
   wherein prior to operation (a), the method does not comprise lysing the cell in the sample.

2. The method according to claim 1, wherein the simultaneous amplification in operation (b) is a pre-amplification operation.

3. The method according to claim 1, wherein operations (a) and (b) are conducted in the same reaction mixture.

4. The method according to claim 1, wherein the method is performed simultaneously for one or more target RNA regions, and/or one or more target cDNA regions, and/or one or more target DNA regions.

5. The method according to claim 1, wherein the single cell is selected from the group consisting of: a cell from a pre-implantation embryo, a stem cell, a suspected cancer cell, a suspected tumour-derived cell, a suspected embryonic cell, a cell from a pathogenic organism, and a cell obtained from a crime scene.

6. The method according to claim 1, wherein the first primer pair comprises primers that span exon-exon boundaries or are separated by at least one intron on the corresponding DNA region.

7. The method according to claim 1, wherein
   a) the forward primer of the first or second primer pair is selected from the group consisting of SEQ ID NOs 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85 and 87;
   b) the reverse primer of the first or second primer pair is selected from the group consisting of SEQ ID NOs: 2, 4, 6, 8, 10, 12, 14, 16, 18, 20, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86 and 88;
   c) the first or second primer pair is selected from the group consisting of SEQ ID NOs 1 and 2; SEQ ID NOs 3 and 4; SEQ ID NOs 5 and 6; SEQ ID NOs 7 and 8; SEQ ID NOs 9 and 10; SEQ ID NOs 11 and 12; SEQ ID NOs 13 and 14; SEQ ID NOs 15 and 16; SEQ ID NOs 17 and 18; SEQ ID NOs 19 and 20; SEQ ID NOs 21 and 22; SEQ ID NOs 23 and 24; SEQ ID NOs 25 and 26; SEQ ID NOs 27 and 28; SEQ ID NOs 29 and 30; SEQ ID NOs 31 and 32; SEQ ID NOs 33 and 34; SEQ ID NOs 35 and 36; SEQ ID NOs 37 and 38; SEQ ID NOs 39 and 40; SEQ ID NOs 41 and 42; SEQ ID NOs 43 and 44; SEQ ID NOs 45 and 46; SEQ ID NOs 47 and 48; SEQ ID NOs 49 and 50; SEQ ID NOs 51 and 52; SEQ ID NOs 53 and 54; SEQ ID NOs 55 and 56; SEQ ID NOs 57 and 58; SEQ ID NOs 59 and 60; SEQ ID NOs 61 and 62; SEQ ID NOs 63 and 64; SEQ ID NOs 65 and 66; SEQ ID NOs 67 and 68; SEQ ID NOs 69 and 70; SEQ ID NOs 71 and 72; SEQ ID NOs 73 and 74; SEQ ID NOs 75 and 76; SEQ ID NOs 77 and 78; SEQ ID NOs 79 and 80; SEQ ID NOs 81 and 82; SEQ ID NOs 83 and 84; SEQ ID NOs 85 and 86; and SEQ ID NOs 87 and 88;
   d) the forward primer for semi-nested or nested PCR is selected from the group consisting of SEQ ID NOs: 89, 90, 91, 92, 93, 94, 95, 15, 17, 19, 99, 23, 101, 102, 104, 105, 106, 107, 108, 110, 111, 43, 45, 115, 116, 117, 118, 55, 120, 59, 61, 123, 124, 125, 126, 71, 127, 75, 77, 130, 81, 132, 133 and 134;
   e) the reverse primer for semi-nested or nested PCR is selected from the group consisting of SEQ ID NOs: 2, 4, 6, 8, 10, 12, 14, 96, 97, 98, 22, 100, 26, 103, 30, 32, 34, 36, 109, 40, 112, 113, 114, 48, 50, 52, 54, 119, 58, 121, 122, 64, 66, 68, 70, 72, 74, 128, 129, 80, 131, 84, 86 and 88; or
   f) the primers for semi-nested or nested PCR is selected from the group consisting of SEQ ID NOs 89 and 2; SEQ ID NOs 90 and 4; SEQ ID NOs 91 and 6; SEQ ID NOs 92 and 8; SEQ ID NOs 93 and 10; SEQ ID NOs 94 and 12; SEQ ID NOs 95 and 14; SEQ ID NOs 15 and 96; SEQ ID NOs 17 and 97; SEQ ID NOs 19 and 98; SEQ ID NOs 99 and 22; SEQ ID NOs 23 and 100; SEQ ID NOs 101 and 26; SEQ ID NOs 102 and 103; SEQ ID NOs 104 and 30; SEQ ID NOs 105 and 32; SEQ ID NOs 106 and 34; SEQ ID NOs 107 and 36;

SEQ ID NOs 108 and 109; SEQ ID NOs 110 and 40; SEQ ID NOs 111 and 112; SEQ ID NOs 43 and 113; SEQ ID NOs 45 and 114; SEQ ID NOs 115 and 48; SEQ ID NOs 116 and 50; SEQ ID NOs 117 and 52; SEQ ID NOs 118 and 54; SEQ ID NOs 55 and 119; SEQ ID NOs 120 and 58; SEQ ID NOs 59 and 121; SEQ ID NOs 61 and 122; SEQ ID NOs 123 and 64; SEQ ID NOs 124 and 66; SEQ ID NOs 125 and 68; SEQ ID NOs 126 and 70; SEQ ID NOs 71 and 72; SEQ ID NOs 127 and 74; SEQ ID NOs 75 and 128; SEQ ID NOs 77 and 129; SEQ ID NOs 130 and 80; SEQ ID NOs 81 and 131; SEQ ID NOs 132 and 84; SEQ ID NOs 133 and 86; and SEQ ID NOs 134 and 88.

8. The method according to claim 1, wherein the second primer pair comprises primers that bind to intronic regions of the target DNA region.

9. The method according to claim 1, wherein operation (b) comprises one or more of the following: about 1 to about 50 cycling steps, and 3 cycling steps; and/or wherein the analysis in operation (c) comprises analyzing one or more of the following: the amplified target cDNA for gene expression, and the amplified target DNA for mutations.

10. The method according to claim 9, wherein each cycling step comprises one or more of the following: about 1 to about 50 cycles of denaturation, annealing and elongation, and 6 cycles of denaturation, annealing and elongation.

11. The method according to claim 10, wherein the annealing and/or elongation temperature in a cycle is about 40° C. to about 75° C. and/or wherein the annealing and/or elongation is carried out for about 10 seconds to about 10 minutes and/or wherein the denaturation is carried out at a temperature of about 75° C. to about 120° C. for about 1 second to about 10 minutes.

12. The method according to claim 1, wherein operation (b) comprises:
6 cycles of 60° C. for 4 minutes followed by 95° C. for 1 minute,
6 cycles of 55° C. for 4 minutes followed by 95° C. for 1 minute, and
6 cycles of 50° C. for 4 minutes followed by 95° C. for 1 minute, and/or does not comprise a final extension operation.

13. The method according to claim 1, wherein the nested primer is one that matches or corresponds to the reverse primer in operation (a) or the forward primer in operation (b)(i).

14. The method of claim 1, further comprising an operation of determining a DNA profile and/or a gene expression profile of a single cell by characterizing DNA sequences of a selection of genes within a cell and/or characterizing expression levels of a selection of genes within a cell.

* * * * *